(12) United States Patent  
Fischer et al.

(10) Patent No.: US 11,274,097 B2  
(45) Date of Patent: Mar. 15, 2022

(54) 2-(HET)ARYL-SUBSTITUTED CONDENSED BICYCLIC HETEROCYCLE DERIVATIVES AS PEST CONTROL AGENTS

(71) Applicant: BAYER CROPSCIENCE AKTIENGESELLSCHAFT, Monheim am Rhein (DE)

(72) Inventors: Ruediger Fischer, Pulheim (DE); Bernd Alig, Koenigswinter (DE); Kerstin Ilg, Cologne (DE); Olga Malsam, Roesrath (DE); Ulrich Goergens, Ratingen (DE); Andreas Turberg, Haan (DE); Jun Li, Hannover (DE); Sergey Zhersh, Brovary (UA); Alexander Arlt, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/385,249

(22) Filed: Apr. 16, 2019

(65) Prior Publication Data

US 2019/0241564 A1 Aug. 8, 2019

Related U.S. Application Data

(62) Division of application No. 15/119,124, filed as application No. PCT/EP2015/052351 on Feb. 5, 2015, now Pat. No. 10,364,243.

(30) Foreign Application Priority Data

Feb. 17, 2014 (EP) .................................... 14155372

(51) Int. Cl.
| | | |
|---|---|---|
| C07D 471/00 | (2006.01) | |
| C07D 471/04 | (2006.01) | |
| A01N 43/90 | (2006.01) | |
| C07D 213/73 | (2006.01) | |
| C07D 213/74 | (2006.01) | |
| C07D 473/40 | (2006.01) | |
| C07D 498/04 | (2006.01) | |
| C07D 487/04 | (2006.01) | |

(52) U.S. Cl.
CPC ............ *C07D 471/04* (2013.01); *A01N 43/90* (2013.01); *C07D 213/73* (2013.01); *C07D 213/74* (2013.01); *C07D 473/40* (2013.01); *C07D 487/04* (2013.01); *C07D 498/04* (2013.01)

(58) Field of Classification Search
CPC .................................................. C07D 473/80
See application file for complete search history.

(56) References Cited

U.S. PATENT DOCUMENTS

| 5,925,595 A | 7/1999 | Seitz et al. |
| 2003/0119675 A1 | 6/2003 | Wolf et al. |
| 2012/0245027 A1 | 9/2012 | Giner et al. |

FOREIGN PATENT DOCUMENTS

| EP | 0 079 083 A1 | 5/1983 |
| WO | 2004037823 A1 | 5/2004 |
| WO | 2012/086848 A1 | 6/2012 |
| WO | 2013/018928 A1 | 2/2013 |
| WO | PCT/CN2014/076736 | 5/2014 |
| WO | 2015/000715 A1 | 1/2015 |
| WO | WO-2015000715 A1 * | 1/2015 |
| WO | 2016/116338 A1 | 7/2016 |

OTHER PUBLICATIONS

International Search Report of PCT/EP2015/052351 dated Mar. 9, 2015.
American Chemical Society. STN Database. © Jan. 15, 2015. RN 1643138-99-1.
EP 13174698.4, filed Jul. 2, 2013.
EP 13176263.5, filed Jul. 12, 2013.
EP 13197069.1, filed Dec. 13, 2013.
M. W. Walter, "Structure-based design of agrochemicals," Natural Products Reports 19, 278-291(2002).
D. R. Suiter and M. E. Sharf, Insecticide Basics for the Pest Management Professional, 1-24 (2015), Bulletin 1352 of the University of Georgia Extension program(www.extension.uga.edu/publications).
J. D. McKinney, A. Richard, C. Waller, M. C. Newman, F. Gerberick, "The practice of structure-activity relationships (SAR) in toxicology." Toxicol. Sci. 56, 8-17 (2000).
S. Kar, K. Roy, and J. Leszczynski, "On Applications of QSARs in Food and Agricultural sciences: History and Critical Review of Recent Developments", pp. 203-302 in K. Roy (ed.), Advances in QSAR Modeling, Challenges and Advances in Computational Chemistry and Physics 24, doi 10.1007/978-3-319-56850-8 7.
D. Liszekova, M. Polakovicova, M. Beno, R.Farkas, Molecular Determinants of Juvenile Hormone Action as Revealed by 3D QSAR Analysis in *Drosophila*, PLoS ONE 4(6), e6001 (2009)(doi: 10.1371/journal.pone.0006001).

(Continued)

*Primary Examiner* — John S Kenyon
(74) *Attorney, Agent, or Firm* — White & Case LLP

(57) ABSTRACT

The invention relates to novel compounds of the formula (I)

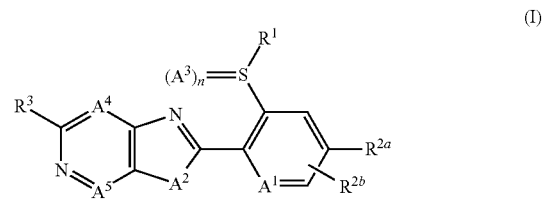

in which the $R^1$, $R^{2a}$, $R^{2b}$, $R^3$, $A^1$, $A^2$, $A^3$, $A^4$, $A^5$ and n radicals are each as defined above,
to the use thereof as acaricides and/or insecticides for controlling animal pests and to processes and intermediates for preparation thereof.

13 Claims, No Drawings

(56) References Cited

OTHER PUBLICATIONS

G. Yadav and S. Ganguly, "Structure activity relationship (SAR) study of benzimidazole scaffold for different biological activities: a mini-review", Eur. J Med. Chem. 97,419-443 (2015).

T. Wang, M. A. Block, S. Cowen, A. M. Davies, E. Devereaux, L. Gingiipalli, J. Johannes, N. A. Larsen, Q.Su, J. A. Tucker, D. Whitston, J. Wu, H-J. Zhang, M. Zinda, and C. Chuaqui, "Discovery of azabenimidazole derivatives as potent, selective inhibitors of TBK1/IKK☐ kinases," Bioorg. Med. Chem. Lett., 22, 2063-2069(2012).

Cudney, D.W. California Exotic Pest Plant Council, 1996 Symposium Proceedings.

K. Mori, "Chirality and Insect Pheromones," Chirality 10:578-586 (1998).

A. Williams, "Opportunities for Chiral Agrochemicals," Pestic. Sci. 46, 3-9 (1996).

Heterocyclic Compounds, https://www2.chemistry.msu.edu/faculty/reusch/VirtTxtJml/heterocy.htm.

Christopher Walsh, "Enzymatic Reaction Mechanisms," Freeman (San Francisco), 1979.

Robinson, P.K., "Enzymes: principles and biotechnological applications," Essays Biochem. 59: 1-41 (2015).

Redacted Declaration of Glenn D. Prestwich, Ph.D., (executed Apr. 30, 2020), Ex. No. 1003, PGR2020-00058 (U.S. Pat. No. 10,364,243).

Redacted Declaration of Remo Winter, (executed Apr. 29, 2020), Ex. No. 1011, PGR2020-00058 (U.S. Pat. No. 10,364,243).

Redacted Petition for Post-Grant Review, PGR2020-00058 (U.S. Pat. No. 10,364,243), dated Apr. 30, 2020.

Redacted Decision Granting Institution of Post-Grant Review, PGR2020-00058 (U.S. Pat. No. 10,364,243), dated Nov. 24, 2020.

* cited by examiner

2-(HET)ARYL-SUBSTITUTED CONDENSED BICYCLIC HETEROCYCLE DERIVATIVES AS PEST CONTROL AGENTS

CROSS-REFERENCE TO RELATED APPLICATIONS

This application is a Continuation Application of U.S. application Ser. No. 15/119,124, filed 15 Aug. 2016, now U.S. Pat. No. 10,364,243, which is a National Stage entry of International Application No. PCT/EP2015/052351, filed Feb. 5, 2015, which claims priority to European Patent Application No. 14155372.7, filed Feb. 17, 2014. The disclosures of the priority applications are incorporated in their entirety herein by reference.

BACKGROUND

Field of the Invention

The present invention relates to novel 2-(het)aryl-substituted fused bicyclic heterocycle derivatives of the formula (I), to the use thereof as acaricides and/or insecticides for controlling animal pests, particularly arthropods and especially insects and arachnids, and to processes and intermediates for preparation thereof.

Description of Related Art 2-(Het)aryl-substituted fused bicyclic heterocycle derivatives having insecticidal properties have already been described in the literature, for example in WO 2010/125985, WO 2012/074135, WO 2012/086848, WO 2013/018928, WO 2014/142292 and WO 2014/148451, and also WO 2015/000715.

However, the active ingredients already known according to the documents cited above have some disadvantages on application, whether because they exhibit only a narrow range of application or because they do not have satisfactory insecticidal or acaricidal activity.

SUMMARY

Novel 2-(het)aryl-substituted fused bicyclic heterocycle derivatives have now been found, and these have advantages over the compounds already known, examples of which are better biological or environmental properties, a wider range of application methods, better insecticidal or acaricidal activity, and also good compatibility with crop plants. The 2-(het)aryl-substituted fused bicyclic heterocycle derivatives can be used in combination with further agents for improving efficacy, especially against insects that are difficult to control.

The present invention therefore provides novel compounds of the formula (I)

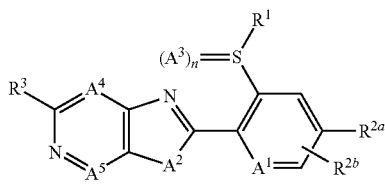

(I)

in which
$A^1$ is nitrogen, =N$^+$—O$^-$ or =C—R$^4$,
$A^2$ is —N—R, oxygen or sulphur,
$A^3$ is oxygen, =N—H or =N—CN,
$A^4$ is nitrogen, =N$^+$—O$^-$ or =C—R$^4$,
$A^5$ is nitrogen, =N$^+$—O$^-$ or =C—R$^4$,
$R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulphinyl-$(C_1-C_6)$alkyl, $(C_1-C_6)$haloalkylsulphinyl-$(C_1-C_6)$alkyl, $(C_1-C_6)$alkylsulphonyl-$(C_1-C_6)$alkyl, $(C_1-C_6)$haloalkylsulphonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulphinyl-$(C_1-C_6)$alkyl, $(C_1-C_6)$alkoxy-$(C_1-C_6)$alkylsulphonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulphonylamino, aminosulphonyl-$(C_1-C_6)$alkyl, $(C_1-C_6)$alkylaminosulphonyl-$(C_1-C_6)$alkyl, di$(C_1-C_6)$alkylaminosulphonyl-$(C_1-C_6)$alkyl, or is $(C_1-C_6)$alkyl, $(C_1-C_6)$alkoxy, $(C_2-C_6)$alkenyl, $(C_2-C_6)$alkynyl, $(C_3-C_8)$cycloalkyl, each of which is mono- or polysubstituted identically or differently by aryl, hetaryl or heterocyclyl, where aryl, hetaryl or heterocyclyl may each independently be mono- or polysubstituted identically or differently by halogen, cyano, nitro, hydroxyl, amino, carboxyl, carbamoyl, aminosulphonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl, or
$R^1$ is aryl, hetaryl or heterocyclyl, each of which is mono- or poly substituted identically or differently by halogen, cyano, nitro, hydroxyl, amino, carboxyl, carbamoyl, $(C_1-C_6)$alkyl, $(C_3-C_8)$cycloalkyl, $(C_1-C_6)$-alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl, (=O) (only in the case of heterocyclyl) or (=O)$_2$ (only in the case of heterocyclyl),
$R^{2a}$, $R^{2b}$, $R^3$ and $R^4$ are each independently hydrogen, cyano, halogen, nitro, acetyl, hydroxyl, amino, SCN, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy, —($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxy carbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di($C_1$-$C_6$)alkylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, is aryl or hetaryl, each of which is mono- or polysubstituted identically or differently, where (in the case of hetaryl) at least one carbonyl group may optionally be present and/or where possible substituents in each case are as follows: cyano, carboxyl, halogen, nitro, acetyl, hydroxyl, amino, SCN, tri-($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyakl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxy carbonyl-($C_1$-$C_6$)alkoxy, ($C_1$-$C_6$)alkoxy-$C_6$)alkoxy, ($C_1$-$C_6$)alkylhydroxyimino, ($C_1$-$C_6$)alkoxy imino, ($C_1$-$C_6$)alkyl-($C_1$-$C_6$)alkoxyimino, ($C_1$-$C_6$)haloalkyl-($C_1$-$C_6$)alkoxy imino, ($C_1$-$C_6$)alkylthio, ($C_1$-$C_6$)haloalkylthio, ($C_1$-$C_6$)alkoxy-$C_6$)alkylthio, ($C_1$-$C_6$)alkylthio-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)haloalkylcarbonyl, $C_6$)alkylcarbonyloxy, ($C_1$-$C_6$)alkoxy carbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di($C_1$-$C_6$)alkylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, $R^5$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy), —($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy), —($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulphinyl-($C_1$-$C_6$)alkyl, ($C_1$-$C_6$)haloalkylsulphinyl-($C_1$-$C_6$)alkyl, ($C_1$-$C_6$)alkylsulphonyl-($C_1$-$C_6$)alkyl, ($C_1$-$C_6$)haloalkylsulphonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulphinyl-($C_1$-$C_6$)alkyl, ($C_1$-$C_6$)alkoxy ($C_1$-$C_6$)alkylsulphonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxy carbonyl-($C_1$-$C_6$)alkyl, ($C_1$-$C_6$)haloalkoxy carbonyl-($C_1$-$C_6$)alkyl, aminocarbonyl-($C_1$-$C_6$)alkyl, ($C_1$-$C_6$)alkylamino-($C_1$-$C_6$)alkyl, di($C_1$-$C_6$)alkylamino-($C_1$-$C_6$)alkyl or ($C_3$-$C_8$)cycloalkylamino-($C_1$-$C_6$)alkyl, n is 0, 1 or 2, where, in the case that n=2, the meanings of $A^3$ may be the same or different.

It has additionally been found that the compounds of the formula (I) have very good efficacy as pesticides, preferably as insecticides and/or acaricides, and additionally generally have very good plant compatibility, especially with respect to crop plants.

DETAILED DESCRIPTION OF A PREFERRED EMBODIMENT

The inventive compounds are defined in general terms by the formula (I). Preferred substituents or ranges of the radicals given in the formulae mentioned above and below are illustrated hereinafter:

$A^1$ is preferably nitrogen, =$N^+$—$O^-$ or =C—$R^4$, $A^2$ is preferably —N—$R^5$, oxygen or sulphur, $A^3$ is preferably oxygen, =N—H or =N—CN, $A^4$ is preferably nitrogen, =$N^+$—$O^-$ or =C—$R^4$, $A^5$ is preferably nitrogen, =$N^+$—$O^-$ or =C—$R^4$, $R^1$ is preferably ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_6$)cycloalkyl, ($C_3$-$C_6$)cycloalkyl($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylamino, di($C_1$-$C_4$)alkylamino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulphinyl-($C_1$-$C_4$)alkyl, ($C_1$-$C_4$)haloalkylsulphinyl-($C_1$-$C_4$)alkyl, ($C_1$-$C_4$)alkylsulphonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulphonylamino, or is ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, each of which is optionally mono- or disubstituted identically or differently by aryl, hetaryl or heterocyclyl, where aryl, hetaryl and heterocyclyl may each optionally be mono- or disubstituted identically or differently by halogen, cyano, carbamoyl, aminosulphonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)alkylsulphimino, or $R^1$ is preferably aryl, hetaryl or heterocyclyl, each of which is optionally mono- or disubstituted identically or differently by halogen, cyano, carbamoyl, $(C_1-C_4)$alkyl, $(C_3-C_6)$cycloalkyl, $(C_1-C_4)$-alkoxy, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$alkylsulphimino, $(C_1-C_4)$alkylsulphoximino, $(C_1-C_4)$alkylcarbonyl, $(C_3-C_4)$trialkylsilyl, (=O) (only in the case of heterocyclyl) or (=O)$_2$ (only in the case of heterocyclyl), $R^{2a}$, $R^{2b}$, $R^3$ and $R^4$ are preferably each independently hydrogen, cyano, halogen, nitro, acetyl, hydroxyl, amino, SCN, tri-$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxy imino, $(C_1-C_4)$alkyl-$(C_1-C_4)$alkoxyimino, $(C_1-C_4)$haloalkyl-$(C_1-C_4)$alkoxy imino, $(C_1-C_4)$alkylthio, $(C_1-C_4)$haloalkylthio, $(C_1-C_4)$alkylthio-$(C_1-C_4)$alkyl, $(C_1-C_4)$alkylsulphinyl, $(C_1-C_4)$haloalkylsulphinyl, $(C_1-C_4)$alkylsulphinyl-$(C_1-C_4)$alkyl, $(C_1-C_4)$alkylsulphonyl, $(C_1-C_4)$haloalkylsulphonyl, $(C_1-C_4)$alkylsulphonyl-$(C_1-C_4)$alkyl, $(C_1-C_4)$alkylsulphonyloxy, $(C_1-C_4)$alkylcarbonyl, $(C_1-C_4)$haloalkylcarbonyl, aminocarbonyl, aminothiocarbonyl, $(C_1-C_4)$alkylaminocarbonyl, di$(C_1-C_4)$alkylaminocarbonyl, $(C_1-C_4)$alkylsulphonylamino, $(C_1-C_4)$alkylamino, di$(C_1-C_4)$alkylamino, amino sulphonyl, $(C_1-C_4)$alkylaminosulphonyl, di$(C_1-C_4)$alkylaminosulphonyl, aminothiocarbonyl, is phenyl or hetaryl, each of which is mono- or disubstituted identically or differently, where (in the case of hetaryl) at least one carbonyl group may optionally be present and/or where possible substituents in each case are as follows: cyano, halogen, nitro, acetyl, amino, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxy imino, $(C_1-C_4)$haloalkyl-$(C_1-C_4)$alkoxy imino, $(C_1-C_4)$alkylthio, $(C_1-C_4)$haloalkylthio, $(C_1-C_4)$alkylthio-$(C_1-C_4)$alkyl, $(C_1-C_4)$alkylsulphinyl, $(C_1-C_4)$haloalkylsulphinyl, $(C_1-C_4)$alkylsulphinyl-$(C_1-C_4)$alkyl, $(C_1-C_4)$alkylsulphonyl, $(C_1-C_4)$haloalkylsulphonyl, $(C_1-C_4)$alkylsulphonyl-$(C_1-C_4)$alkyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulphonylamino, $(C_1-C_4)$alkylamino, di$(C_1-C_4)$alkylamino, amino sulphonyl, $(C_1-C_4)$alkylaminosulphonyl, di$(C_1-C_4)$alkylaminosulphonyl, $R^5$ is preferably $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$haloalkylthio-$(C_1-C_4)$alkyl, $(C_1-C_4)$alkylsulphinyl-$(C_1-C_4)$alkyl, $(C_1-C_4)$haloalkylsulphinyl-$(C_1-C_4)$alkyl, $(C_1-C_4)$alkylsulphonyl-$(C_1-C_4)$alkyl, $(C_1-C_4)$haloalkylsulphonyl-$(C_1-C_4)$alkyl, $(C_1-C_4)$alkoxy-$(C_1-C_4)$alkylthio-$(C_1-C_4)$alkyl, $(C_1-C_4)$alkylcarbonyl-$(C_1-C_4)$alkyl, n is preferably 0, 1 or 2,
where, in the case that n=2, the meanings of $A^3$ may be the same or different.

$A^1$ is more preferably nitrogen or =C—$R^4$,
$A^2$ is more preferably —N—$R^5$ or oxygen,
$A^3$ is more preferably oxygen or =N—H,
$A^4$ is more preferably nitrogen or =C—$R^4$,
$A^5$ is more preferably nitrogen or =C—$R^4$,
$R^1$ is more preferably $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl, or is $(C_1-C_4)$alkyl optionally monosubstituted by phenyl, pyridyl, pyrimidyl, pyridazinyl, pyrazinyl, pyrazolyl, triazolyl, thiazolyl, tetrazolyl, piperazinyl, tetrahydrofuryl or oxetanyl, where phenyl, pyridyl, pyrimidyl, pyridazinyl, pyrazinyl, pyrazolyl, triazolyl, thiazolyl, tetrazolyl, piperazinyl, tetrahydrofuryl or oxetanyl may each optionally be mono- or disubstituted identically or differently by halogen, $(C_1-C_4)$alkyl or $(C_1-C_4)$haloalkyl, or $R^1$ is more preferably phenyl, pyridyl, pyrimidyl, pyridazinyl, pyrazinyl, pyrazolyl, triazolyl, thiazolyl, tetrazolyl, piperazinyl, tetrahydrofuryl or oxetanyl, each of which is optionally mono- or disubstituted identically or differently by halogen, $(C_1-C_4)$alkyl or $(C_1-C_4)$haloalkyl, $R^{2a}$ is more preferably hydrogen, halogen, $(C_1-C_4)$alkyl $(C_1-C_4)$haloalkyl, $(C_1-C_4)$alkylthio, $(C_1-C_4)$alkylsulphinyl, $(C_1-C_4)$alkylsulphonyl, $(C_1-C_4)$haloalkylthio, $(C_1-C_4)$haloalkylsulphinyl or $(C_1-C_4)$haloalkylsulphonyl, $R^{2b}$ is more preferably hydrogen or halogen, $R^3$ is more preferably hydrogen, $(C_1-C_4)$alkyl $(C_1-C_4)$haloalkyl, $(C_1-C_4)$alkylthio, $(C_1-C_4)$alkylsulphinyl, $(C_1-C_4)$alkylsulphonyl, $(C_1-C_4)$haloalkylthio, $(C_1-C_4)$haloalkylsulphinyl or $(C_1-C_4)$haloalkylsulphonyl, $R^4$ is more preferably hydrogen, halogen, cyano or $(C_1-C_3)$alkyl, $R^5$ is more preferably $(C_1-C_4)$alkyl or $(C_1-C_4)$alkoxy-$(C_1-C_4)$alkyl, n is more preferably 0, 1 or 2,
where, in the case that n=2, the meanings of $A^3$ may be the same or different.

$A^1$ is even more preferably nitrogen or =C—$R^4$,
$A^2$ is even more preferably N—$R^5$ or oxygen,
$A^3$ is even more preferably oxygen,
$A^4$ is even more preferably nitrogen or =C—H,
$A^5$ is even more preferably nitrogen or =C—H,
$R^1$ is even more preferably methyl, ethyl, n-propyl, i-propyl, cyclopropyl, n-butyl, i-butyl, tert-butyl, cyclobutyl, fluoromethyl, difluoromethyl, trifluoromethyl, fluoroethyl, difluoroethyl, trifluoroethyl, tetrafluoroethyl, pentafluoroethyl, —$(CH_2)_2$—S—$C_2H_5$, —$(CH_2)_2$—$SO_2$—$C_2H_5$ or

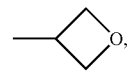

$R^{2a}$ is even more preferably hydrogen, fluoromethyl, difluoromethyl, trifluoromethyl, fluoroethyl, difluoroethyl, trifluoroethyl, tetrafluoroethyl, pentafluoroethyl, trifluoromethylthio, trifluoromethylsulphonyl, trifluoromethylsulphinyl, fluorine or chlorine, $R^{2b}$ is even more preferably hydrogen, fluorine or chlorine,
$R^3$ is even more preferably fluoromethyl, difluoromethyl, trifluoromethyl, fluoroethyl, difluoroethyl, trifluoroethyl, tetrafluoroethyl, pentafluoroethyl, trifluoromethylthio, trifluoromethylsulphonyl or trifluoromethylsulphinyl,
$R^4$ is even more preferably hydrogen, fluorine, chlorine, bromine or cyano,
$R^5$ is even more preferably methyl, ethyl, i-propyl, methoxymethyl or methoxyethyl,
n is even more preferably 0, 1 or 2.
$A^1$ is specifically nitrogen (N) or =C—H,
$A^2$ is specifically N—$CH_3$ or oxygen (O),
$A^3$ is specifically oxygen (O),
$A^4$ is specifically nitrogen (N) or =C—H,
$A^5$ is specifically =C—H,
$R^1$ is specifically methyl, ethyl, n-propyl, i-propyl, trifluoromethyl, —$(CH_2)_2$—S—$C_2H_5$, —$(CH_2)_2$—$SO_2$—$C_2H_5$ or

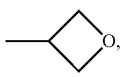

$R^{2a}$ is specifically hydrogen, trifluoromethyl, fluorine or chlorine,
$R^{2b}$ is specifically hydrogen or chlorine,
$R^3$ is specifically trifluoromethyl,
n is specifically 0, 1 or 2.

In a further preferred embodiment, the invention relates to compounds of the formula (I-A)

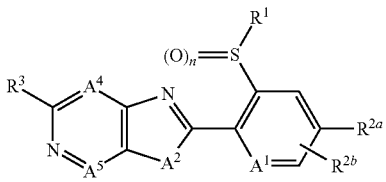

In a further preferred embodiment, the invention relates to compounds of the formula (I-B)

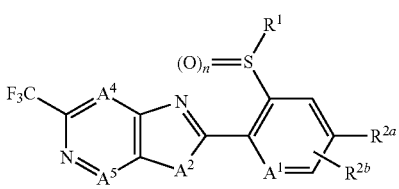

In a further preferred embodiment, the invention relates to compounds of the formula (I-C)

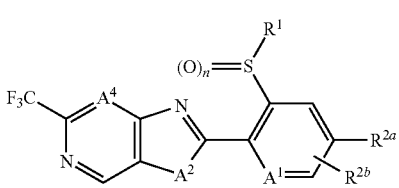

In a further preferred embodiment, the invention relates to compounds of the formula (I-D)

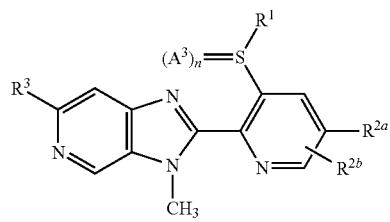

In a further preferred embodiment, the invention relates to compounds of the formula (I-E)

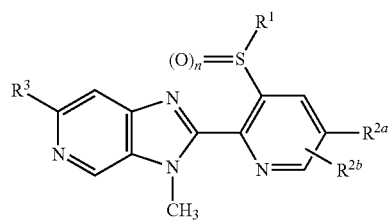

In a further preferred embodiment, the invention relates to compounds of the formula (I-F)

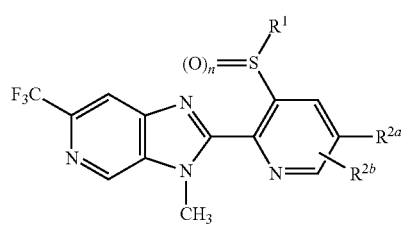

In a further preferred embodiment, the invention relates to compounds of the formula (I-G)

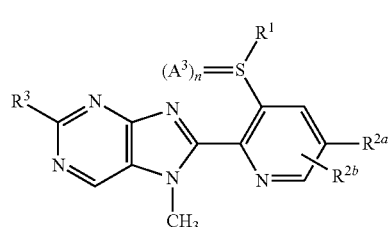

In a further preferred embodiment, the invention relates to compounds of the formula (I-H)

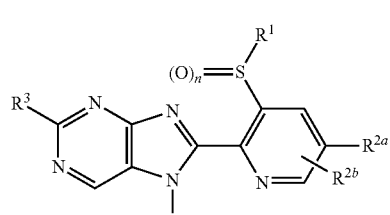

In a further preferred embodiment, the invention relates to compounds of the formula (I-I)

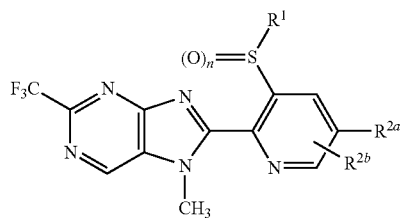

In a further preferred embodiment, the invention relates to compounds of the formula (I-J)

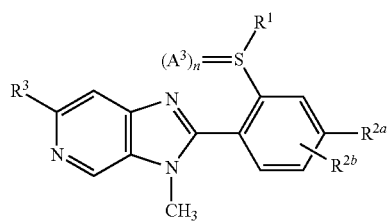

In a further preferred embodiment, the invention relates to compounds of the formula (I-K)

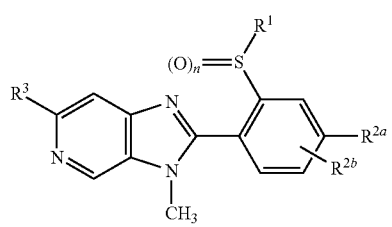

In a further preferred embodiment, the invention relates to compounds of the formula (I-L)

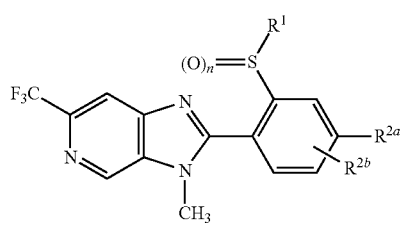

In a further preferred embodiment, the invention relates to compounds of the formula (I-M)

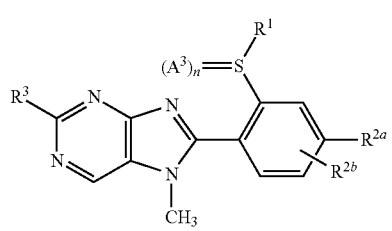

In a further preferred embodiment, the invention relates to compounds of the formula (I-N)

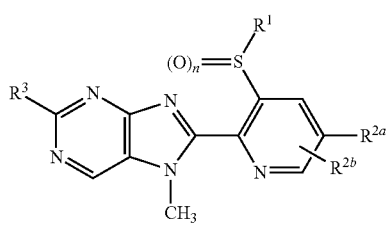

In a further preferred embodiment, the invention relates to compounds of the formula (I-O)

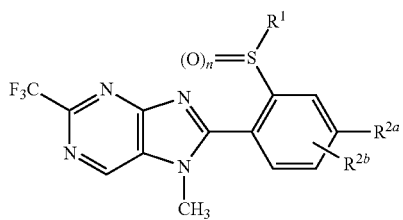

In a further preferred embodiment, the invention relates to compounds of the formula (I-P)

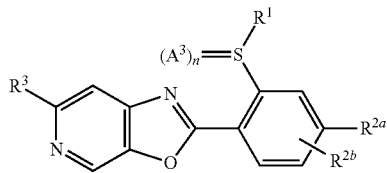

In a further preferred embodiment, the invention relates to compounds of the formula (I-Q)

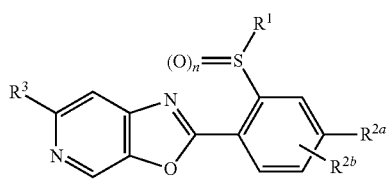

In a further preferred embodiment, the invention relates to compounds of the formula (I-R)

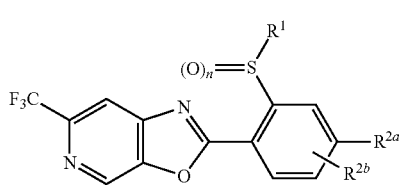

In a further preferred embodiment, the invention relates to compounds of the formula (I-S)

In a further preferred embodiment, the invention relates to compounds of the formula (I-T)

In a further preferred embodiment, the invention relates to compounds of the formula (I-U)

In a further preferred embodiment, the invention relates to compounds of the formula (I-V)

In a further preferred embodiment, the invention relates to compounds of the formula (I-W)

In a further preferred embodiment, the invention relates to compounds of the formula (I-X)

In the formulae (I-A) to (I-X), the $R^1$, $R^{2a}$, $R^{2b}$, $R^3$, $A^1$, $A^2$, $A^3$, $A^4$, $A^5$ and n radicals are each as defined above.

In a further embodiment (Configuration 1), the invention relates to compounds of the formula (I)

(I)

in which
$A^1$ is nitrogen, $=N^+-O^-$ or $=C-R^4$,
$A^1$ is $-N-R^5$, oxygen or sulphur,
$A^3$ is oxygen,
$A^4$ is nitrogen, $=N^+-O^-$ or $=C-R^4$,
$A^5$ is $=C-H$,
$R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulphinyl-$(C_1-C_6)$alkyl, $(C_1-C_6)$haloalkylsulphinyl-$(C_1-C_6)$alkyl, $(C_1-C_6)$alkylsulphonyl-$(C_1-C_6)$alkyl, $(C_1-C_6)$haloalkylsulphonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulphinyl-$(C_1-C_6)$alkyl, $(C_1-C_6)$alkoxy-$(C_1-C_6)$alkylsulphonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulphonylamino, aminosulphonyl-$(C_1-C_6)$alkyl, $(C_1-C_6)$alkylaminosulphonyl-$(C_1-C_6)$alkyl, di$(C_1-C_6)$alkylaminosulphonyl-$(C_1-C_6)$alkyl,
or is in each case identically or differently optionally mono- or poly-aryl-, -hetaryl- or -heterocyclyl-substituted $(C_1-C_6)$alkyl, $(C_1-C_6)$alkoxy, $(C_2-C_6)$alkenyl, $(C_2-C_6)$alkynyl, $(C_3-C_8)$cycloalkyl, where aryl, hetaryl or heterocyclyl may each independently be mono- or polysubstituted identically or differently by halogen, cyano, nitro, hydroxyl, amino, carboxyl, carbamoyl, aminosulphonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl, or $R^1$ is aryl, hetaryl or heterocyclyl, each of which is optionally mono- or polysubstituted identically or differently by halogen, cyano, nitro, hydroxyl, amino, carboxyl, carbamoyl, $(C_1-C_6)$alkyl, $(C_3-C_8)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl, (=O) (only in the case of heterocyclyl) or $(=O)_2$ (only in the case of heterocyclyl), $R^{2a}$, $R^{2b}$, $R^3$ and $R^4$ are each independently hydrogen, cyano, halogen, nitro, acetyl, hydroxyl, amino, SCN, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulphinyl, $(C_1-C_6)$haloalkylsulphinyl, $(C_1-C_6)$alkoxy-$(C_1-C_6)$alkylsulphinyl, $(C_1-C_6)$alkylsulphinyl-$(C_1-C_6)$alkyl, $(C_1-C_6)$alkylsulphonyl, $(C_1-C_6)$haloalkylsulphonyl, $(C_1-C_6)$alkoxy-$(C_1-C_6)$alkylsulphonyl, $(C_1-C_6)$alkylsulphonyl-$(C_1-C_6)$alkyl, $(C_1-C_6)$alkylsulphonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$-alkenylaminocarbonyl, $(C_3-C_8)$cycloalkylaminocarbonyl, $(C_1-C_6)$alkylsulphonylamino, $(C_1-C_6)$alkylamino, di$(C_1-C_6)$alkylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl, di$(C_1-C_6)$alkylaminothiocarbonyl, $(C_3-C_8)$cycloalkylamino, NHCO—$(C_1-C_6)$alkyl ($(C_1-C_6)$alkylcarbonylamino), is aryl or hetaryl, each of which is optionally mono- or polysubstituted identically or differently, where (in the case of hetaryl) at least one carbonyl group may optionally be present and/or where possible substituents in each case are as follows: cyano, carboxyl, halogen, nitro, acetyl, hydroxyl, amino, SCN, tri-$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy, —$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulphinyl, $(C_1-C_6)$haloalkylsulphinyl, $(C_1-C_6)$alkoxy-$(C_1-C_6)$alkylsulphinyl, $(C_1-C_6)$alkylsulphinyl-$(C_1-C_6)$alkyl, $(C_1-C_6)$alkylsulphonyl, $(C_1-C_6)$haloalkylsulphonyl, $(C_1-C_6)$alkoxy-$(C_1-C_6)$alkylsulphonyl, $(C_1-C_6)$alkylsulphonyl-$(C_1-C_6)$alkyl, $(C_1-C_6)$alkylsulphonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$-alkenylaminocarbonyl, $(C_3-C_8)$cycloalkylaminocarbonyl, $(C_1-C_6)$alkylsulphonylamino, $(C_1-C_6)$alkylamino, di$(C_1-C_6)$alkylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl, di$(C_1-C_6)$alkylaminothiocarbonyl, $(C_3-C_8)$cycloalkylamino, $R^5$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkylthio-$(C_1-C_6)$alkyl, $(C_1-C_6)$haloalkylthio-$(C_1-C_6)$alkyl, $(C_1-C_6)$alkylsulphinyl-$(C_1-C_6)$alkyl, $(C_1-C_6)$haloalkylsulphinyl-$(C_1-C_6)$alkyl, $(C_1-C_6)$alkylsulphonyl-$(C_1-C_6)$alkyl, $(C_1-C_6)$haloalkylsulphonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulphinyl-$(C_1-C_6)$alkyl, $(C_1-C_6)$alkoxy-$(C_1-C_6)$alkylsulphonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, aminocarbonyl-$(C_1-C_6)$alkyl, $(C_1-C_6)$alkylamino-$(C_1-C_6)$alkyl, di$(C_1-C_6)$alkylamino-$(C_1-C_6)$alkyl or $(C_3-C_8)$cycloalkylamino-$(C_1-C_6)$alkyl, n is 0, 1 or 2.

Preference (Configuration 2) is given to compounds of the formula (I) in which $A^1$ is nitrogen, $=N^+-O^-$ or $=C-R^4$,
$A^2$ is $-N-R^5$, oxygen or sulphur,
$A^3$ is oxygen,
$A^4$ is nitrogen, $=N^+-O^-$ or $=C-R^4$,
$A^5$ is $=C-H$,
$R^1$ is $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl$(C_3-C_6)$cycloalkyl, $(C_1-C_4)$alkyl-$(C_3-C_6)$cycloalkyl, halo$(C_3-C_6)$cycloalkyl, $(C_1-C_4)$alkylamino, di$(C_1-C_4)$alkylamino, $(C_3-C_6)$cycloalkylamino, $(C_1-C_4)$alkylcarbonylamino, $(C_1-C_4)$alkylthio-$(C_1-C_4)$alkyl, $(C_1-C_4)$haloalkylthio-$(C_1-

15

$C_4$)alkyl, ($C_1$-$C_4$)alkylsulphinyl-($C_1$-$C_4$)alkyl, ($C_1$-$C_4$)haloalkylsulphinyl-($C_1$-$C_4$)alkyl, ($C_1$-$C_4$)alkylsulphonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulphonylamino, or is ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, each of which is optionally mono- or disubstituted identically or differently by aryl, hetaryl or heterocyclyl, where aryl, hetaryl and heterocyclyl may each optionally be mono- or disubstituted identically or differently by halogen, cyano, carbamoyl, aminosulphonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)alkylsulphimino, or $R^1$ is aryl, hetaryl or heterocyclyl, each of which is optionally mono- or disubstituted identically or differently by halogen, cyano, carbamoyl, ($C_1$-$C_4$)alkyl, ($C_3$-$C_6$)cycloalkyl, ($C_1$-$C_4$)-alkoxy, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)alkylsulphimino, ($C_1$-$C_4$)alkylsulphoximino, ($C_1$-$C_4$)alkylcarbonyl, ($C_3$-$C_4$)trialkylsilyl, (=O) (only in the case of heterocyclyl) or (=O)$_2$ (only in the case of heterocyclyl), $R^{2a}$, $R^{2b}$, $R^3$ and $R^4$ are each independently hydrogen, cyano, halogen, nitro, acetyl, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy, —($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxy imino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulphonylamino, ($C_1$-$C_4$)alkylamino, di($C_1$-$C_4$)alkylamino, aminosulphonyl, ($C_1$-$C_4$)alkylaminosulphonyl, di($C_1$-$C_4$)alkylaminosulphonyl, aminothiocarbonyl, NHCO—($C_1$-$C_4$)alkyl (($C_1$-$C_4$)alkylcarbonylamino), is phenyl or hetaryl, each of which is mono- or disubstituted identically or differently, where (in the case of hetaryl) at least one carbonyl group may optionally be present and/or where possible substituents in each case are as follows: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxy imino, ($C_1$-$C_4$)alkyl-($C_1$-$C_4$)alkoxy imino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulphonylamino, ($C_1$-$C_4$)alkylamino, di($C_1$-$C_4$)alkylamino, aminosulphonyl, ($C_1$-$C_4$)alkylaminosulphonyl, di($C_1$-$C_4$)alkylaminosulphonyl, $R^5$ is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulphinyl-($C_1$-$C_4$)alkyl, ($C_1$-$C_4$)haloalkylsulphinyl-($C_1$-$C_4$)alkyl, ($C_1$-$C_4$)alkylsulphonyl-($C_1$-$C_4$)alkyl, ($C_1$-$C_4$)haloalkylsulphonyl-($C_1$-$C_4$)alkyl, ($C_1$-$C_4$)alkoxy-($C_1$-$C_4$)alkylthio-($C_1$-$C_4$)alkyl, ($C_1$-$C_4$)alkylcarbonyl-($C_1$-$C_4$)alkyl, n is 0, 1 or 2.

Particular preference (Configuration 3) is given to compounds of the formula (I) in which $A^1$ is nitrogen or =C—$R^4$,
$A^2$ is —N—$R^5$ or oxygen,
$A^3$ is oxygen,
$A^4$ is nitrogen or =C—$R^4$,
$A^5$ is =C—H, $R^1$ is ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl, or is ($C_1$-$C_4$)alkyl optionally monosubstituted by phenyl, pyridyl, pyrimidyl, pyridazinyl, pyrazinyl, pyrazolyl, triazolyl, thiazolyl, tetrazolyl, piperazinyl, tetrahydrofuryl or oxetanyl, where phenyl, pyridyl, pyrimidyl, pyridazinyl, pyrazinyl, pyrazolyl, triazolyl, thiazolyl, tetrazolyl, piperazinyl, tetrahydrofuryl or oxetanyl may each optionally be mono- or disubstituted identically or differently by halogen, ($C_1$-$C_4$)alkyl or ($C_1$-$C_4$)haloalkyl, or $R^1$ is phenyl, pyridyl, pyrimidyl, pyridazinyl, pyrazinyl, pyrazolyl, triazolyl, thiazolyl, tetrazolyl, piperazinyl, tetrahydrofuryl or oxetanyl, each of which is optionally mono- or disubstituted identically or differently by halogen, ($C_1$-$C_4$)alkyl or ($C_1$-$C_4$)haloalkyl, $R^{2a}$ is hydrogen, cyano, aminocarbonyl, halogen, ($C_1$-$C_4$)alkyl, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)haloalkylthio, ($C_1$-$C_4$)haloalkylsulphinyl or ($C_1$-$C_4$)haloalkylsulphonyl, $R^{2b}$ is hydrogen, ($C_1$-$C_4$)alkoxy, ($C_1$-$C_4$)haloalkyl, NHCO—($C_1$-$C_4$)alkyl or halogen, $R^3$ is hydrogen, halogen, ($C_1$-$C_4$)alkyl, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)haloalkylthio, ($C_1$-$C_4$)haloalkylsulphinyl, ($C_1$-$C_4$)haloalkylsulphonyl, or is phenyl, pyrazolyl or imidazolyl, each of which is optionally monosubstituted by trifluoromethyl, $R^4$ is hydrogen, halogen, cyano or ($C_1$-$C_3$)alkyl,
$R^5$ is ($C_1$-$C_4$)alkyl or ($C_1$-$C_4$)alkoxy-($C_1$-$C_4$)alkyl,
n is 0, 1 or 2.

Very particular preference (Configuration 4) is given to compounds of the formula (I) in which $A^1$ is nitrogen or $=C-R^4$,
$A^2$ is $-N-R^5$ or oxygen,
$A^3$ is oxygen,
$A^4$ is nitrogen or $=C-H$,
$A^5$ is $=C-H$,
$R^1$ is methyl, ethyl, n-propyl, i-propyl, cyclopropyl, n-butyl, i-butyl, tert-butyl, cyclobutyl, hydroxyethyl ($-CH_2-CH_2-OH$), fluoromethyl, difluoromethyl, trifluoromethyl, fluoroethyl, difluoroethyl, trifluoroethyl, tetrafluoroethyl, pentafluoroethyl, $-(CH_2)_2-S-C_2H_5$, $-(CH_2)_2-SO_2-C_2H_5$ or

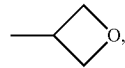

$R^{2a}$ is hydrogen, cyano, aminocarbonyl ($CONH_2$), fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl, trifluoromethylsulphinyl, fluorine or chlorine,
$R^{2b}$ is hydrogen, methoxy, ethoxy, trifluoromethyl, methylcarbonylamino (NHCO-methyl), fluorine or chlorine,
$R^3$ is fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl, trifluoromethylsulphinyl, or is phenyl, pyrazol-1-yl or imidazol-1-yl, each of which is optionally monosubstituted by trifluoromethyl,
$R^4$ is hydrogen, fluorine, chlorine, bromine or cyano,
$R^5$ is methyl, ethyl, i-propyl, methoxymethyl or methoxyethyl,
n is 0, 1 or 2.

Emphasis (Configuration 5) is given to compounds of the formula (I) in which
$A^1$ is nitrogen (N) or $=C-H$,
$A^2$ is $-N-CH_3$ or oxygen (O),
$A^3$ is oxygen (O),
$A^4$ is nitrogen (N) or $=C-H$,
$A^5$ is $=C-H$,
$R^1$ is methyl, ethyl, n-propyl, i-propyl, cyclopropyl, n-butyl, i-butyl, tert-butyl, cyclobutyl, hydroxyethyl ($-CH_2-CH_2-OH$), fluoromethyl, difluoromethyl, trifluoromethyl, fluoroethyl, difluoroethyl, trifluoroethyl, tetrafluoroethyl, pentafluoroethyl, $-(CH_2)_2-S-C_2H_5$, $-(CH_2)_2-SO_2-C_2H_5$ or

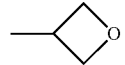

(oxetan-3-yl),
$R^{2a}$ is hydrogen, cyano, aminocarbonyl ($CONH_2$), fluoromethyl, difluoromethyl, trifluoromethyl, fluoroethyl, difluoroethyl, trifluoroethyl, tetrafluoroethyl, pentafluoroethyl, trifluoromethoxy, trifluoromethylthio, trifluoromethylsulphonyl, trifluoromethylsulphinyl, fluorine or chlorine,
$R^{2b}$ is hydrogen, methoxy, ethoxy, trifluoromethyl, methylcarbonylamino (NHCO-methyl), fluorine or chlorine, $R^3$ is fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, trifluoromethylthio, trifluoromethylsulphonyl, trifluoromethylsulphinyl, or is phenyl,

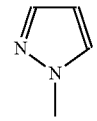

(pyrazol-1-yl) or

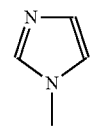

(imidazol-1-yl), each of which is optionally monosubstituted by trifluoromethyl,
n is 0, 1 or 2.

Particular emphasis (Configuration 6) is given to compounds of the formula (I) in which
$A^1$ is nitrogen (N) or $=C-H$,
$A^2$ is $-N-CH_3$ or oxygen (O),
$A^3$ is oxygen (O),
$A^4$ is nitrogen (N) or $=C-H$,
$A^5$ is $=C-H$,
$R^1$ is methyl, ethyl, n-propyl, i-propyl, trifluoromethyl, $-CH_2-CH_2-F$, $-CH_2-CH_2-OH$, $-(CH_2)_2-S-C_2H_5$, $-(CH_2)_2-SO_2-C_2H_5$ or

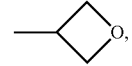

$R^{2a}$ is hydrogen, trifluoromethyl, cyano, $CONH_2$, fluorine or chlorine,
$R^{2b}$ is hydrogen, chlorine, trifluoromethyl, methoxy or $NHCOCH_3$,
$R^3$ is pentafluoroethyl, trifluoromethyl, chlorine, 4-$CF_3$ ($C_6H_4$), 4-($CF_3$)pyrazol-1-yl, 3-($CF_3$)pyrazol-1-yl or 4-($CF_3$)imidazol-1-yl,
n is 0, 1 or 2.

In a further preferred embodiment, the invention relates to the compounds of the formula (I) where $R^1$, $R^{2a}$, $R^3$, $A^1$, $A^2$, $A^3$, $A^4$, $A^5$ and n are each as defined above, especially as defined in Configuration (1) or Configuration (2) or Configuration (3) or Configuration (4) or Configuration (5) or Configuration (6), and $R^{2b}$ is acetyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl($C_3$-$C_8$)cycloalkyl (where the bond is via the cycloalkyl substituted by alkyl), halo($C_3$-$C_8$)cycloalkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyloxy, ($C_1$-$C_6$)alkylcarbonyl, ($C_1$-$C_6$)haloalkylcarbonyl, ($C_1$-$C_6$)alkylthiocarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), is in each case optionally singly or multiply, identically or differently substituted hetaryl, where at least one carbonyl group may optionally be present and/or where possible substituents in each case are as follows: cyano, carboxyl, halogen, nitro, acetyl, hydroxyl, amino, SCN, tri-($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy, —($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxy imino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxy carbonyl, ($C_1$-$C_6$)haloalkoxy carbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino.

In a further preferred embodiment, the invention relates to the compounds of the formula (I) where $R^1$, $R^{2a}$, $R^3$, $A^1$, $A^2$, $A^3$, $A^4$, $A^5$ and n are each as defined above, especially as defined in Configuration (1) or Configuration (2) or Configuration (3) or Configuration (4) or Configuration (5) or Configuration (6), and $R^{2b}$ is acetyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl($C_3$-$C_6$)cycloalkyl (where the bond is via the cycloalkyl substituted by alkyl), halo($C_3$-$C_6$)cycloalkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkylsulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, aminothiocarbonyl, NHCO—($C_1$-$C_4$)alkyl ((($C_1$-$C_4$)alkylcarbonylamino), is in each case singly or doubly, identically or differently substituted hetaryl, where at least one carbonyl group may optionally be present and/or where possible substituents in each case are as follows: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxy imino, ($C_1$-$C_4$)haloalkyl-($C_1$-$C_4$)alkoxy imino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl.

In a further preferred embodiment, the invention relates to the compounds of the formula (I) where $R^1$, $R^{2a}$, $R^3$, $A^1$, $A^2$, $A^3$, $A^4$, $A^5$ and n are each as defined above, especially as defined in Configuration (1) or Configuration (2) or Configuration (3) or Configuration (4) or Configuration (5) or Configuration (6), and $R^{2b}$ is ($C_1$-$C_4$)alkoxy or NHCO—($C_1$-$C_4$)alkyl.

In a further preferred embodiment, the invention relates to the compounds of the formula (I) where $R^1$, $R^{2a}$, $R^3$, $A^1$, $A^2$, $A^3$, $A^4$, $A^5$ and n are each as defined above, especially as defined in Configuration (1) or Configuration (2) or Configuration (3) or Configuration (4) or Configuration (5) or Configuration (6), and $R^{2b}$ is methoxy, ethoxy or NHCO-methyl.

In a further preferred embodiment, the invention relates to the compounds of the formula (I) where $R^1$, $R^{2a}$, $R^3$, $A^1$, $A^2$, $A^3$, $A^4$, $A^5$ and n are each as defined above, especially as defined in Configuration (1) or Configuration (2) or Configuration (3) or Configuration (4) or Configuration (5) or Configuration (6), and $R^{2b}$ is methoxy or NHCO-methyl.

$R^{2b}$ is joined in the 3 or 5 position:

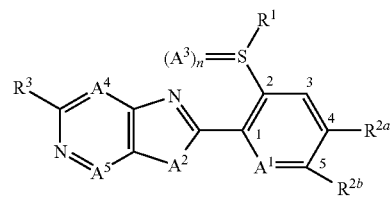

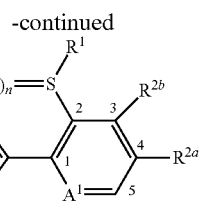

In the preferred definitions, unless stated otherwise,
halogen is selected from the group of fluorine, chlorine, bromine and iodine, preferably in turn from the group of fluorine, chlorine and bromine,
aryl (including as part of a larger unit, for example arylalkyl) is selected from the group of phenyl, naphthyl, anthryl, phenanthrenyl, and is preferably in turn phenyl,
hetaryl (synonymous with heteroaryl, including as part of a larger unit, for example hetarylalkyl) is selected from the group of furyl, thienyl, pyrrolyl, pyrazolyl, imidazolyl, triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, pyridyl, pyrimidyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl,
heterocyclyl is a saturated 4-, 5- or 6-membered ring containing 1 or 2 nitrogen atoms and/or one oxygen atom and/or one sulphur atom, for example azetidinyl, pyrrolidinyl, piperidinyl, oxetanyl, tetrahydrofuranyl, tetrahydropyranyl, dioxanyl, thietanyl, tetrahydrothiophenyl, tetrahydrothiopyranyl, piperazinyl, morpholinyl and thiomorpholinyl.

In the particularly preferred definitions, unless stated otherwise,
halogen is selected from the group of fluorine, chlorine, bromine and iodine, preferably in turn from the group of fluorine, chlorine and bromine,
aryl (including as part of a larger unit, for example arylalkyl) is selected from the group of phenyl, naphthyl, anthryl, phenanthrenyl, and is preferably in turn phenyl,
hetaryl (including as part of a larger unit, for example hetarylalkyl) is selected from the group of pyridyl, pyrimidyl, pyrazinyl, pyridazinyl, pyrazolyl, imidazolyl, triazolyl, thiazolyl and tetrazolyl,
heterocyclyl is selected from the group of oxetanyl, tetrahydrofuryl and piperazinyl.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. From among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms can be identical or different. In this case, halogen is fluorine, chlorine, bromine or iodine, especially fluorine, chlorine or bromine.

Unless stated otherwise, optionally substituted radicals may be mono- or polysubstituted, where the substituents in the case of poly substitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to using compounds of the formula (I) where a combination of the definitions listed above as preferred is present.

Particular preference is given in accordance with the invention to using compounds of the formula (I) where a combination of the definitions listed above as particularly preferred is present.

Very particular preference is given in accordance with the invention to using compounds of the formula (I) where a combination of the definitions listed above as very particularly preferred is present.

Emphasis is given in accordance with the invention to using compounds of the formula (I) where a combination of the definitions listed above as specific is present.

Particular emphasis is given in accordance with the invention to using compounds of the formula (I) where a combination of the definitions listed above as very specific is present.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention thus encompasses pure stereoisomers and any desired mixtures of these isomers.

The inventive compounds of the formula (I) can be obtained by the processes shown in the following schemes:

Process A

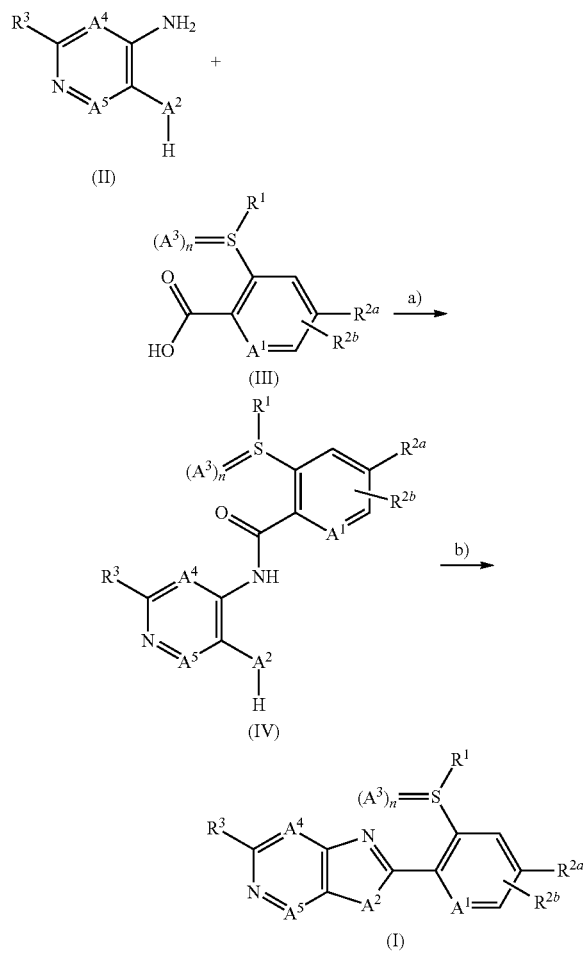

The $R^1$, $R^{2a}$, $R^{2b}$, $R^3$, $A^1$, $A^2$, $A^3$, $A^4$, $A^5$ and n radicals are each as defined above.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent.

Compounds of the formula (II) are either commercially available or can be prepared by known methods, for example analogously to the processes described in US2003/69257 or WO2006/65703.

Carboxylic acids of the formula (III) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (II) with carboxylic acids of the formula (III) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

The reaction can be effected under reduced pressure, at standard pressure or under elevated pressure and at temperatures of 0 to 180° C., preference being given to effecting the reaction at standard pressure and temperatures of 20 to 140° C.

Step b)

The compounds of the formula (I) can be prepared by condensing the compounds of the formula (IV), for example analogously to the processes described in WO2012/86848.

The conversion to compounds of the formula (I) can be effected neat or in a solvent, preference being given to conducting the reaction in a solvent selected from the customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be conducted in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

Process B

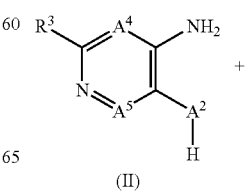

-continued

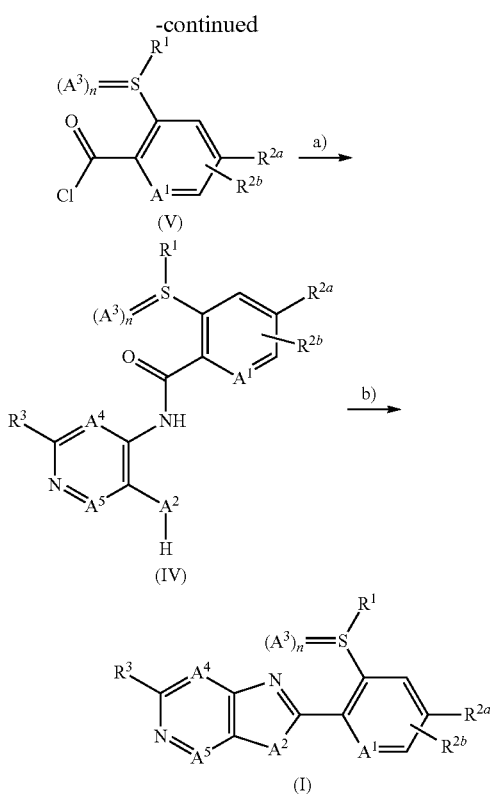

The $R^1$, $R^{2a}$, $R^{2b}$, $R^3$, $A^1$, $A^2$, $A^3$, $A^4$, $A^5$ and n radicals are each as defined above.

Step a)

In a further embodiment of the invention, compounds of the formula (IV) can be prepared by the reaction of compounds of the formula (II) with carbonyl chlorides of the formula (V) in the presence of a condensing agent.

Carbonyl chlorides of the formula (V) are either commercially available or can be prepared by known methods, for example analogously to the processes described in US2010/234603 or US2010/234604.

The reaction of the compounds of the formula (II) with carbonyl chlorides of the formula (V) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; aliphatic hydrocarbons such as hexane, heptane or octane; aromatic hydrocarbons, for example toluene or xylene; nitriles, for example acetonitrile or propionitrile; aprotic polar solvents, for example N,N-dimethylformamide or N-methylpyrrolidone, or nitrogen compounds, for example pyridine.

The reaction is preferably effected in the presence of a base. Suitable bases of the inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate. Further suitable bases are tertiary amines such as triethylamine and N,N-diisopropylethylamine, and nitrogen heterocycles such as pyridine, picoline, 2,6-lutidine, 4-dimethylaminopyridine and 1,8-diazabicyclo [5.4.0]-7-undecene (DBU).

The reaction can be effected under reduced pressure, at standard pressure or under elevated pressure and at temperatures of −20° C. to 100° C., preference being given to effecting the reaction at standard pressure and temperatures of 0° C. to 80° C.

Step b)

The further conversion of the compounds of the formula (IV) to compounds of the formula (I) is effected as in process A, step b).

Process C

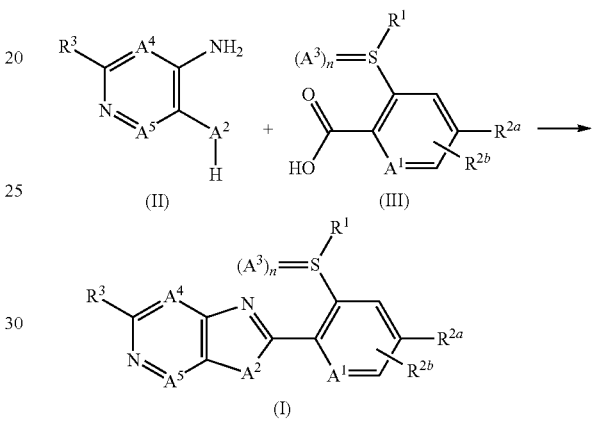

The $R^1$, $R^{2a}$, $R^{2b}$, $R^3$, $A^1$, $A^2$, $A^3$, $A^4$, $A^5$ and n radicals are each as defined above.

In a further embodiment of the invention, compounds of the formula (I) can be prepared in a one-stage process from the intermediate compounds of the formulae (II) and (III) in the presence of a condensing agent.

The conversion to compounds of the formula (I) can be effected neat or in a solvent, preference being given to conducting the reaction in a solvent selected from the customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

The reaction can be conducted in the presence of an acid or a base.

Examples of an acid which can be used in the reaction described are sulphonic acids such as methanesulphonic acid or para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

The reaction can be conducted in the presence of a suitable catalyst, for example 1-hydroxybenzotriazole.

The reaction can be conducted under reduced pressure, at standard pressure or under elevated pressure, and at temperatures of 0° C. to 200° C.

Process D

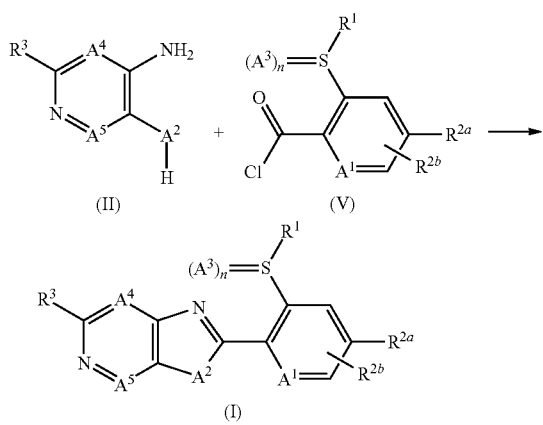

The $R^1$, $R^{2a}$, $R^{2b}$, $R^3$, $A^1$, $A^2$, $A^3$, $A^4$, $A^5$ and n radicals are each as defined above.

In a further embodiment of the invention, compounds of the formula (I) can be prepared in a one-stage process from the intermediate compounds of the formulae (II) and (V).

The conversion to compounds of the formula (I) can be effected neat or in a solvent, preference being given to conducting the reaction in a solvent selected from the customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction is preferably effected in the presence of a base. Suitable bases are inorganic bases which are typically used in such reactions. Preference is given to using bases selected by way of example from the group consisting of acetates, phosphates, hydroxides, carbonates and hydrogencarbonates of alkali metals or alkaline earth metals. Preference is given to caesium carbonate, sodium carbonate, potassium carbonate, sodium hydroxide and potassium hydroxide. Further suitable bases are tertiary amines such as triethylamine and N,N-diisopropylethylamine, nitrogen heterocycles such as pyridine, picoline, 2,6-lutidine, 4-dimethylaminopyridine and 1,8-diazabicyclo[5.4.0]-7-undecene (DBU).

The reaction can be conducted under reduced pressure, at standard pressure or under elevated pressure, and at temperatures of 0° C. to 200° C.

Process E

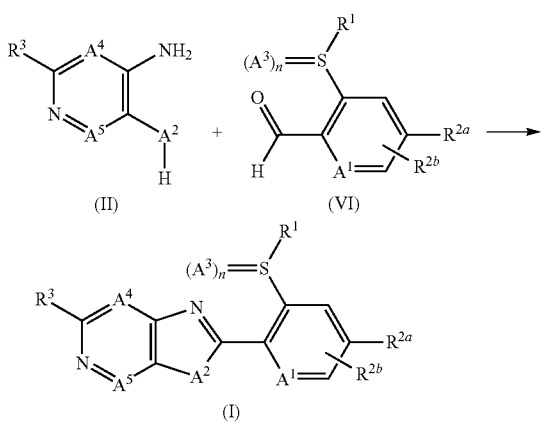

The $R^1$, $R^{2a}$, $R^{2b}$, $R^3$, $A^1$, $A^2$, $A^3$, $A^4$, $A^5$ and n radicals are each as defined above.

In a further embodiment of the invention, compounds of the formula (I) can be prepared from the compounds of the formula (II) and the aldehydes of the formula (VI) in the presence of an oxidizing agent.

Aldehydes of the formula (VI) are either commercially available or can be prepared by known methods, for example analogously to the processes described in US2009/192195, US2010/227894 or Angewandte Chemie, International Edition, 48 (2009), 7064-7068.

The conversion to compounds of the formula (I) can be effected neat or in a solvent, preference being given to conducting the reaction in a solvent. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; esters such as ethyl acetate; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be conducted in the presence of an acid. Examples of acids which can be used in the reaction described are sulphonic acids such as methanesulphonic acid or para-toluenesulphonic acid; carboxylic acids such as acetic acid, or polyphosphoric acids.

The reaction can also be conducted in the presence of a sulphite. Examples of sulphites which can be used in the reaction described are sodium hydrogensulphite or sodium sulphite.

Examples of oxidizing agents which find use in the reaction described are oxygen, copper(II) chloride or DDQ.

The reaction can be effected under reduced pressure, at standard pressure or under elevated pressure and at temperatures of 0 to 200° C., preference being given to effecting the reaction at standard pressure and temperatures of 20 to 150° C.

Process F

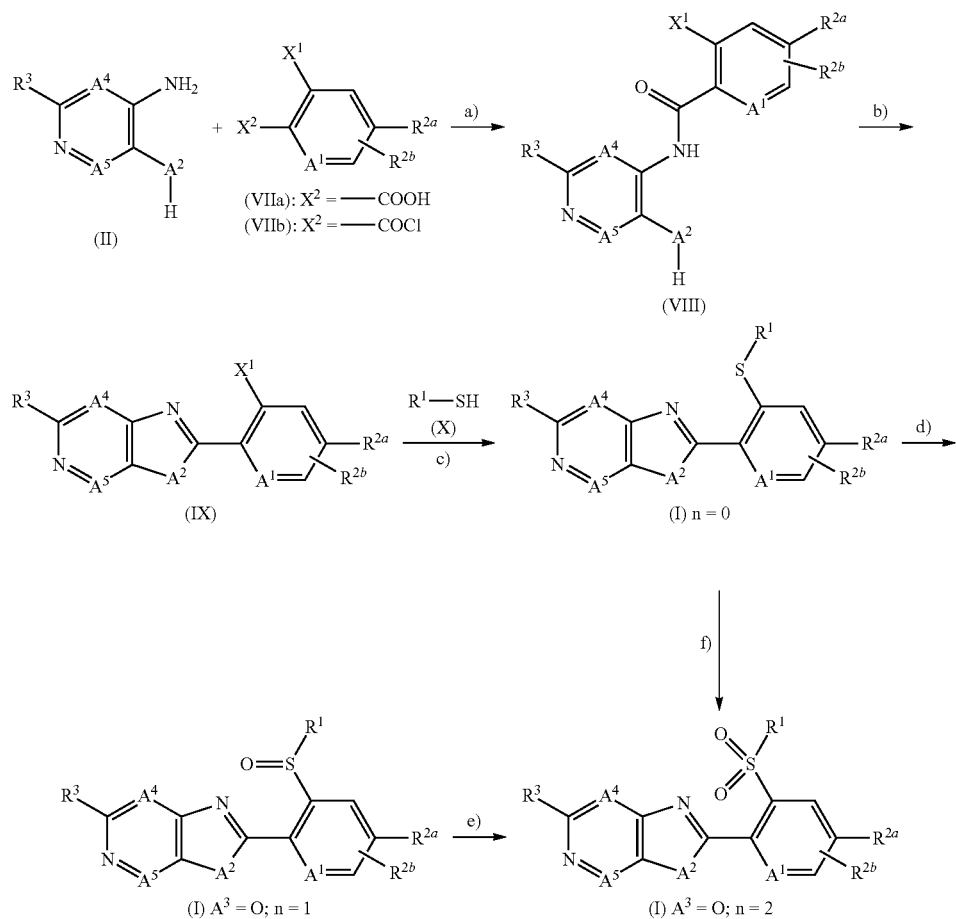

The $R^1$, $R^{2a}$, $R^{2b}$, $R^3$, $A^1$, $A^2$, $A^3$, $A^4$, $A^5$ and n radicals are each as defined above, and $X^1$ is halogen.

Step a)

The compounds of the formula (VIII) can be prepared in analogy to the process described in U.S. Pat. No. 5,576,335 by the reaction of compounds of the formula (II) with a carboxylic acid of the formula (VIIa) or with a carbonyl chloride of the formula (VIIb) in the presence of a condensing agent or a base.

Compounds of the formula (II) are either commercially available or can be prepared by known methods, for example analogously to the processes described in US2003/69257 or WO2006/65703.

Carboxylic acids of the formula (VIIa) are either commercially available or can be prepared by known methods, for example analogously to the processes described in US2010/234604, WO2012/61926 or Bioorganic and Medicinal Chemistry Letters, 18 (2008), 5023-5026.

Carbonyl chlorides of the formula (VIIb) are either commercially available or can be prepared by known methods, for example analogously to the processes described in US2010/234603 or US2010/234604.

The reaction of the compounds of the formula (II) with carboxylic acids of the formula (VIa) or carbonyl chlorides of the formula (VIIb) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be effected under reduced pressure, at standard pressure or under elevated pressure and at temperatures of 0 to 180° C., preference being given to effecting the reaction at standard pressure and temperatures of 20 to 140° C.

Step b)

The compounds of the formula (IX) can be prepared by condensing the intermediate compounds of the formula (VIII), for example analogously to the processes described in WO2012/86848.

The conversion to compounds of the formula (IX) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be conducted in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

Step c)

The compounds of the formula (I) where n is 0 can be prepared by reacting the intermediate compounds of the formula (IX) with the intermediate compounds of the formula (X) in the presence of a base.

Mercaptan derivatives of the formula (X), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (I) where n is 0 can be effected neat or in a solvent, preference being given to conducting the reaction in a solvent selected from the customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given to caesium carbonate, sodium carbonate and potassium carbonate. Further suitable bases are alkali metal hydrides, for example sodium hydride.

The reaction can be conducted under reduced pressure, at standard pressure or under elevated pressure, and at temperatures of 0° C. to 200° C.

In the reaction described, $X^1$ is preferably a fluorine or chlorine atom.

Step d)

The compounds of the formula (I) where $A^3$ is oxygen and n is 1 can be prepared by oxidizing the compounds of the formula (I) where n is 0. The oxidation is generally conducted in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (I) where $A^3$ is oxygen and n is 2 can be prepared by oxidizing the compounds of the formula (I) where $A^3$ is oxygen and n is 1. The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (I) where $A^3$ is oxygen and n is 2 can also be prepared in a one-stage process by oxidizing the compounds of the formula (I) where n is 0. The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Process G

Compounds of the formula (I) for which $R^3$=halogen can be converted to other compounds of the formula (I) for which $R^3$ is another radical according to the definition.

Compounds of the formula (I) for which $R^3$ is a C-bonded radical from the group of aryl or heteroaryl according to the definition can be prepared, for example, from compounds of the formula (I) for which $R^3$ is preferably halogen from the group of chlorine or bromine by commonly known methods (cf. *Chem. Rev.* 1995, 95, 2457-2483; *Tetrahedron* 2002, 58, 9633-9695; *Metal-Catalyzed Cross-Coupling Reactions* (eds.: A. de Meijere, F. Diederich), 2nd ed., Wiley-VCH, Weinheim, 2004).

For example, compounds in which R³ is preferably chlorine or bromine can be reacted with suitable arylboronic acids or esters thereof by known methods (cf. WO2010071819) in the presence of suitable catalysts from the group of the transition metal salts to give compounds of the formula (I) in which R³ is a radical from the group of aryl. Examples of preferred coupling catalysts include palladium catalysts such as [1,1'-bis(diphenylphosphino)ferrocene]dichloropalladium (II) or tetrakis(triphenylphosphine)palladium. Suitable basic reaction auxiliaries used to conduct the processes are preferably carbonates of sodium or potassium.

Some of the (hetero)arylboronic acids or (hetero)arylboronic esters required are known and/or commercially available, for example prepared by commonly known methods (cf. *Boronic Acids* (eds.: D. G. Hall), 2nd ed., Wiley-VCH, Weinheim, 2011).

The preparation of compounds of the formula (I) in which R³ is an N-bonded hetaryl, for example imidazol-1-yl and pyrazol-1-yl can be effected by methods known from the literature (see, for example, Journal of Organic Chemistry (2010), 69, 5578), preferably in the presence of copper(I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons. Preference is given to using toluene.

Some of the compounds of the formula (II) are novel.

Novel compounds are those of the formula (IIa)

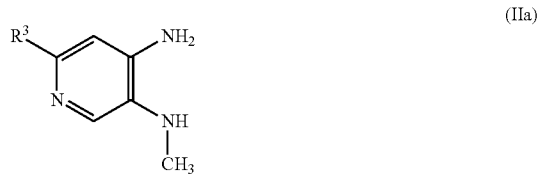

(IIa)

in which R³ is as defined above, though R³ must not be chlorine, bromine or CHO.

The present invention also provides compounds of the formula (IIa) in which R³ is (C₁-C₄)haloalkyl, (C₁-C₄)haloalkoxy, (C₁-C₄)haloalkylthio, (C₁-C₄)haloalkylsulphinyl or (C₁-C₄)haloalkylsulphonyl, where R³ is not CF₃ or CHF₂.

Preferably, R³ is CH₂F, C₂H₄F, C₂H₃F₂, C₂H₂F₃, C₂HF₄, C₂F₅, n-C₃F₇, i-C₃F₇, OCH₂F, SCH₂F, SOCH₂F, SO₂CH₂F, OCHF₂, SCHF₂, SOCHF₂, SO₂CHF₂, OCF₃, OCF₂Cl, OCFCl₂, SCF₃, SOCF₃, SO₂CF₃, OC₂H₄F, SC₂H₄F, SOC₂H₄F, SO₂C₂H₄F, OC₂H₃F₂, SC₂H₃F₂, SOC₂H₃F₂, SO₂C₂H₃F₂, OC₂H₂F₃, SC₂H₂F₃, SOC₂H₂F₃, SO₂C₂H₂F₃, OC₂HF₄, SC₂HF₄, SOC₂HF₄, SO₂C₂HF₄, OC₂F₅, SC₂F₅, SOC₂F₅, SO₂C₂F₅, n-OC₃F₇, n-SC₃F₇, n-SOC₃F₇, n-SO₂C₃F₇, i-OC₃F₇, i-SC₃F₇, i-SOC₃F₇ or i-SO₂C₃F₇.

More preferably, R³ is CH₂F, OCF₃, C₂H₄F, C₂H₃F₂, C₂H₂F₃, C₂HF₄, C₂F₅, SCF₃, SOCF₃ or SO₂CF₃.

Most preferably, R³ is C₂F₅.

Process H

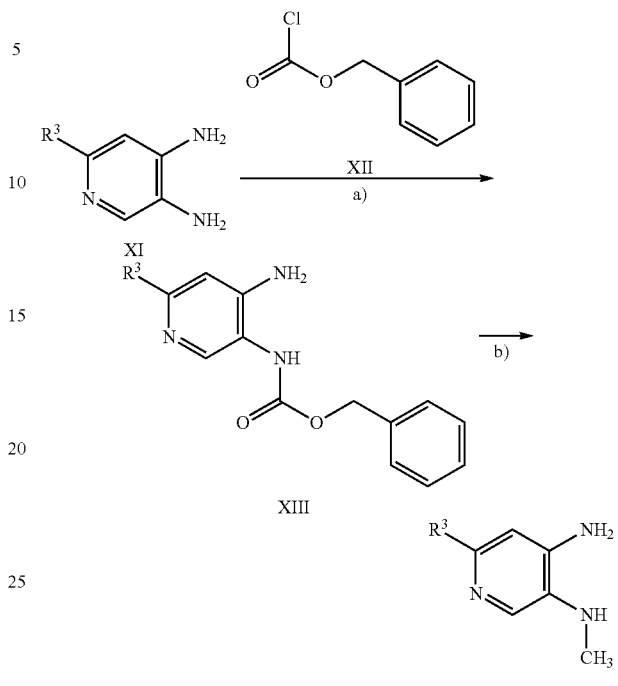

The R³ radical is as defined above.

Step a)

The compounds of the formula (XIII) can be prepared in analogy to the process described in WO2005/55928 or Journal of Medicinal Chemistry, 48 (2005), p. 6128-6139, by the reaction of compounds of the formula (XI) with benzyl chlorocarbonate (benzyl chloroformate) of the formula (XII), for example in the presence of a base.

Compounds of the formula (XI) are either commercially available or can be prepared by known methods, for example analogously to the processes described in WO2012/3576, WO2007/47793 or WO2006/65703.

The conversion to compounds of the formula (XIII) can be effected in substance or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile or aromatic hydrocarbons, for example toluene or xylene.

Examples of suitable bases are inorganic bases from the group consisting of acetates, phosphates and carbonates of alkali metals or alkaline earth metals. Preference is given to caesium carbonate, sodium carbonate and potassium carbonate.

The reaction can be conducted under reduced pressure, at standard pressure or under elevated pressure, and at temperatures of 0° C. to 120° C.

Step b)

The compounds of the formula (IIa) can be prepared by reducing the compounds of the formula (XIII), for example analogously to the processes described in Journal of Heterocyclic Chemistry, 22 (1985), p. 313-318.

An example of a suitable reducing agent is lithium aluminium hydride.

The conversion to compounds of the formula (IIa) can be effected neat or in a solvent, preference being given to conducting the reaction in a solvent selected from customary solvents that are inert under the prevailing reaction conditions. Preference is given to ethers, for example diethyl ether, diisopropyl ether, dioxane, tetrahydrofuran, 1,2-dimethoxyethane or tert-butyl methyl ether.

The reaction can be conducted under reduced pressure, at standard pressure or under elevated pressure, and at temperatures of 0° C. to 100° C.

Also novel is the compound of the formula (II-02)

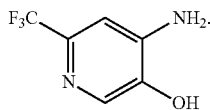

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" in each case also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro*, *Aceria kuko*, *Aceria sheldoni*, *Aculops* spp., *Aculus* spp., for example *Aculus fockeui*, *Aculus schlechtendali*, *Amblyomma* spp., *Amphitetranychus viennensis*, *Argas* spp., *Boophilus* spp., *Brevipalpus* spp., for example *Brevipalpus phoenicis*, *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., for example *Eotetranychus hicoriae*, *Epitrimerus pyri*, *Eutetranychus* spp., for example *Eutetranychus banksi*, *Eriophyes* spp., for example *Eriophyes pyri*, *Glycyphagus domesticus*, *Halotydeus destructor*, *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., for example *Oligonychus coniferarum*, *Oligonychus ilicis*, *Oligonychus indicus*, *Oligonychus man-*

*giferus*, *Oligonychus pratensis*, *Oligonychus punicae*, *Oligonychus yothersi*, *Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., for example *Tarsonemus confusus*, *Tarsonemus pallidus*, *Tetranychus* spp., for example *Tetranychus canadensis*, *Tetranychus cinnabarinus*, *Tetranychus turkestani*, *Tetranychus urticae*, *Trombicula alfreddugesi*, *Vaejovis* spp., *Vasates lycopersici*;

from the class of the Chilopoda, for example *Geophilus* spp., *Scutigera* spp.;

from the order or the class of the Collembola, for example *Onychiurus armatus*; *Sminthurus viridis*;

from the class of the Diplopoda, for example *Blaniulus guttulatus*;

from the class of the Insecta, for example from the order of the Blattodea, for example *Blatta orientalis*, *Blattella asahinai*, *Blattella germanica*, *Leucophaea maderae*, *Panchlora* spp., *Parcoblatta* spp., *Periplaneta* spp., for example *Periplaneta americana*, *Periplaneta australasiae*, *Supella longipalpa*;

from the order of the Coleoptera, for example *Acalymma vittatum*, *Acanthoscelides obtectus*, *Adoretus* spp., *Agelastica alni*, *Agriotes* spp., for example *Agriotes linneatus*, *Agriotes mancus*, *Alphitobius diaperinus*, *Amphimallon solstitialis*, *Anobium punctatum*, *Anoplophora* spp., *Anthonomus* spp., for example *Anthonomus grandis*, *Anthrenus* spp., *Apion* spp., *Apogonia* spp., *Atomaria* spp., for example *Atomaria linearis*, *Attagenus* spp., *Baris caerulescens*, *Bruchidius obtectus*, *Bruchus* spp., for example *Bruchus pisorum*, *Bruchus rufimanus*, *Cassida* spp., *Cerotoma trifurcata*, *Ceutorrhynchus* spp., for example *Ceutorrhynchus assimilis*, *Ceutorrhynchus quadridens*, *Ceutorrhynchus rapae*, *Chaetocnema* spp., for example *Chaetocnema confinis*, *Chaetocnema denticulata*, *Chaetocnema ectypa*, *Cleonus mendicus*, *Conoderus* spp., *Cosmopolites* spp., for example *Cosmopolites sordidus*, *Costelytra zealandica*, *Ctenicera* spp., *Curculio* spp., for example *Curculio caryae*, *Curculio caryatrypes*, *Curculio obtusus*, *Curculio sayi*, *Cryptolestes ferrugineus*, *Cryptolestes pusillus*, *Cryptorhynchus lapathi*, *Cryptorhynchus mangiferae*, *Cylindrocopturus* spp., *Cylindrocopturus adspersus*, *Cylindrocopturus furnissi*, *Dermestes* spp., *Diabrotica* spp., for example *Diabrotica balteata*, *Diabrotica barberi*, *Diabrotica undecimpunctata howardi*, *Diabrotica undecimpunctata undecimpunctata*, *Diabrotica virgifera virgifera*, *Diabrotica virgifera zeae*, *Dichocrocis* spp., *Dicladispa armigera*, *Diloboderus* spp., *Epilachna* spp., for example *Epilachna borealis*, *Epilachna varivestis*, *Epitrix* spp., for example *Epitrix cucumeris*, *Epitrix fuscula*, *Epitrix hirtipennis*, *Epitrix subcrinita*, *Epitrix tuberis*, *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., for example *Hypothenemus hampei*, *Hypothenemus obscurus*, *Hypothenemus pubescens*, *Lachnosterna consanguinea*, *Lasioderma serricorne*, *Latheticus oryzae*, *Lathridius* spp., *Lema* spp., *Leptinotarsa decemlineata*, *Leucoptera* spp., for example *Leucoptera coffeella*, *Lissorhoptrus oryzophilus*, *Lixus* spp., *Luperomorpha xanthodera*, *Luperodes* spp., *Lyctus* spp., *Megascelis* spp., *Melanotus* spp., for example *Melanotus longulus oregonensis*, *Meligethes aeneus*, *Melolontha* spp., for example *Melolontha melolon-*

*tha*, *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorhynchus* spp., for example *Otiorhynchus cribricollis*, *Otiorhynchus ligustici*, *Otiorhynchus ovatus*, *Otiorhynchus rugosostriarus*, *Otiorhynchus sulcatus*, *Oxycetonia jucunda*, *Phaedon cochleariae*, *Phyllophaga* spp., *Phyllophaga helleri*, *Phyllotreta* spp., for example *Phyllotreta armoraciae*, *Phyllotreta pusilla*, *Phyllotreta ramosa*, *Phyllotreta striolata*, *Popillia japonica*, *Premnotrypes* spp., *Prostephanus truncatus*, *Psylliodes* spp., for example *Psylliodes affinis*, *Psylliodes chrysocephala*, *Psylliodes punctulata*, *Ptinus* spp., *Rhizobius ventralis*, *Rhizopertha dominica*, *Sitophilus* spp., for example *Sitophilus granarius*, *Sitophilus linearis*, *Sitophilus oryzae*, *Sitophilus zeamais*, *Sphenophorus* spp., *Stegobium paniceum*, *Sternechus* spp., for example *Sternechus paludatus*, *Symphyletes* spp., *Tanymecus* spp., for example *Tanymecus dilaticollis*, *Tanymecus indicus*, *Tanymecus palliatus*, *Tenebrio molitor*, *Tenebrioides mauretanicus*, *Tribolium* spp., for example *Tribolium audax*, *Tribolium castaneum*, *Tribolium confusum*, *Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti*, *Aedes albopictus*, *Aedes sticticus*, *Aedes vexans*, *Agromyza* spp., for example *Agromyza frontella*, *Agromyza parvicornis*, *Anastrepha* spp., *Anopheles* spp., for example *Anopheles quadrimaculatus*, *Anopheles gambiae*, *Asphondylia* spp., *Bactrocera* spp., for example *Bactrocera cucurbitae*, *Bactrocera dorsalis*, *Bactrocera oleae*, *Bibio hortulanus*, *Calliphora erythrocephala*, *Calliphora vicina*, *Ceratitis capitata*, *Chironomus* spp., *Chrysomya* spp., *Chrysops* spp., *Chrysozona pluvialis*, *Cochliomya* spp., *Contarinia* spp., for example *Contarinia johnsoni*, *Contarinia nasturtii*, *Contarinia pyrivora*, *Contarinia schulzi*, *Contarinia sorghicola*, *Contarinia tritici*, *Cordylobia anthropophaga*, *Cricotopus sylvestris*, *Culex* spp., for example *Culex pipiens*, *Culex quinquefasciatus*, *Culicoides* spp., *Culiseta* spp., *Cuterebra* spp., *Dacus oleae*, *Dasineura* spp., for example *Dasineura brassicae*, *Delia* spp., for example *Delia antiqua*, *Delia coarctata*, *Delia florilega*, *Delia platura*, *Delia radicum*, *Dermatobia hominis*, *Drosophila* spp., for example *Drosphila melanogaster*, *Drosophila suzukii*, *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., for example *Liriomyza brassicae*, *Liriomyza huidobrensis*, *Liriomyza sativae*, *Lucilia* spp., for example *Lucilia cuprina*, *Lutzomyia* spp., *Mansonia* spp., *Musca* spp., for example *Musca domestica*, *Musca domestica vicina*, *Oestrus* spp., *Oscinella frit*, *Paratanytarsus* spp., *Paralauterborniella subcincta*, *Pegomya* spp., for example *Pegomya betae*, *Pegomya hyoscyami*, *Pegomya rubivora*, *Phlebotomus* spp., *Phorbia* spp., *Phormia* spp., *Piophila casei*, *Prodiplosis* spp., *Psila rosae*, *Rhagoletis* spp., for example *Rhagoletis cingulata*, *Rhagoletis completa*, *Rhagoletis fausta*, *Rhagoletis indifferens*, *Rhagoletis mendax*, *Rhagoletis pomonella*, *Sarcophaga* spp., *Simulium* spp., for example *Simulium meridionale*, *Stomoxys* spp., *Tabanus* spp., *Tetanops* spp., *Tipula* spp., for example *Tipula paludosa*, *Tipula simplex*;

from the order of the Hemiptera, for example *Acizzia acaciaebaileyanae*, *Acizzia dodonaeae*, *Acizzia uncatoides*, *Acrida turrita*, *Acyrthosipon* spp., for example *Acyrthosiphon pisum*, *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., for example *Amrasca bigutulla*, *Amrasca devastans*, *Anuraphis cardui*, *Aonidiella* spp., for example *Aonidiella aurantii*, *Aonidiella citrina*, *Aonidiella inornata*, *Aphanostigma piri*, *Aphis* spp., for example *Aphis citricola*, *Aphis craccivora*, *Aphis fabae*, *Aphis forbesi*, *Aphis glycines*, *Aphis gossypii*, *Aphis hederae*, *Aphis illinoisensis*, *Aphis middletoni*, *Aphis nasturtii*, *Aphis nerii*, *Aphis pomi*, *Aphis spiraecola*, *Aphis viburniphila*, *Arboridia apicalis*, *Arytainilla* spp., *Aspidiella* spp., *Aspidiotus* spp., for example *Aspidiotus nerii*, *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., for example *Cacopsylla pyricola*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., for example *Coccus hesperidum*, *Coccus longulus*, *Coccus pseudomagnoliarum*, *Coccus viridis*, *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., for example *Dysaphis apiifolia*, *Dysaphis plantaginea*, *Dysaphis tulipae*, *Dysmicoccus* spp., *Empoasca* spp., for example *Empoasca abrupta*, *Empoasca fabae*, *Empoasca maligna*, *Empoasca solana*, *Empoasca stevensi*, *Eriosoma* spp., for example *Eriosoma americanum*, *Eriosoma lanigerum*, *Eriosoma pyricola*, *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., for example *Icerya purchasi*, *Idiocerus* spp., *Idioscopus* spp., *Laodelphax striatellus*, *Lecanium* spp., for example *Lecanium corni* (=*Parthenolecanium corni*), *Lepidosaphes* spp., for example *Lepidosaphes ulmi*, *Lipaphis erysimi*, *Macrosiphum* spp., for example *Macrosiphum euphorbiae*, *Macrosiphum lilii*, *Macrosiphum rosae*, *Macrosteles facifrons*, *Mahanarva* spp., *Melanaphis sacchari*, *Metcalfiella* spp., *Metcalfa pruinosa*, *Metopolophium dirhodum*, *Monellia costalis*, *Monelliopsis pecanis*, *Myzus* spp., for example *Myzus ascalonicus*, *Myzus cerasi*, *Myzus ligustri*, *Myzus ornatus*, *Myzus persicae*, *Myzus nicotianae*, *Nasonovia ribisnigri*, *Nephotettix* spp., for example *Nephotettix cincticeps*, *Nephotettix nigropictus*, *Nilaparvata lugens*, *Oncometopia* spp., *Orthezia praelonga*, *Oxya chinensis*, *Pachypsylla* spp., *Parabemisia myricae*, *Paratrioza* spp., for example *Paratrioza cockerelli*, *Parlatoria* spp., *Pemphigus* spp., for example *Pemphigus bursarius*, *Pemphigus populivenae*, *Peregrinus maidis*, *Phenacoccus* spp., for example *Phenacoccus madeirensis*, *Phloeomyzus passerinii*, *Phorodon humuli*, *Phylloxera* spp., for example *Phylloxera devastatrix*, *Phylloxera notabilis*, *Pinnaspis aspidistrae*, *Planococcus* spp., for example *Planococcus citri*, *Prosopidopsylla flava*, *Protopulvinaria pyriformis*, *Pseudaulacaspis pentagona*, *Pseudococcus* spp., for example *Pseudococcus calceolariae*, *Pseudococcus comstocki*, *Pseudococcus longispinus*, *Pseudococcus maritimus*, *Pseudococcus viburni*, *Psyllopsis* spp., *Psylla* spp., for example *Psylla buxi*, *Psylla mali*, *Psylla pyri*, *Pteromalus* spp., *Pyrilla* spp., *Quadraspidiotus* spp., for example *Quadraspidiotus juglansregiae*, *Quadraspidiotus ostreaeformis*, *Quadraspidiotus perniciosus*, *Quesada gigas*, *Rastrococcus* spp., *Rhopalosiphum* spp., for example *Rhopalosiphum maidis*, *Rhopalosiphum oxyacanthae*, *Rhopalosiphum padi*, *Rhopalosiphum rufiabdominale*, *Saissetia* spp., for example *Saissetia coffeae*, *Saissetia miranda*, *Saissetia neglecta*,

*Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracilaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter cratagella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Anion* spp., for example *Anion ater rufus*, *Biomphalaria* spp., *Bulinus* spp., *Deroceras* spp., for example *Deroceras laeve*, *Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active ingredients.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers 173, prepared by the FAO/WHO Joint Meeting on Pesticide Specifications, 2004, ISBN: 9251048576. The formulations, in addition to one or more compounds of the formula (I), optionally comprise further agrochemically active ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which improves the biological activity of the formulation without having biological activity itself. Examples of adjuvants are agents which promote retention, the spreading characteristics, adhesion to the leaf surface or penetration.

These formulations are prepared in a known way, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be such substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

In principle, it is possible to use any suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under standard pressure, for example aerosol propellants such as halohydrocarbons, or else butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

In addition, stabilizers, such as low-temperature stabilizers, preservatives, antioxidants, light stabilizers or other agents which improve chemical and/or physical stability, may be present. In addition, foam formers or defoamers may be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, yet further auxiliaries may be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence increase the mobility of active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), with particular preference between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Insecticides/Acaricides/Nematicides

The active ingredients specified here with their "common names" are known and are described for example in The Pesticide Manual, 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active ingredients with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active ingredients, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active ingredients specified herein by their common name are known and described, for example, in the "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazol, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl] phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity, for example (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxy chloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copper-oxine, (5.28) propamidine, (5.29) propineb, (5.30) sulphur and sulphur preparations, for example calcium poly sulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin.

(7) Amino acid and protein biosynthesis inhibitors, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors, for example (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4)

fthalide, (11.5) pyroquilon, (11.6) tricyclazole and (11.7) 2,2,2-trifluoroethyl {3-methyl-1-[(4-methylbenzoyl)amino] butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds, for example (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl) prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R, 8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazol-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl) ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl) thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl] oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{ (E)-[(cyclopropylmethoxy)imino][6-(difluoromethoxy)-2, 3-difluorophenyl]methyl}-2-phenylacetamide, (15.85) N—{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylie acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl) oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-

(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, especially strain ATCC 74040, *Coniothyrium minitans*, especially strain CON/M/91-8 (Accession No. DSM-9660), *Lecanicillium* spp., especially strain HRO LEC 12, *Lecanicillium lecanii*, (formerly known as *Verticillium lecanii*), especially strain KV01, *Metarhizium anisopliae*, especially strain F52 (DSM3884/ATCC 90448), *Metschnikowia fructicola*, especially strain NRRL Y-30752, *Paecilomyces fumosoroseus* (now: *Isaria fumosorosea*), especially strain IFPC 200613, or strain Apopka 97 (Accesion No. ATCC 20874), *Paecilomyces lilacinus*, especially *P. lilacinus* strain 251 (AGAL 89/030550), *Talaromyces flavus*, especially strain V117b, *Trichoderma atroviride*, especially strain SC1 (Accession Number CBS 122089), *Trichoderma harzianum*, especially *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Sullins* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, Dryopteris filix-mas, *Equisetum arvense*, Fortune Aza, Fungastop, Heads Up (*Chenopodium quinoa* saponin extract), pyrethrum/pyrethrins, *Quassia amara, Quercus, Quillaja, Regalia*, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and parts of plants can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active ingredients, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed gives rise to a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The inventive method for protecting seed and germinating plants against attack by pests further comprises a method in which the seed is treated simultaneously in one operation or sequentially with a compound of the formula (I) and a mixing component. It also further comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occurs when one of the compounds of the formula (I) acts systemically is that the treatment of the seed protects not just the seed itself but also the plants resulting therefrom after emergence against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

In addition, compounds of the formula (I) can be used in combination with signalling technology compositions, which results in better colonization by symbionts, for example *rhizobia*, mycorrhizae and/or endophytic bacteria or fungi, and/or leads to optimized nitrogen fixation.

The compounds of the formula (I) are suitable for protection of seed of any plant variety which is used in agriculture, in greenhouses, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus*, *Rhizobium*, *Pseudomonas*, *Serratia*, *Trichoderma*, *Clavibacter*, *Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which, for example, has been pre-swollen in water up to a particular stage (pigeon breast stage), which leads to better germination and to more homogeneous emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are produced in a known manner, by mixing the compounds of the formula (I) with customary additives, for example customary extenders and solvents or diluents, dyes, wetters, dispersants, emulsifiers, antifoams, preservatives, secondary thickeners, stickers, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are customary for the formulation of active agrochemical ingredients. Preference is given to using alkyl naphthalenesulphonates, such as diisopropyl or diisobutyl naphthalenesulphonates.

Suitable dispersants and/or emulsifiers which may be present in the seed dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Aty lotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:
from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus (Boophilus)* spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa include:
Mastigophora (*Flagellata*), for example Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example, *Giardia lamblia*, *G. canis*;

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I. spec.*, *I. suis*, *Cystisospora* spec., *Cryptosporidium* spec., in particular *C. parvum*; such as Toxoplasmadidae, for example, *Toxoplasma gondii*, *Hammondia heydornii*, *Neospora caninum*, *Besnoitia besnoitii*; such as Sarcocystidae, for example, *Sarcocystis bovicanis*, *S. bovihominis*, *S. ovicanis*, *S. ovifelis*, *S. neurona*, *S. spec.*, *S. suihominis*, such as Leucozoidae, for example, *Leucozytozoon simondi*, such as Plasmodiidae, for example, *Plasmodium berghei*, *P. falciparum*, *P. malariae*, *P. ovale*, *P. vivax*, *P. spec.*, such as Piroplasmea, for example, *Babesia argentina*, *B. bovis*, *B. canis*, *B. spec.*, *Theileria parva*, *Theileria spec.*, such as Adeleina, for example, *Hepatozoon canis*, *H. spec.*

Pathogenic endoparasites, which are helminths, include Platyhelmintha (e.g. Monogenea, cestodes and trematodes), roundworms, Acanthocephala, and Pentastoma. These include:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diphlogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thy saniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

nematodes: Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cy stocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as medicament.

A further aspect refers to the use of a compound of the formula (I) as an antiendoparasitic agent, in particular as a helminthicidal agent or antiprotozoic agent. Compounds of the formula (I) are suitable for use as an antiendoparasitic agent, especially as a helminthicidal agent or antiprotozoic agent, for example in animal husbandry, in animal breeding, in buildings for livestock and in the hygiene sector.

A further aspect in turn relates to the use of a compound of the formula (I) as an antiectoparasitic agent, especially an arthropodicide such as an insecticide or an acaricide. A further aspect relates to the use of a compound of the formula (I) as an antiectoparasitic agent, especially an arthropodicide such as an insecticide or an acaricide, for example in animal husbandry, in animal breeding, in buildings for livestock or in the hygiene sector.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, filariasis, other viral diseases, transmission of worms;

*Aedes*: yellow fever, dengue fever, filariasis, other viral diseases;

Simuliidae: transmission of worms, in particular *Onchocerca volvulus*;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), CrimeanCongo haemorrhagic fever, borreliosis;

6) Ticks: borellioses such as *Borrelia duttoni*, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Preparation Example 1: 3-Methyl-2-[3-(methylsulphonyl)-5-(trifluoromethyl)pyridin-2-yl]-6-(trifluoromethyl)-3H-imidazo[4,5-c]pyridine (I-36)

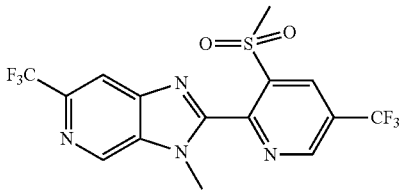 [SMILES: Cn1c(-c2ncc(C(F)(F)F)cc2S(C)(=O)=O)nc2cc(C(F)(F)F)ncc21]

41 mg (0.10 mmol) of 3-methyl-2-[3-(methylsulphanyl)-5-(trifluoromethyl)pyridin-2-yl]-6-(trifluoromethyl)-3H-imidazo[4,5-c]pyridine are dissolved in 4 ml of dichloromethane, 86.5 mg (0.36 mmol) of meta-chloroperbenzoic acid are added at 0° C. and then the mixture is stirred at room temperature for 20 h. The mixture is admixed with sodium bisulphite solution, stirred for 10 min, diluted with 30 ml of water and adjusted to pH 9-10 with 45% sodium hydroxide solution. The mixture is extracted three times with dichloromethane and then the combined organic phases are freed of the solvent under reduced pressure.

(log P (neutral): 2.64; MH$^+$: 425; $^1$H NMR (400 MHz, D$_6$-DMSO) δ ppm: 3.70 (s, 3H), 3.93 (s, 3H), 8.35 (s, 1H), 8.83 (s, 1H), 9.32 (s, 1H), 9.58 (s, 1H).

Preparation of 3-methyl-2-[3-(methylsulphinyl)-5-(trifluoromethyl)pyridin-2-yl]-6-(trifluoro-methyl)-3H-imidazo[4,5-c]pyridine (I-26)

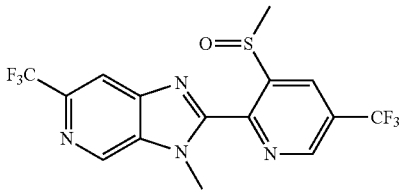 [SMILES: Cn1c(-c2ncc(C(F)(F)F)cc2S(C)=O)nc2cc(C(F)(F)F)ncc21]

41 mg (0.10 mmol) of 3-methyl-2-[3-(methylsulphanyl)-5-(trifluoromethyl)pyridin-2-yl]-6-(trifluoromethyl)-3H-imidazo[4,5-c]pyridine are dissolved in 4 ml of dichloromethane, and 1.92 mg (0.04 mmol) of formic acid and 28.44 mg of a 35% hydrogen peroxide solution are added at room temperature. The mixture is stirred at room temperature for 5 h, sodium bisulphite solution is added and the mixture is stirred for a further 3 h. Subsequently, the mixture is stirred with 10% sodium hydrogencarbonate solution, the organic phase is removed, the aqueous phase is extracted twice with dichloromethane, and the organic phases are combined and then freed of the solvent under reduced pressure.

(log P (neutral): 2.76; MH$^+$: 409; $^1$H NMR (400 MHz, D$_6$-DMSO) δ ppm: 3.15 (s, 3H), 4.35 (s, 3H), 8.37 (s, 1H), 8.85 (s, 1H), 9.37 (s, 1H), 9.39 (s, 1H).

Preparation of 3-methyl-2-[3-(methylsulphanyl)-5-(trifluoromethyl)pyridin-2-yl]-6-(trifluoro-methyl)-3H-imidazo[4,5-c]pyridine (I-3)

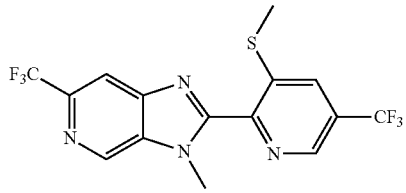 [SMILES: CSc1cc(C(F)(F)F)cnc1-c1nc2cc(C(F)(F)F)ncc2n1C]

150 mg (0.39 mmol) of 2-[3-chloro-5-(trifluoromethyl)pyridin-2-yl]-3-methyl-6-(trifluoromethyl)-3H-imidazo[4,5-c]pyridine and 83 mg (1.18 mmol) of sodium methanethiolate are stirred in DMF at room temperature for 6 h. The mixture is admixed with water and extracted three times with ethyl acetate. The combined organic phases are washed with a sodium chloride solution, removed, dried over sodium sulphate and freed of the solvent under reduced pressure.

(log P (neutral): 3.16; MH$^+$: 393; $^1$H NMR (400 MHz, D$_6$-DMSO) δ ppm: 2.58 (s, 3H), 4.06 (s, 3H), 8.27 (s, 1H), 8.32 (s, 1H), 8.95 (s, 1H), 9.29 (s, 1H).

Preparation of 2-[3-chloro-5-(trifluoromethyl)pyridin-2-yl]-3-methyl-6-(trifluoromethyl)-3H-imidazo[4,5-c]pyridine (IX-01)

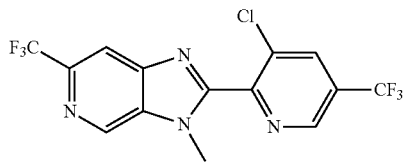 [SMILES: Cn1c(-c2ncc(C(F)(F)F)cc2Cl)nc2cc(C(F)(F)F)ncc21]

950 mg (4.97 mmol) of N$^3$-methyl-6-(trifluoromethyl)pyridine-3,4-diamine (II-01), 1.12 g (4.97 mmol) of 3-chloro-5-(trifluoromethyl)pyridine-2-carboxylic acid and 953 mg (4.97 mmol) of 1-(3-dimethylaminopropyl)-3-ethylcarbodiimide hydrochloride (EDCI) are stirred in 10 ml of pyridine at 115° C. for 7 h. The reaction mixture is freed of solvent under reduced pressure, then water is added and the mixture is extracted three times with ethyl acetate. The combined organic phases are dried over sodium sulphate, concentrated again and purified by column chromatography purification by means of preparative HPLC with a water/acetonitrile gradient as eluent.

(log P (neutral): 2.96; MH$^+$: 381; $^1$H NMR (400 MHz, D$_6$-DMSO) δ ppm: 4.00 (s, 3H), 8.35 (s, 1H), 8.86 (s, 1H), 9.22 (s, 1H), 9.30 (s, 1H).

Preparation of 3-chloro-N-[5-(methylamino)-2-(trifluoromethyl)pyridin-4-yl]-5-(trifluoromethyl)pyridine-2-carboxamide (VIII-01)

By the above method for preparation of 2-[3-chloro-5-(trifluoromethyl)pyridin-2-yl]-3-methyl-6-(trifluoromethyl)-3H-imidazo[4,5-c]pyridine (IX-01) from N$^3$-methyl-6-(trifluoromethyl)pyridine-3,4-diamine (II-01) and 3-chloro-5-(trifluoromethyl)pyridine-2-carboxylic acid, it is likewise possible to prepare the compound 3-chloro-N-[5-(methylamino)-2-(trifluoromethyl)pyridin-4-yl]-5-(trifluoromethyl)pyridine-2-carboxamide (VIII-01) as an intermediate for the compound (IX-01).

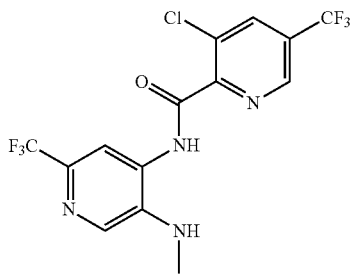 [SMILES: CNc1cnc(C(F)(F)F)cc1NC(=O)c1ncc(C(F)(F)F)cc1Cl]

(log P (neutral): 3.09; MH$^+$: 399; $^1$H NMR (400 MHz, D$_6$-DMSO) δ ppm: 2.87 (d, 3H), 5.97 (q, 1H), 8.10 (s, 1H), 8.18 (s, 1H), 8.73 (s, 1H), 9.09 (s, 1H), 10.40 (br. S, 1H).

Preparation of N$^3$-methyl-6-(trifluoromethyl)pyridine-3,4-diamine (II-01)

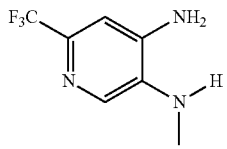

A solution of 0.93 g (3.0 mmol) of benzyl[4-amino-6-(trifluoromethyl)pyridin-3-yl]carbamate in 85 ml of tetrahydrofuran is cooled to 0° C. and admixed with 0.65 g (17 mmol) of lithium aluminium hydride. The mixture is stirred under argon at 0° C. for 15 min and then at room temperature for 4 h. The excess of lithium aluminium hydride is destroyed by the addition of ethyl acetate, the mixture is filtered and the filtrate is extracted twice with 50 ml each time of 2 N hydrochloric acid. The combined hydrochloric acid extracts are adjusted to pH=8 with sodium carbonate while cooling. Subsequently, the mixture is extracted twice with 100 ml each time of ethyl acetate, the organic phases are combined and dried with sodium sulphate, and the solvent is distilled off under reduced pressure. The product is purified further by recrystallization from a mixture of hexane/isopropanol.

(MH$^+$: 192; $^1$H NMR (400 MHz, D$_6$-DMSO) δ ppm: 2.81 (d, 3H), 5.22 (q, 1H), 5.82 (br. s, 2H), 6.84 (s, 1H), 7.57 (s, 1H).

Preparation of benzyl[4-amino-6-(trifluoromethyl)pyridin-3-yl]carbamate

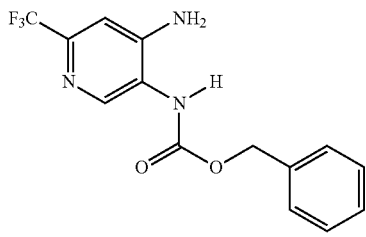 [SMILES: Nc1cc(C(F)(F)F)ncc1NC(=O)OCc1ccccc1]

0.91 g of 6-(trifluoromethyl)pyridine-3,4-diamine is dissolved in a mixture of 20 ml of tetrahydrofuran and 2 ml of pyridine. A solution of 1.07 g (6.3 mmol) of benzyl chlorocarbonate (benzyl chloroformate) in 2 ml of tetrahydrofuran is added dropwise while stirring. Subsequently, the reaction mixture is stirred overnight, diluted with 100 ml of water and extracted twice with 100 ml each time of ethyl acetate. The combined organic phases are washed with 50 ml of water, dried over sodium sulphate and concentrated. By washing the residue with 50 ml of chloroform, the product is obtained in the form of a white solid.

($^1$H NMR (500 MHz, D$_6$-DMSO) δ ppm: 5.15 (s, 2H), 6.40 (br. s 2H), 7.05 (s, 1H), 7.30-7.45 (m, 5H), 8.35 (s, 1H), 9.00 (br. s, 1H).

Preparation Example 2: 2-[2-(Ethylsulphanyl)phenyl]-6-(trifluoromethyl)[1,3]oxazolo[5,4-c]pyridine (I-35)

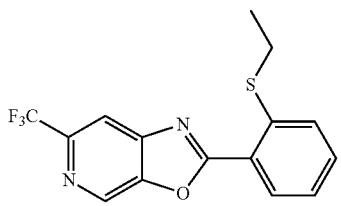 [SMILES: CCSc1ccccc1-c1nc2cc(C(F)(F)F)ncc2o1]

400 mg (1.16 mmol) of 2-(ethylsulphanyl)-N-[5-hydroxy-2-(trifluoromethyl)pyridin-4-yl]benzamide and 398 mg (1.51 mmol) of triphenylphosphine are dissolved in 12 ml of THF, and 661 mg (1.51 mmol) of 40% diethyl azodicarboxylate (DEAD) in toluene are added dropwise at RT. The mixture is stirred at room temperature for 3 h. Subsequently, the solvent is distilled off under reduced pressure and the residue is purified by column chromatography purification with a water/acetonitrile gradient as eluent.

(log P (neutral): 4.07; MH$^+$: 325; $^1$H NMR (400 MHz, D$_6$-DMSO) δ ppm: 1.32 (t, 3H), 3.10 (q, 2H), 7.42 (t, 1H), 7.60-7.69 (m, 2H), 8.21 (d, 1H), 8.54 (s, 1H), 9.33 (s, 1H).

Preparation of 2-(ethylsulphanyl)-N-[5-hydroxy-2-(trifluoromethyl)pyridin-4-yl]benzamide (VIII-02)

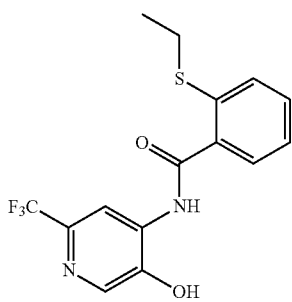 [SMILES: CCSc1ccccc1C(=O)Nc1cc(C(F)(F)F)ncc1O]

206 mg (1.12 mmol) of 2-(ethylsulphanyl)benzoic acid and 201 mg (1.12 mmol) of 4-amino-6-(trifluoromethyl)pyridin-3-ol are dissolved in 5 ml of pyridine, 325 mg (1.69 mmol) of 1-(3-dimethylaminopropyl)-3-ethylcarbodiimide hydrochloride (EDCI) are added and the mixture is stirred at 50° C. for 2 h and at 80° C. for 3 h. The solvent is distilled off under reduced pressure, and the residue is taken up in water and extracted with ethyl acetate. The organic phase is washed with a sodium chloride solution, removed, dried over sodium sulphate and concentrated. The residue is purified by column chromatography purification by means of preparative HPLC with a water/acetonitrile gradient as eluent.

(log P (neutral): 1.59; MH+: 343; ¹H NMR (400 MHz, D₆-DMSO) δ ppm: 1.21 (t, 3H), 2.98 (q, 2H), 7.29-7.34 (m, 1H), 7.48-7.53 (m, 2H), 7.61 (d, 1H), 8.29 (s, 1H), 8.55 (s, 1H), 9.99 (s, 1H), 11.31 (br. S, 1H).

Preparation of 4-amino-6-(trifluoromethyl)pyridin-3-ol (II-02)

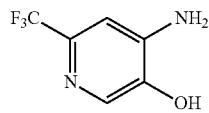

12.3 g (42.1 mmol) of tert-butyl[5-methoxy-2-(trifluoromethyl)pyridin-4-yl]carbamate are dissolved in 300 ml of dichloromethane and cooled to −78° C., and 42.2 g (168 mmol) of boron tribromide in 150 ml of dichloromethane are added dropwise at this temperature. The mixture is allowed to come to room temperature overnight, then 400 ml of sodium hydrogencarbonate solution are added and the mixture is extracted three times with 100 ml each time of dichloromethane. The solvent is distilled off and the residue is purified by chromatography on silica gel.

(¹H NMR (90 MHz, D₆-DMSO) δ ppm: 7.00 (s, 1H), 7.9 (s, 1H).

Preparation of tert-butyl[5-methoxy-2-(trifluoromethyl)pyridin-4-yl]carbamate

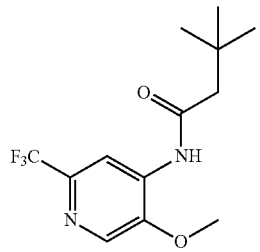 [SMILES: COc1cnc(C(F)(F)F)cc1NC(=O)CC(C)(C)C]

To a solution of 9.80 g (44.3 mmol) of 5-methoxy-2-(trifluoromethyl)isonicotinic acid in 980 ml of tert-butanol are added, at room temperature, 65 g of 4 A molecular sieve, 14.6 g (53.1 mmol) of diphenylphosphoryl azide (DPPA) and 5.37 g (53.1 mmol) of triethylamine. The reaction mixture is stirred at 81° C. for 23 h and then the 4 Å molecular sieve is filtered off. After the tert-butanol has been distilled off under reduced pressure, the residue is admixed with 500 ml of ethyl acetate, washed with 250 ml of 2 N hydrochloric acid, 250 ml of saturated aqueous sodium hydrogencarbonate solution, 250 ml of water and 250 ml of sodium chloride solution, and dried over sodium sulphate. The solvent is removed under reduced pressure and the residue is washed three times with 15 ml each time of ethyl acetate and dried under reduced pressure. The ethyl acetate phase is purified by chromatography on silica gel (hexane/EtOAc 4:1=>2:1).

(¹H NMR (90 MHz, CDCl₃) δ ppm: 1.5 (s, 9H), 4.0 (s, 3H), 8.2 (s, 1H), 8.5 (s, 1H).

Preparation of 2-[3-ethylsulphanyl-5-(trifluoromethyl)-2-pyridyl]-3-methyl-6-[4-(trifluoromethyl)phenyl]imidazo[4,5-c]pyridine (I-64)

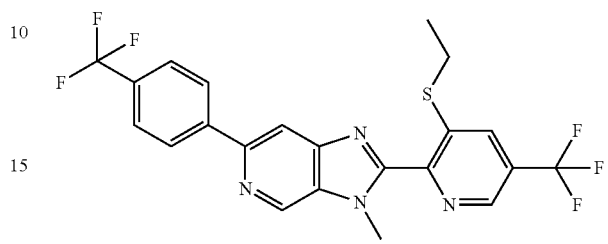

A solution of 62 mg (0.58 mmol) of sodium carbonate in 2 ml of a 4:1 mixture of 1,2-dimethoxyethane and water is degassed in an ultrasound bath, and 73 mg (0.19 mmol) of 6-chloro-2-[3-ethylsulphanyl-5-(trifluoromethyl)-2-pyridyl]-3-methylimidazo[4,5-c]pyridine and 67 mg (0.35 mmol) of [4-(trifluoromethyl)phenyl]boronic acid are added. The vessel is flooded with argon and then 23 mg (20 μmol) of tetrakis(triphenylphosphine)palladium are added. The mixture is heated in a CEM Discover microwave to 140° C. for 2 h 10 min, then admixed with a further 68 mg (59 μmol) of tetrakis(triphenylphosphine)palladium and heated to 140° C. for a further 4 h. The reaction mixture is filtered through a Celite bed which has been rinsed with ethyl acetate. After the solvent has been removed under reduced pressure, the residue is separated chromatographically by MPLC on silica gel (gradient: ethyl acetate/cyclohexane). This is followed by another chromatographic separation by means of preparative HPLC (gradient: H₂O/acetonitrile). In this way, 14 mg (99% purity, 15% yield) of 2-[3-ethylsulphanyl-5-(trifluoromethyl)-2-pyridyl]-3-methyl-6-[4-(trifluoromethyl)phenyl]imidazo[4,5-c]pyridine are obtained.

(log P (neutral): 3.95; MH+: 483; ¹H NMR (400 MHz, D₆-DMSO) δ ppm: 9.275 (2.6); 9.271 (2.5); 8.943 (4.3); 8.584 (2.6); 8.580 (2.6); 8.318 (0.5); 7.701 (3.0); 7.680 (3.9); 7.548 (3.8); 7.527 (3.0); 7.410 (4.6); 3.890 (16.0); 3.329 (75.4); 3.140 (1.3); 3.122 (4.2); 3.104 (4.3); 3.086 (1.4); 2.676 (0.9); 2.671 (1.2); 2.667 (0.9); 2.507 (140.3); 2.502 (179.9); 2.498 (134.5); 2.334 (0.9); 2.329 (1.2); 2.325 (0.9); 1.281 (4.6); 1.263 (9.7); 1.245 (4.5); 0.146 (0.4); 0.008 (3.6); 0.000 (84.0); −0.150 (0.4).

Preparation of 2-[3-ethylsulphanyl-5-(trifluoromethyl)-2-pyridyl]-3-methyl-6-[4-(trifluoromethyl)-imidazol-1-yl]imidazo[4,5-c]pyridine (I-74)

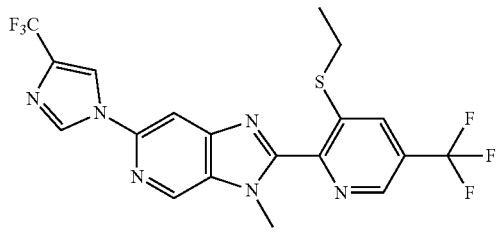 [SMILES: CCSc1cc(C(F)(F)F)cnc1-c1nc2cc(-n3cnc(C(F)(F)F)c3)ncc2n1C]

Under argon, 99 mg (0.27 mmol) of 6-chloro-2-[3-ethylsulphanyl-5-(trifluoromethyl)-2-pyridyl]-3-methylimidazo[4,5-c]pyridine, 23 μl (0.15 mmol) of trans-N,N'-dimethylcyclohexane-1,2-diamine, 6.8 mg (36 μmop of copper(I) iodide, 30 mg (0.22 mmol) of 4-(trifluoromethyl)-1H-imidazole and 64 mg (0.46 mmol) of potassium carbonate are added to 1 ml of degassed toluene. The vessel is closed and the reaction mixture is heated in a CEM Discover microwave reactor to 110° C. for 4 h. After cooling to room temperature, ethyl acetate is added and the mixture is filtered through a Celite bed, which is subsequently rinsed with ethyl acetate. The solvent is removed under reduced pressure and the residue is separated chromatographically by MPLC on silica gel (gradient: ethyl acetate/cyclohexane). In this way, 22 mg (100% purity, 18% yield) of 2-[3-ethylsulphanyl-5-(trifluoromethyl)-2-pyridyl]-3-methyl-6-[4-(trifluoromethyl)imidazol-1-yl]imidazo[4,5-c]pyridine are obtained.

(log P (neutral): 3.36; MH$^+$: 473; $^1$H NMR (600 MHz, CD$_3$CN) δ ppm: 8.905 (3.0); 8.903 (3.0); 8.852 (1.6); 8.850 (1.6); 8.500 (1.9); 8.313 (1.5); 8.311 (2.1); 8.309 (1.4); 8.183 (1.7); 8.181 (1.7); 7.962 (3.4); 7.961 (3.4); 4.001 (16.0); 3.940 (0.4); 3.124 (1.1); 3.111 (3.4); 3.099 (3.5); 3.087 (1.2); 2.639 (0.7); 2.184 (55.7); 2.109 (1.2); 2.005 (2.2); 1.998 (195.7); 1.989 (2.7); 1.985 (1.8); 1.981 (10.0); 1.977 (18.2); 1.973 (26.5); 1.969 (18.0); 1.965 (9.0); 1.882 (1.2); 1.419 (0.4); 1.404 (0.7); 1.373 (0.6); 1.330 (4.1); 1.318 (9.0); 1.309 (1.6); 1.305 (5.2); 1.301 (3.4); 0.914 (0.6).

In analogy to the examples and according to the above-described preparation processes, the following compounds of the formula (I) can be obtained:

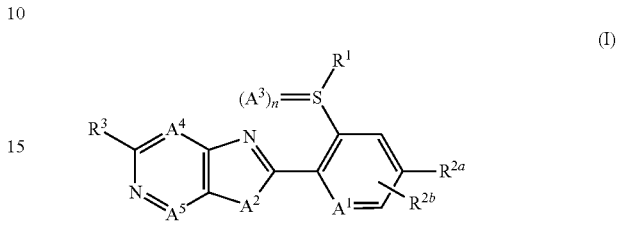

where A$^3$ is oxygen and the other substituents are each as defined in the following table:

| Ex. | R$^1$ | N | A$^4$ | A$^5$ | R$^3$ | A$^2$ | A$^1$ | R$^{2a}$ | R$^{2b}$ |
|---|---|---|---|---|---|---|---|---|---|
| I-1 | CH$_3$ | 0 | N | CH | CF$_3$ | O | CH | Cl | H |
| I-2 | C$_2$H$_5$ | 0 | CH | CH | CF$_3$ | N-methyl | N | CF$_3$ | H |
| I-3 | CH$_3$ | 0 | CH | CH | CF$_3$ | N-methyl | N | CF$_3$ | H |
| I-4 | CH$_3$ | 0 | CH | CH | CF$_3$ | N-methyl | CH | F | H |
| I-5 | CH$_3$ | 0 | CH | CH | CF$_3$ | N-methyl | CH | CF$_3$ | H |
| I-6 | CH$_3$ | 0 | N | CH | CF$_3$ | N-methyl | CH | Cl | H |
| I-7 | —(CH$_2$)$_2$—SO$_2$—C$_2$H$_5$ | 2 | CH | CH | CF$_3$ | N-methyl | N | CF$_3$ | H |
| I-8 | i-C$_3$H$_7$ | 1 | CH | CH | CF$_3$ | N-methyl | N | CF$_3$ | H |
| I-9 | C$_2$H$_5$ | 0 | N | CH | CF$_3$ | O | CH | H | H |
| I-10 | CH$_3$ | 1 | CH | CH | CF$_3$ | N-methyl | CH | Cl | H |
| I-11 | CH$_3$ | 2 | CH | CH | CF$_3$ | N-methyl | CH | Cl | H |
| I-12 | CH$_3$ | 1 | CH | CH | CF$_3$ | N-methyl | CH | F | H |
| I-13 | C$_2$H$_5$ | 1 | CH | CH | CF$_3$ | N-methyl | CH | H | 5-Cl* |
| I-14 | CH$_3$ | 2 | CH | CH | CF$_3$ | N-methyl | CH | 3 | H |
| I-15 | C$_2$H$_5$ | 2 | CH | CH | CF$_3$ | N-methyl | N | H | H |
| I-16 | i-C$_3$H$_7$ | 2 | CH | CH | CF$_3$ | N-methyl | N | CF$_3$ | H |
| I-17 | C$_2$H$_5$ | 0 | CH | CH | CF$_3$ | N-methyl | CH | H | H |
| I-18 | C$_2$H$_5$ | 2 | CH | CH | CF$_3$ | N-methyl | CH | H | H |
| I-19 | C$_2$H$_5$ | 0 | CH | CH | CF$_3$ | N-methyl | CH | H | 5-Cl* |
| I-20 | CH$_3$ | 2 | CH | CH | CF$_3$ | N-methyl | CH | F | H |
| I-21 | C$_2$H$_5$ | 2 | CH | CH | CF$_3$ | N-methyl | N | CF$_3$ | H |
| I-22 | C$_2$H$_5$ | 1 | CH | CH | CF$_3$ | N-methyl | CH | H | H |
| I-23 | —(CH$_2$)$_2$—S—C$_2$H$_5$ | 0 | CH | CH | CF$_3$ | N-methyl | N | CF$_3$ | H |
| I-24 | C$_2$H$_5$ | 0 | CH | CH | CF$_3$ | N-methyl | N | H | H |
| I-25 | CH$_3$ | 0 | CH | CH | CF$_3$ | N-methyl | CH | Cl | H |
| I-26 | CH$_3$ | 1 | CH | CH | CF$_3$ | N-methyl | N | CF$_3$ | H |
| I-27 | oxetan-3-yl | 2 | CH | CH | CF$_3$ | N-methyl | CH | H | H |

| Ex. | R¹ | N | A⁴ | A⁵ | R³ | A² | A¹ | R²ᵃ | R²ᵇ |
|---|---|---|---|---|---|---|---|---|---|
| I-28 | $C_2H_5$ | 0 | N | CH | $CF_3$ | N-methyl | N | $CF_3$ | H |
| I-29 | $CF_3$ | 0 | CH | CH | $CF_3$ | N-methyl | N | H | H |
| I-30 | $CH_3$ | 1 | CH | CH | $CF_3$ | N-methyl | CH | $CF_3$ | H |
| I-31 | $n-C_3H_7$ | 0 | CH | CH | $CF_3$ | N-methyl | N | $CF_3$ | H |
| I-32 | $n-C_3H_7$ | 2 | CH | CH | $CF_3$ | N-methyl | N | $CF_3$ | H |
| I-33 | $C_2H_5$ | 1 | CH | CH | $CF_3$ | N-methyl | N | H | H |
| I-34 | $CH_3$ | 0 | CH | CH | $CF_3$ | O | CH | Cl | H |
| I-35 | $C_2H_5$ | 0 | CH | CH | $CF_3$ | O | CH | H | H |
| I-36 | $CH_3$ | 2 | CH | CH | $CF_3$ | N-methyl | N | $CF_3$ | H |
| I-37 | $C_2H_5$ | 1 | CH | CH | $CF_3$ | N-methyl | N | $CF_3$ | H |
| I-38 | $C_2H_5$ | 2 | CH | CH | $CF_3$ | N-methyl | CH | H | 5-Cl* |
| I-39 | $n-C_3H_7$ | 1 | CH | CH | $CF_3$ | N-methyl | N | $CF_3$ | H |
| I-40 | oxetan-3-yl | 0 | CH | CH | $CF_3$ | O | CH | H | H |
| I-41 | $i-C_3H_7$ | 0 | CH | CH | $CF_3$ | N-methyl | N | $CF_3$ | H |
| I-42 | $C_2H_5$ | 0 | CH | CH | $CF_3$ | N-methyl | CH | Cl | H |
| I-43 | $C_2H_5$ | 2 | CH | CH | $CF_3$ | N-methyl | CH | Cl | H |
| I-44 | $C_2H_5$ | 1 | CH | CH | $CF_3$ | N-methyl | CH | Cl | H |
| I-45 | $C_2H_5$ | 2 | CH | CH | $CF_3$ | N-methyl | N | H | 5-OMe* |
| I-46 | $C_2H_5$ | 0 | CH | CH | $C_2F_5$ | N-methyl | N | H | H |
| I-47 | $C_2H_5$ | 0 | CH | CH | $C_2F_5$ | N-methyl | N | $CF_3$ | H |
| I-48 | $C_2H_5$ | 2 | CH | CH | $CF_3$ | N-methyl | N | H | 3-$CF_3$* |
| I-49 | $C_2H_5$ | 2 | CH | CH | $CF_3$ | N-methyl | N | H | 5-NHCOMe* |
| I-50 | $C_2H_5$ | 0 | CH | CH | $CF_3$ | N-methyl | N | H | 5-NHCOMe* |
| I-51 | $C_2H_5$ | 1 | CH | CH | $CF_3$ | N-methyl | N | H | 3-$CF_3$* |
| I-52 | $C_2H_5$ | 2 | CH | CH | Cl | N-methyl | N | $CF_3$ | H |
| I-53 | $C_2H_5$ | 0 | CH | CH | $CF_3$ | N-methyl | N | H | 5-OMe* |
| I-54 | $CH_2-CH_2F$ | 2 | CH | CH | $CF_3$ | N-methyl | N | $CF_3$ | H |
| I-55 | $C_2H_5$ | 0 | CH | CH | Cl | N-methyl | N | $CF_3$ | H |
| I-56 | $C_2H_5$ | 2 | CH | CH | $CF_3$ | N-methyl | N | $CONH_2$ | H |
| I-57 | $CH_2-CH_2F$ | 2 | CH | CH | $CF_3$ | N-methyl | N | $CF_3$ | H |
| I-58 | $CH_2-CH_2OH$ | 2 | CH | CH | $CF_3$ | N-methyl | N | $CF_3$ | H |
| I-59 | $CH_2-CH_2OH$ | 0 | CH | CH | $CF_3$ | N-methyl | N | $CF_3$ | H |
| I-60 | $C_2H_5$ | 0 | CH | CH | $CF_3$ | N-methyl | N | $CONH_2$ | H |
| I-61 | $C_2H_5$ | 1 | CH | CH | $C_2F_5$ | N-methyl | N | H | H |
| I-62 | $C_2H_5$ | 2 | CH | CH | $CF_3$ | N-methyl | CH | H | 3-Cl* |
| I-63 | $C_2H_5$ | 1 | CH | CH | $C_2F_5$ | N-methyl | N | $CF_3$ | H |
| I-64 | $C_2H_5$ | 0 | CH | CH | 4-$CF_3(C_6H_4)$ | N-methyl | N | $CF_3$ | H |
| I-65 | $C_2H_5$ | 0 | CH | CH | 4-$(CF_3)$pyrazol-1-yl | N-methyl | N | $CF_3$ | H |
| I-66 | $n-C_3H_7$ | 0 | CH | CH | $CF_3$ | N-methyl | N | H | 5-OMe* |

-continued

| Ex. | $R^1$ | N | $A^4$ | $A^5$ | $R^3$ | $A^2$ | $A^1$ | $R^{2a}$ | $R^{2b}$ |
|---|---|---|---|---|---|---|---|---|---|
| I-67 | $CH_3$ | 0 | CH | CH | $CF_3$ | N-methyl | N | H | 5-OMe* |
| I-68 | $C_2H_5$ | 2 | CH | CH | $C_2F_5$ | N-methyl | N | H | H |
| I-69 | $C_2H_5$ | 0 | CH | CH | 3-($CF_3$)pyrazol-1-yl | N-methyl | N | $CF_3$ | H |
| I-70 | $C_2H_5$ | 0 | CH | CH | $CF_3$ | N-methyl | N | H | 3-$CF_3$* |
| I-71 | n-$C_3H_7$ | 2 | CH | CH | $CF_3$ | N-methyl | N | H | 5-OMe* |
| I-72 | $C_2H_5$ | 2 | CH | CH | $CF_3$ | N-methyl | N | CN | H |
| I-73 | $CH_3$ | 2 | CH | CH | $CF_3$ | N-methyl | N | H | 5-OMe* |
| I-74 | $C_2H_5$ | 0 | CH | CH | 4-($CF_3$)imidazol-1-yl | N-methyl | N | $CF_3$ | H |
| I-75 | $C_2H_5$ | 2 | CH | CH | 4-($CF_3$)imidazol-1-yl | N-methyl | N | $CF_3$ | H |
| I-76 | $C_2H_5$ | 2 | CH | CH | 4-($CF_3$)pyrazol-1-yl | N-methyl | N | $CF_3$ | H |
| I-77 | $C_2H_5$ | 2 | CH | CH | 3-($CF_3$)pyrazol-1-yl | N-methyl | N | $CF_3$ | H |

*In these examples, $R^{2b}$ is joined in the 3 or 5 position:

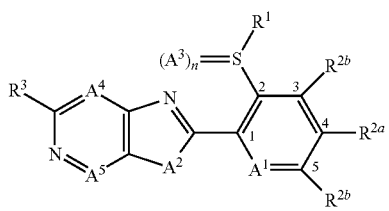

The log P values are measured according to EEC Directive 79/831 Annex V.A8 by HPLC (high-performance liquid chromatography) on a reversed-phase column (C 18). Temperature: 55° C.

The LC-MS determination in the acidic range is effected at pH 2.7 using 0.1% aqueous formic acid and acetonitrile (contains 0.1% formic acid) as eluents, linear gradient from 10% acetonitrile to 95% acetonitrile. Called log P (HCOOH) in the table.

LC-MS determination in the neutral range is effected at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is effected with unbranched alkan-2-ones (having 3 to 16 carbon atoms) with known log P values (log P values determined on the basis of the retention times by linear interpolation between two successive alkanone s).

The NMR data for selected examples are listed either in conventional form (δ values, multiplet splitting, number of hydrogen atoms) or as NMR peak lists.

The solvent in which the NMR spectrum was recorded is reported in each case.

NMR Peak List Method

The $^1$H NMR data of selected examples are reported in the form of $^1$H NMR peak lists. For each signal peak, first the δ value in ppm and then the signal intensity in round brackets are listed. The δ value signal intensity number pairs for different signal peaks are listed with separation from one another by semicolons.

The peak list for one example therefore takes the form of:

$\delta_1$(intensity$_1$);$\delta_2$(intensity$_2$); . . . ;
$\delta_i$(intensity$_i$); . . . ;$\delta_n$(intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of $^1$H NMR spectra we use tetramethylsilane and/or the chemical shift of the solvent, particularly in the case of spectra measured in DMSO. Therefore, the tetramethylsilane peak may, but need not, occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of $^1$H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Further details of $^1$H NMR peak lists can be found in Research Disclosure Database Number 564025.

| Ex. | LOGP_NEUTRAL | LOGP_HCOOH | |
|---|---|---|---|
| I-1 | 3.77 | 3.86 | Example 1: $^1$H-NMR (400.0 MHz, d$_6$-DMSO):<br>δ = 9.544 (6.4); 8.335 (3.9); 8.314 (4.1); 7.568 (2.9); 7.563 (3.5); 7.534 (2.5); 7.529 (1.9); 7.513 (2.3); 7.508 (1.9); 3.323 (17.6); 2.671 (0.3); 2.631 (16.0); 2.524 (1.1); 2.511 (19.3); 2.507 (38.0); 2.502 (49.6); 2.498 (35.5); 2.493 (16.9); 2.075 (0.5); 0.008 (0.9); 0.000 (21.7); −0.008 (0.7) |
| I-2 | 3.48 | 3.52 | Example 2: $^1$H-NMR (400.0 MHz, d$_6$-DMSO):<br>δ = 9.283 (3.7); 8.960 (2.3); 8.958 (2.3); 8.334 (2.7); 8.328 (4.1); 4.030 (16.0); 3.323 (69.7); 3.181 (1.1); 3.162 (3.6); 3.144 (3.6); 3.126 (1.1); 2.891 (1.2); 2.731 (1.0); 2.676 (0.4); 2.671 (0.6); 2.667 (0.4); 2.506 (64.4); 2.502 (83.6); 2.498 (61.3); 2.333 (0.4); 2.329 (0.5); 2.324 (0.4); 1.234 (4.1); 1.215 (8.1); 1.197 (3.8); 0.008 (0.6); 0.000 (17.0); −0.008 (0.7) |
| I-3 | 3.16 | 3.22 | Example 3: $^1$H-NMR (400.0 MHz, d$_6$-DMSO):<br>δ = 9.290 (4.0); 8.947 (2.7); 8.316 (4.5); 8.267 (2.9); 7.953 (0.4); 4.059 (16.0); 4.019 (0.7); 3.327 (63.2); 3.036 (0.3); 2.965 (0.4); 2.892 (2.5); 2.882 (0.5); 2.870 (0.5); 2.732 (2.2); 2.673 (0.5); 2.580 (15.1); 2.507 (59.9); 2.503 (71.6); 2.499 (52.5); 2.330 (0.5); 2.078 (0.4); 1.234 (0.4); 0.000 (0.4) |
| I-4 | 2.65 | 2.70 | Example 4: $^1$H-NMR (400.0 MHz, d$_6$-DMSO):<br>δ = 9.833 (0.3); 9.210 (3.9); 8.226 (4.1); 8.082 (0.6); 7.993 (0.5); 7.608 (1.3); 7.593 (1.5); 7.587 (1.6); 7.572 (1.4); 7.411 (1.3); 7.405 (1.4); 7.386 (1.4); 7.380 (1.4); 7.244 (1.0); 7.238 (0.9); 7.222 (1.6); 7.216 (1.5); 7.201 (0.8); 7.195 (0.7); 3.785 (16.0); 3.325 (80.3); 2.875 (1.0); 2.863 (1.0); 2.671 (0.7); 2.667 (0.6); 2.506 (76.1); 2.502 (99.5); 2.498 (78.2); 2.464 (2.7); 2.329 (0.6); 2.075 (0.3); 0.000 (2.6) |
| I-5 | 3.26 | 3.30 | Example 5: $^1$H-NMR (400.0 MHz, d$_6$-DMSO):<br>δ = 9.249 (3.5); 8.267 (3.7); 7.787 (1.2); 7.778 (2.7); 7.768 (2.9); 7.749 (2.1); 7.729 (0.7); 3.807 (16.0); 3.324 (21.7); 2.671 (0.4); 2.557 (15.5); 2.524 (1.1); 2.511(22.7); 2.507 (44.4); 2.502 (57.4); 2.498 (41.7); 2.493 (20.4); 2.329 (0.4); 0.008 (2.1); 0.000 (52.3); −0.009 (2.1) |
| I-6 | 2.74 | 2.75 | Example 6: $^1$H-NMR (601.6 MHz, CD3CN):<br>δ = 9.182 (3.5); 7.526 (1.9); 7.523 (2.0); 7.459 (1.7); 7.445 (2.7); 7.403 (1.7); 7.400 (1.6); 7.390 (1.1); 7.386 (1.0); 3.927 (0.3); 3.770 (16.0); 2.978 (0.3); 2.494 (14.5); 2.222 (0.5); 2.152 (1.6); 1.966 (0.6); 1.958 (1.5); 1.954 (1.8); 1.950 (9.9); 1.946 (17.5); 1.942 (25.9); 1.938 (17.6); 1.934 (8.7); 1.387 (5.1); 1.269 (0.3); 1.212 (0.4); 0.005 (0.3); 0.000 (11.9); −0.006 (0.4) |
| I-7 | 2.67 | 2.72 | Example 7: $^1$H-NMR (400.0 MHz, d$_6$-DMSO):<br>δ = 9.411 (2.3); 9.408 (2.3); 9.379 (3.9); 9.333 (0.4); 8.751 (2.4); 8.746 (2.5); 8.460 (4.1); 8.316 (0.5); 7.903 (0.3); 4.391 (16.0); 4.199 (1.2); 4.147 (0.5); 4.138 (0.4); 4.121 (0.8); 4.114 (0.6); 4.107 (0.7); 4.100 (0.7); 4.088 (0.7); 4.068 (0.4); 3.976 (0.7); 3.854 (0.6); 3.843 (0.6); 3.833 (0.7); 3.829 (0.7); 3.819 (0.8); 3.803 (0.5); 3.795 (0.6); 3.556 (0.6); 3.543 (0.8); 3.531 (0.5); 3.523 (0.6); 3.518 (0.8); 3.510 (0.9); 3.494 (1.8); 3.477 (0.8); 3.468 (0.8); 3.464 (0.6); 3.455 (0.5); 3.443 (0.6); 3.429 (0.4); 3.325 (63.6); 3.260 (0.8); 3.257 (0.8); 3.241 (2.2); 3.238 (2.3); 3.223 (2.3); 3.219 (2.3); 3.201 (0.9); 2.676 (0.5); 2.671 (0.7); 2.667 (0.6); 2.524 (1.8); 2.511(41.0); 2.506 (84.3); 2.502 (113.7); 2.498 (86.8); 2.493 (45.8); 2.333 (0.5); 2.329 (0.7); 2.324 (0.6); 1.252 (4.4); 1.233 (9.5); 1.214 (4.3); 0.146 (0.4); 0.008 (2.7); 0.000 (79.8); −0.008 (4.6); −0.150 (0.4) |
| I-8 | 3.46 | 3.54 | Example 8: $^1$H-NMR (400.0 MHz, d$_6$-DMSO):<br>δ = 9.390 (2.1); 9.387 (2.1); 9.377 (3.6); 8.577 (2.1); 8.572 (2.2); 8.379 (3.7); 8.316 (0.6); 4.384 (16.0); 4.362 (0.4); 3.802 (0.3); 3.785 (0.9); 3.767 (1.3); 3.750 (0.9); 3.733 (0.4); 3.322 (86.4); 2.675 (1.0); 2.671 (1.4); 2.666 (1.0); 2.524 (3.7); 2.511(79.1); 2.506 (160.9); 2.502 (213.1); 2.497 (155.9); 2.493 (76.9); 2.333 (1.0); 2.329 (1.4); 2.324 (1.0); 1.569 (6.3); 1.551 (6.2); 0.906 (6.4); 0.889 (6.3); 0.146 (1.3); 0.008 (10.0); 0.000 (280.2); −0.008 (11.2); −0.150 (1.3) |
| I-9 | 3.64 | 3.66 | Example 9: $^1$H-NMR (400.0 MHz, d$_6$-DMSO):<br>δ = 9.544 (9.2); 8.314 (2.7); 8.311 (2.8); 8.294 (2.9); 8.291 (2.8); 7.739 (1.1); 7.735 (1.2); 7.719 (2.5); 7.715 (2.1); 7.701 (2.2); 7.697 (2.1); 7.646 (3.6); 7.627 (2.2); 7.464 (1.9); 7.462 (1.8); 7.444 (3.0); 7.426 (1.6); 7.424 (1.5); 3.322 (31.6); 3.155 (1.9); 3.136 (6.3); 3.118 (6.4); 3.100 (2.0); 2.676 (0.6); 2.671 (0.8); 2.666 (0.6); 2.541 (0.6); 2.524 (2.7); 2.511 (49.3); 2.507 (97.6); 2.502 (126.8); 2.497 (89.7); 2.493 (42.1); 2.333 (0.6); 2.329 (0.8); 2.324 (0.6); 2.075 (0.3); 1.360 (7.3); 1.341 (16.0); 1.323 (7.0); 0.146 (0.3); 0.008 (3.4); 0.000 (84.9); −0.009 (2.9); −0.150 (0.3) |
| I-10 | 2.08 | 2.15 | Example 10: $^1$H-NMR (400.0 MHz, d$_6$-DMSO):<br>δ = 9.271 (3.7); 8.267 (3.9); 8.137 (2.9); 8.132 (3.0); 7.975 (2.1); 7.954 (3.6); 7.900 (2.2); 7.895 (2.1); 7.880 (1.3); 7.874 (1.3); 6.870 (0.3); 3.977 (15.9); 3.748 (0.9); 3.444 (0.8); 3.327 (95.2); 2.967 (16.0); 2.676 (0.3); 2.671 (0.5); 2.667 (0.3); 2.525 (1.4); 2.507 (54.5); 2.502 (70.2); 2.498 (50.6); 2.494 (24.6); 2.333 (0.3); 2.329 (0.4); 2.184 (0.5); 1.355 (3.8); 1.298 (0.9); 1.259 (1.2); 1.234 (0.6); 0.008 (2.1); 0.000 (54.1); −0.009 (2.3) |
| I-11 | 2.34 | 2.39 | Example 11: $^1$H-NMR (400.0 MHz, d$_6$-DMSO):<br>δ = 9.279 (0.6); 9.262 (3.9); 8.380 (0.5); 8.317 (0.5); 8.260 (4.2); 8.164 (2.8); 8.159 (3.4); 8.152 (0.5); 8.115 (1.7); 8.110 (1.5); 8.095 (2.1); 8.089 (1.9); 7.937 (3.4); 7.917 (3.0); 7.902 (0.8); 7.897 (0.9); 7.885 (0.5); 7.565 (0.4); 7.545 (0.6); 5.757 (1.6); 3.770 (0.5); 3.747 (16.0); 3.621 (0.4); 3.592 (1.6); 3.445 (15.1); 3.436 (2.1); 3.327 (141.8); 2.675 (0.9); 2.671 (1.2); 2.667 (0.9); 2.524 (4.2); 2.506 |

-continued

| Ex. | LOGP_NEUTRAL | LOGP_HCOOH | |
|---|---|---|---|
| I-12 | 1.83 | 1.88 | (141.2); 2.502 (182.5); 2.498 (131.5); 2.333 (0.8); 2.329 (1.1); 2.324 (0.8); 1.298 (0.8); 1.259 (1.1); 1.235 (0.5); 1.166 (0.3); 0.008 (2.3); 0.000 (56.4); −0.008 (2.3) Example 12: $^1$H-NMR (400.0 MHz, d$_6$-DMSO): δ = 9.272 (4.2); 8.266 (4.5); 8.036 (1.3); 8.023 (1.4); 8.015 (1.6); 8.002 (1.5); 7.966 (1.4); 7.959 (1.6); 7.944 (1.5); 7.937 (1.5); 7.706 (0.8); 7.699 (0.8); 7.685 (1.5); 7.678 (1.5); 7.664 (0.8); 7.657 (0.7); 3.973 (16.0); 3.336 (80.5); 2.958 (16.0); 2.678 (0.4); 2.549 (0.3); 2.509 (67.3); 2.337 (0.4) |
| I-13 | 2.34 | 2.44 | Example 13: $^1$H-NMR (400.0 MHz, d$_6$-DMSO): δ = 9.285 (3.9); 8.280 (4.2); 8.088 (2.3); 8.066 (4.9); 8.060 (3.8); 8.009 (2.3); 8.004 (2.0); 7.988 (1.4); 7.983 (1.3); 3.973 (16.0); 3.327 (56.5); 3.313 (1.6); 3.294 (1.2); 3.279 (1.2); 3.261 (1.1); 3.242 (0.3); 2.905 (1.1); 2.886 (1.2); 2.871 (1.0); 2.853 (1.0); 2.671 (0.4); 2.507 (41.3); 2.502 (56.0); 2.498 (43.9); 2.329 (0.4); 1.150 (3.8); 1.132 (8.2); 1.113 (3.7); 0.000 (2.5) |
| I-14 | 2.63 | 2.67 | Example 14: $^1$H-NMR (400.0 MHz, d$_6$-DMSO): δ = 9.289 (3.7); 8.430 (1.3); 8.412 (5.2); 8.288 (3.9); 8.287 (3.9); 8.180 (1.6); 8.159 (1.4); 3.772 (16.0); 3.493 (14.4); 3.324 (34.4); 2.524 (0.9); 2.511 (17.9); 2.506 (36.4); 2.502 (48.8); 2.497 (36.6); 2.493 (18.8); 0.008 (1.9); 0.000 (52.6); −0.008 (2.6) |
| I-15 | 1.92 | 1.95 | Example 15: $^1$H-NMR (400.0 MHz, d$_6$-DMSO): δ = 9.295 (3.5); 9.139 (1.7); 9.135 (1.9); 9.127 (1.9); 9.123 (1.8); 8.579 (1.7); 8.575 (1.8); 8.559 (1.9); 8.555 (1.8); 8.300 (3.6); 8.298 (3.7); 8.021 (1.9); 8.009 (1.8); 8.001 (1.7); 7.989 (1.7); 3.867 (16.0); 3.794 (1.0); 3.775 (3.5); 3.757 (3.5); 3.738 (1.0); 3.327 (10.2); 2.526 (0.5); 2.521 (0.7); 2.512 (10.8); 2.508 (22.2); 2.503 (29.5); 2.499 (21.4); 2.494 (10.4); 1.209 (3.6); 1.191 (7.9); 1.172 (3.5); 0.008 (1.8); 0.000 (50.2); −0.009 (1.9) |
| I-16 | 3.21 | 3.26 | Example 16: $^1$H-NMR (400.0 MHz, d$_6$-DMSO): δ = 9.588 (2.0); 9.585 (2.1); 9.314 (3.5); 8.780 (2.2); 8.776 (2.2); 8.331 (3.7); 8.316 (0.4); 4.409 (0.3); 4.392 (1.0); 4.375 (1.4); 4.357 (1.0); 4.340 (0.3); 3.914 (16.0); 3.322 (36.9); 2.676 (0.6); 2.671 (0.8); 2.667 (0.6); 2.524 (2.0); 2.520 (3.2); 2.511(42.6); 2.507 (88.2); 2.502 (118.2); 2.497 (86.9); 2.493 (42.9); 2.333 (0.5); 2.329 (0.7); 2.324 (0.6); 1.260 (13.3); 1.243 (13.2); 0.146 (0.8); 0.008 (6.7); 0.000 (191.2); −0.009 (7.6); −0.150 (0.8) |
| I-17 | 2.87 | 2.94 | Example 17: $^1$H-NMR (400.0 MHz, d$_6$-DMSO): δ = 9.204 (3.8); 8.228 (4.1); 7.627 (3.7); 7.618 (4.2); 7.536 (1.5); 7.517 (2.1); 7.433 (0.9); 7.422 (1.2); 7.413 (1.2); 7.403 (1.1); 7.392 (0.6); 3.768 (16.0); 3.327 (67.1); 2.986 (1.3); 2.968 (4.1); 2.950 (4.1); 2.931 (1.4); 2.671 (0.5); 2.667 (0.3); 2.507 (57.2); 2.503 (74.4); 2.498 (54.2); 2.334 (0.3); 2.329 (0.5); 2.325 (0.4); 1.180 (4.3); 1.161 (8.7); 1.143 (4.1); 0.146 (0.5); 0.008 (3.9); 0.000 (88.8); −0.007 (3.9); −0.150 (0.5) |
| I-18 | 2.11 | 2.13 | Example 18: $^1$H-NMR (400.0 MHz, d$_6$-DMSO): δ = 9.255 (3.5); 8.253 (3.7); 8.251 (3.6); 8.156 (1.3); 8.153 (1.3); 8.138 (1.8); 8.134 (1.6); 8.020 (0.4); 8.017 (0.5); 8.002 (1.4); 7.998 (1.4); 7.984 (1.6); 7.979 (1.5); 7.976 (1.4); 7.971 (1.6); 7.957 (1.5); 7.953 (1.5); 7.938 (0.6); 7.934 (0.5); 7.878 (1.7); 7.875 (1.8); 7.860 (1.2); 7.857 (1.2); 3.728 (16.0); 3.526 (0.5); 3.509 (1.3); 3.490 (1.3); 3.473 (0.5); 3.330 (61.8); 2.671 (0.4); 2.525 (1.2); 2.511(25.5); 2.507 (50.6); 2.502 (65.3); 2.498 (46.3); 2.493 (21.9); 2.329 (0.4); 1.119 (3.5); 1.101 (7.8); 1.082 (3.4); 0.008 (0.6); 0.000 (15.4); −0.009 (0.6) |
| I-19 | 3.38 | 3.43 | Example 19: $^1$H-NMR (400.0 MHz, d$_6$-DMSO): δ = 9.226 (3.9); 8.243 (4.1); 7.705 (0.9); 7.699 (1.3); 7.684 (1.6); 7.678 (2.9); 7.667 (3.6); 7.662 (2.3); 7.640 (3.4); 7.619 (1.8); 3.788 (16.0); 3.323 (25.4); 2.999 (1.2); 2.981 (4.0); 2.963 (4.1); 2.944 (1.3); 2.671 (0.4); 2.626 (0.3); 2.507 (47.1); 2.502 (61.4); 2.498 (45.8); 2.329 (0.4); 2.300 (0.5); 1.177 (4.3); 1.159 (8.9); 1.140 (4.1); 0.008 (1.9); 0.000 (45.5) |
| I-20 | 2.05 | 2.08 | Example 20: $^1$H-NMR (400.0 MHz, d$_6$-DMSO): δ = 9.258 (4.1); 8.253 (4.3); 7.997 (1.5); 7.990 (2.5); 7.976 (2.4); 7.969 (3.3); 7.956 (1.7); 7.918 (1.1); 7.911 (0.9); 7.897 (1.6); 7.890 (1.4); 7.876 (0.7); 7.869 (0.6); 3.739 (16.0); 3.430 (15.0); 3.326 (81.6); 2.671 (0.7); 2.666 (0.6); 2.506 (84.7); 2.502 (108.3); 2.498 (84.4); 2.328 (0.7); 2.325 (0.5); 0.146 (0.6); 0.000 (128.1); −0.150 (0.6) |
| I-21 | 2.93 | 2.98 | Example 21: $^1$H-NMR (400.0 MHz, d$_6$-DMSO): δ = 9.586 (2.4); 9.583 (2.5); 9.317 (4.1); 8.798 (2.5); 8.794 (2.6); 8.341 (4.3); 3.925 (16.0); 3.912 (1.3); 3.893 (3.6); 3.874 (3.7); 3.856 (1.1); 3.324 (30.3); 2.671 (0.5); 2.506 (56.1); 2.502 (72.8); 2.498 (55.3); 2.329 (0.5); 1.258 (3.8); 1.239 (8.2); 1.221 (3.7); 0.146 (0.4); 0.007 (3.2); 0.000 (79.6); −0.150 (0.4) |
| I-22 | 1.87 | 1.90 | Example 22: $^1$H-NMR (400.0 MHz, d$_6$-DMSO): δ = 9.261 (3.9); 8.261 (4.1); 8.107 (1.6); 8.087 (2.0); 7.942 (0.8); 7.940 (1.0); 7.921 (1.7); 7.904 (2.1); 7.901 (2.4); 7.885 (2.2); 7.820 (1.2); 7.818 (1.3); 7.801 (1.6); 7.799 (1.6); 7.783 (0.6); 7.780 (0.7); 5.757 (1.1); 3.946 (16.0); 3.728 (0.5); 3.328 (59.2); 3.305 (1.0); 3.286 (1.1); 3.272 (1.1); 3.253 (1.1); 2.885 (1.1); 2.867 (1.2); 2.852 (1.0); 2.833 (1.0); 2.672 (0.3); 2.507 (37.2); 2.502 (48.9); 2.498 (35.7); 1.149 (3.9); 1.130 (8.2); 1.112 (3.7); 1.102 (0.4); 0.007 (1.5); 0.000 (35.2); −0.008 (1.5) |
| I-23 | 3.96 | 4.02 | Example 23: $^1$H-NMR (400.0 MHz, d$_6$-DMSO): δ = 9.288 (4.1); 8.977 (2.7); 8.456 (2.7); 8.327 (4.3); 8.317 (0.4); 4.033 (16.0); 3.395 (2.0); 3.377 (2.7); 3.357 (2.4); 3.327 (77.5); 2.720 (2.3); 2.701 (2.8); 2.682 (2.2); 2.672 (0.7); 2.579 (1.5); 2.560 (4.6); 2.542 (4.9); 2.523 (3.2); 2.507 (65.1); |

-continued

| Ex. | LOGP_ NEUTRAL | LOGP_ HCOOH | |
|---|---|---|---|
| I-24 | 2.32 | 2.39 | 2.502 (87.7); 2.498 (70.2); 2.329 (0.6); 2.075 (0.9); 1.233 (0.6); 1.152 (4.7); 1.133 (9.3); 1.115 (4.4); 0.000 (3.7)<br>Example 24: $^1$H-NMR (400.0 MHz, $d_6$-DMSO):<br>δ = 9.241 (3.7); 8.588 (1.6); 8.585 (1.8); 8.577 (1.7); 8.574 (1.8); 8.279 (3.8); 8.090 (1.5); 8.087 (1.6); 8.069 (1.7); 8.066 (1.8); 7.638 (1.6); 7.627 (1.6); 7.618 (1.5); 7.606 (1.5); 3.975 (16.0); 3.324 (34.0); 3.041 (1.1); 3.022 (3.7); 3.004 (3.8); 2.986 (1.2); 2.672 (0.3); 2.525 (0.8); 2.507 (40.5); 2.503 (55.3); 2.498 (43.4); 2.329 (0.4); 1.218 (4.0); 1.199 (8.3); 1.181 (3.9); 0.008 (1.5); 0.000 (45.1) |
| I-25 | 2.97 | 3.08 | Example 25: $^1$H-NMR (400.0 MHz, $d_6$-DMSO):<br>δ = 9.217 (3.6); 8.235 (3.9); 7.564 (2.9); 7.560 (3.0); 7.555 (3.0); 7.544 (3.5); 7.460 (2.0); 7.455 (1.8); 7.440 (1.4); 7.435 (1.3); 3.791 (16.0); 3.323 (28.6); 2.671 (0.3); 2.506 (48.4); 2.502 (56.6); 2.498 (37.8); 2.329 (0.4); 1.398 (0.8); 0.008 (2.5); 0.000 (64.5); −0.008 (2.5) |
| I-26 | 2.76 | 2.81 | Example 26: $^1$H-NMR (400.0 MHz, $d_6$-DMSO):<br>δ = 9.389 (2.0); 9.386 (2.0); 9.366 (3.5); 8.849 (2.2); 8.845 (2.1); 8.370 (3.7); 6.870 (0.5); 5.756 (0.4); 4.452 (0.5); 4.347 (15.7); 4.018 (0.6); 3.995 (0.4); 3.326 (80.4); 3.151 (16.0); 2.676 (0.4); 2.671 (0.5); 2.667 (0.3); 2.524 (1.2); 2.511 (28.7); 2.507 (56.3); 2.502 (72.6); 2.498 (52.3); 2.494 (25.3); 2.334 (0.4); 2.329 (0.5); 2.325 (0.3); 2.183 (0.8); 1.355 (5.8); 1.233 (0.6); 0.008 (1.2); 0.000 (33.6); −0.009 (1.3) |
| I-27 | 1.84 | 1.87 | Example 27: $^1$H-NMR (400.0 MHz, $d_6$-DMSO):<br>δ = 9.253 (3.5); 8.275 (3.8); 8.273 (3.7); 8.257 (1.5); 8.254 (1.4); 8.237 (1.8); 8.234 (1.7); 8.038 (0.5); 8.035 (0.6); 8.020 (1.5); 8.016 (1.7); 7.998 (1.3); 7.984 (1.2); 7.980 (1.4); 7.965 (1.6); 7.961 (1.7); 7.946 (0.7); 7.942 (0.6); 7.903 (0.9); 7.895 (2.1); 7.892 (2.0); 7.877 (1.4); 7.873 (1.3); 7.567 (0.4); 7.547 (0.6); 5.756 (8.2); 5.231 (0.7); 5.226 (0.6); 5.216 (0.5); 5.211 (1.3); 5.205 (0.5); 5.196 (0.7); 5.190 (0.8); 5.175 (0.4); 4.802 (2.1); 4.783 (4.1); 4.763 (2.6); 4.673 (2.9); 4.657 (3.1); 4.639 (2.0); 3.746 (16.0); 3.732 (0.5); 3.602 (0.5); 3.594 (0.5); 3.325 (51.0); 2.676 (0.3); 2.671 (0.4); 2.524 (1.2); 2.511 (26.7); 2.507 (53.3); 2.502 (69.4); 2.498 (49.5); 2.493 (23.4); 2.333 (0.3); 2.329 (0.5); 1.760 (0.5); 1.236 (0.7); 1.190 (0.3); 0.000 (2.3) |
| I-28 | 3.22 | 3.29 | Example 28: $^1$H-NMR (400.0 MHz, $d_6$-DMSO):<br>δ = 9.561 (4.9); 8.983 (2.2); 8.362 (2.2); 8.359 (2.2); 4.075 (16.0); 4.032 (0.3); 4.022 (0.4); 3.323 (56.4); 3.202 (1.1); 3.184 (3.5); 3.165 (3.5); 3.147 (1.1); 2.676 (0.4); 2.671 (0.6); 2.667 (0.4); 2.511 (33.1); 2.507 (65.1); 2.502 (84.7); 2.498 (61.6); 2.494 (30.1); 2.333 (0.4); 2.329 (0.5); 2.324 (0.4); 1.355 (0.7); 1.252 (4.0); 1.233 (8.3); 1.215 (3.7); 0.008 (2.6); 0.000 (63.4); −0.008 (2.5) |
| I-29 | 2.93 | 3.04 | Example 29: $^1$H-NMR (400.0 MHz, $d_6$-DMSO):<br>δ = 9.302 (3.5); 8.962 (1.6); 8.959 (1.8); 8.951 (1.8); 8.947 (1.8); 8.457 (1.3); 8.437 (1.4); 8.334 (3.7); 7.856 (1.7); 7.845 (1.7); 7.836 (1.6); 7.824 (1.6); 4.092 (16.0); 3.329 (37.5); 2.526 (0.6); 2.512 (14.7); 2.508 (30.1); 2.504 (40.6); 2.499 (31.1); 2.495 (16.5); 0.000 (1.9) |
| I-30 | 2.36 | 2.41 | Example 30: $^1$H-NMR (400.0 MHz, $d_6$-DMSO):<br>δ = 9.307 (3.8); 8.443 (2.9); 8.305 (4.0); 8.190 (6.5); 4.008 (15.9); 3.327 (62.6); 2.995 (16.0); 2.676 (0.4); 2.671 (0.5); 2.667 (0.4); 2.511 (28.7); 2.507 (57.0); 2.502 (75.3); 2.498 (56.9); 2.334 (0.4); 2.329 (0.5); 2.325 (0.4); 0.000 (3.6) |
| I-31 | 3.86 | 3.94 | Example 31: $^1$H-NMR (400.0 MHz, $d_6$-DMSO):<br>δ = 9.283 (3.4); 8.955 (2.1); 8.952 (2.1); 8.347 (2.1); 8.343 (2.2); 8.334 (3.8); 4.021 (16.0); 3.324 (17.5); 3.137 (2.1); 3.119 (3.6); 3.101 (2.2); 2.892 (1.6); 2.732 (1.3); 2.672 (0.4); 2.525 (0.7); 2.512 (20.3); 2.507 (42.4); 2.503 (57.6); 2.498 (43.7); 2.494 (22.9); 2.329 (0.4); 1.607 (1.2); 1.588 (2.4); 1.570 (2.5); 1.552 (1.4); 0.961 (4.2); 0.943 (8.6); 0.924 (3.8); 0.008 (1.3); 0.000 (42.0); −0.009 (2.2) |
| I-32 | 3.32 | 3.37 | Example 32: $^1$H-NMR (400.0 MHz, $d_6$-DMSO):<br>δ = 9.580 (2.3); 9.577 (2.3); 9.316 (3.9); 8.796 (2.4); 8.792 (2.4); 8.350 (4.1); 7.903 (0.5); 7.898 (0.5); 7.547 (0.5); 5.756 (2.2); 3.923 (16.0); 3.898 (2.3); 3.883 (1.8); 3.878 (2.4); 3.873 (1.8); 3.859 (2.3); 3.775 (0.8); 3.323 (27.3); 2.676 (0.3); 2.671 (0.5); 2.667 (0.3); 2.524 (1.0); 2.511(25.7); 2.507 (52.2); 2.502 (69.6); 2.498 (51.6); 2.493 (26.0); 2.329 (0.4); 2.324 (0.3); 1.737 (1.1); 1.718 (1.9); 1.699 (2.0); 1.680 (1.2); 1.013 (4.1); 1.002 (0.9); 0.995 (8.4); 0.976 (3.8); 0.000 (9.4); −0.008 (0.4) |
| I-33 | 2.11 | 2.12 | Example 33: $^1$H-NMR (400.0 MHz, $d_6$-DMSO):<br>δ = 9.315 (3.7); 8.969 (1.6); 8.966 (1.8); 8.958 (1.8); 8.954 (1.7); 8.556 (1.6); 8.552 (1.7); 8.536 (1.8); 8.532 (1.7); 8.319 (4.0); 7.938 (1.7); 7.926 (1.6); 7.918 (1.6); 7.906 (1.5); 4.318 (16.0); 3.552 (0.9); 3.533 (1.0); 3.519 (1.1); 3.500 (1.1); 3.481 (0.3); 3.324 (25.2); 3.031 (1.1); 3.012 (1.2); 2.998 (1.0); 2.979 (1.0); 2.507 (37.9); 2.503 (49.7); 2.499 (37.5); 1.303 (3.8); 1.285 (8.0); 1.266 (3.7); 0.000 (5.3) |
| I-34 | 4.41 | 4.38 | Example 34: $^1$H-NMR (400.0 MHz, $d_6$-DMSO):<br>δ = 9.332 (3.7); 8.517 (4.3); 8.515 (4.4); 8.272 (3.7); 8.251 (3.9); 7.627 (0.5); 7.623 (0.6); 7.614 (0.4); 7.597 (0.5); 7.575 (0.4); 7.566 (0.4); 7.556 (0.4); 7.542 (2.9); 7.538 (3.4); 7.509 (2.4); 7.504 (1.7); 7.488 (2.1); 7.483 (1.8); 3.321 (35.3); 2.680 (0.4); 2.675 (0.9); 2.671 (1.2); 2.666 (0.8); 2.662 (0.4); 2.610 (16.0); 2.524 (3.5); 2.511 (65.6); 2.506 (129.9); 2.502 (168.9); 2.497 (120.0); 2.493 (56.5); 2.337 (0.4); 2.333 (0.8); 2.329 (1.1); 2.324 (0.8); 2.320 (0.4); 1.355 (1.2); 1.328 (0.4); 1.207 (0.3); 1.189 (0.7); 1.168 (2.5); 1.160 (2.3); 1.145 (0.4); 1.058 (0.5); 0.146 (0.4); 0.008 (3.6); 0.000 (97.2); −0.009 (3.2); −0.150 (0.4) |

-continued

| Ex. | LOGP_NEUTRAL | LOGP_HCOOH | |
|---|---|---|---|
| I-35 | 4.07 | 4.03 | Example 35: ¹H-NMR (400.0 MHz, d₆-DMSO):<br>δ = 9.334 (5.6); 8.540 (6.8); 8.538 (6.7); 8.234 (2.7); 8.231 (2.8); 8.214 (3.0); 8.211 (2.8); 7.693 (1.0); 7.690 (1.0); 7.673 (2.6); 7.669 (2.1); 7.655 (2.3); 7.651 (2.2); 7.621 (3.9); 7.602 (2.0); 7.440 (1.8); 7.437 (1.8); 7.420 (3.0); 7.402 (1.5); 7.399 (1.4); 3.323 (126.5); 3.130 (2.0); 3.112 (6.6); 3.093 (6.7); 3.075 (2.1); 2.680 (0.5); 2.675 (1.1); 2.671 (1.5); 2.666 (1.1); 2.662 (0.5); 2.524 (4.8); 2.511 (84.8); 2.506 (166.1); 2.502 (215.2); 2.497 (153.7); 2.493 (72.9); 2.333 (1.0); 2.329 (1.4); 2.324 (1.0); 1.333 (7.5); 1.315 (16.0); 1.297 (7.2); 0.008 (1.0); 0.000 (28.0); −0.009 (0.9) |
| I-36 | 2.64 | 2.67 | Example 36: ¹H-NMR (400.0 MHz, d₆-DMSO):<br>δ = 9.577 (2.7); 9.575 (2.7); 9.320 (4.2); 8.825 (2.8); 8.822 (2.8); 8.347 (4.5); 7.902 (0.7); 7.897 (0.7); 7.886 (0.4); 7.566 (0.3); 7.546 (0.5); 5.757 (1.3); 4.018 (1.1); 3.934 (16.0); 3.700 (15.4); 3.325 (73.6); 2.671 (0.7); 2.506 (74.4); 2.502 (95.9); 2.498 (76.5); 2.328 (0.6); 1.258 (0.3); 1.236 (1.0); 1.169 (0.8); 0.000 (2.4) |
| I-37 | 3.10 | 3.17 | Example 37: ¹H-NMR (400.0 MHz, d₆-DMSO):<br>δ = 9.392 (2.2); 9.388 (2.3); 9.369 (3.8); 8.726 (2.3); 8.721 (2.4); 8.385 (3.9); 8.316 (0.5); 4.362 (16.0); 3.627 (0.9); 3.608 (1.1); 3.594 (1.1); 3.575 (1.0); 3.324 (136.2); 3.117 (1.0); 3.098 (1.2); 3.084 (1.0); 3.065 (0.9); 2.676 (0.8); 2.671 (1.1); 2.667 (0.9); 2.507 (127.4); 2.502 (169.6); 2.498 (129.7); 2.333 (0.8); 2.329 (1.1); 2.325 (0.9); 1.330 (3.8); 1.312 (8.1); 1.293 (3.6); 0.146 (0.9); 0.008 (7.7); 0.000 (196.4); −0.150 (0.9) |
| I-38 | 2.63 | 2.68 | Example 38: ¹H-NMR (400.0 MHz, d₆-DMSO):<br>δ = 9.273 (3.9); 8.266 (4.2); 8.141 (2.4); 8.120 (3.8); 8.105 (2.9); 8.100 (3.4); 8.055 (2.4); 8.049 (2.0); 8.033 (1.5); 8.028 (1.3); 7.904 (0.8); 7.899 (0.7); 7.894 (0.5); 7.887 (0.5); 7.697 (0.3); 7.568 (0.5); 7.548 (0.8); 7.528 (0.3); 3.763 (16.0); 3.530 (0.6); 3.513 (1.3); 3.495 (1.4); 3.476 (0.6); 3.357 (0.5); 3.328 (61.7); 2.676 (0.4); 2.671 (0.5); 2.667 (0.4); 2.525 (1.3); 2.507 (57.0); 2.502 (75.7); 2.498 (56.3); 2.333 (0.3); 2.329 (0.5); 2.325 (0.3); 1.125 (3.8); 1.107 (8.1); 1.088 (3.6); 0.000 (0.6) |
| I-39 | 3.45 | 3.52 | Example 39: ¹H-NMR (400.0 MHz, d₆-DMSO):<br>δ = 9.386 (2.2); 9.383 (2.3); 9.374 (3.8); 8.774 (2.3); 8.769 (2.3); 8.316 (0.4); 8.302 (3.8); 5.756 (0.4); 4.362 (16.0); 3.637 (0.5); 3.616 (0.9); 3.605 (0.6); 3.596 (0.6); 3.585 (1.0); 3.564 (0.6); 3.322 (68.3); 2.993 (0.6); 2.981 (0.7); 2.973 (0.7); 2.961 (1.1); 2.949 (0.7); 2.941 (0.7); 2.928 (0.6); 2.676 (0.6); 2.671 (0.8); 2.666 (0.6); 2.511 (49.6); 2.506 (97.4); 2.502 (127.7); 2.497 (95.5); 2.493 (49.9); 2.333 (0.6); 2.329 (0.8); 2.324 (0.6); 2.029 (0.5); 2.010 (0.7); 1.994 (0.8); 1.975 (0.7); 1.956 (0.4); 1.804 (0.4); 1.789 (0.6); 1.783 (0.5); 1.770 (0.6); 1.757 (0.4); 1.754 (0.4); 1.146 (3.8); 1.128 (8.0); 1.109 (3.6); 0.146 (0.8); 0.008 (8.1); 0.000 (174.8); −0.008 (10.0); −0.150 (0.8) |
| I-40 | 3.10 | 3.15 | Example 40: ¹H-NMR (400.0 MHz, d₆-DMSO):<br>δ = 9.347 (4.8); 8.561 (5.7); 8.293 (2.2); 8.291 (2.3); 8.274 (2.4); 8.271 (2.3); 7.668 (1.0); 7.665 (1.1); 7.647 (2.2); 7.630 (1.4); 7.627 (1.3); 7.480 (1.7); 7.460 (2.8); 7.442 (1.3); 7.179 (2.9); 7.159 (2.6); 6.870 (1.5); 6.647 (0.8); 5.165 (3.3); 5.147 (6.3); 5.130 (3.6); 4.804 (0.5); 4.788 (1.2); 4.771 (1.9); 4.755 (1.2); 4.738 (0.4); 4.512 (3.8); 4.496 (6.3); 4.480 (3.3); 3.328 (53.8); 2.672 (0.6); 2.507 (73.4); 2.503 (93.5); 2.499 (70.8); 2.330 (0.6); 2.183 (2.4); 1.355 (16.0); 1.233 (0.9); 1.182 (0.6); 0.008 (3.2); 0.000 (57.9) |
| I-41 | 3.73 | 3.80 | Example 41: ¹H-NMR (400.0 MHz, d₆-DMSO):<br>δ = 9.277 (3.9); 8.989 (2.5); 8.456 (2.5); 8.453 (2.5); 8.345 (0.3); 8.333 (4.2); 7.954 (0.5); 4.021 (0.4); 4.003 (1.1); 3.988 (16.0); 3.949 (0.4); 3.932 (1.0); 3.916 (1.4); 3.899 (1.1); 3.883 (0.4); 3.325 (35.1); 2.892 (3.7); 2.732 (3.3); 2.672 (0.3); 2.507 (40.5); 2.503 (53.7); 2.499 (41.6); 2.330 (0.4); 1.235 (14.8); 1.219 (14.7); 0.008 (1.4); 0.000 (30.8) |
| I-42 | 3.39 | 3.46 | Example I-42: ¹H-NMR (400.0 MHz, d₆-DMSO):<br>δ = 9.881 (0.4); 9.213 (3.4); 8.238 (3.6); 8.236 (3.6); 8.136 (0.4); 8.085 (0.7); 7.683 (0.3); 7.639 (2.8); 7.634 (2.9); 7.572 (2.4); 7.552 (3.7); 7.504 (0.5); 7.499 (0.5); 7.483 (2.1); 7.478 (2.0); 7.462 (1.4); 7.457 (1.3); 6.870 (0.4); 3.779 (16.0); 3.618 (0.4); 3.608 (0.3); 3.602 (1.0); 3.585 (0.4); 3.325 (20.2); 3.098 (0.6); 3.067 (1.2); 3.048 (3.9); 3.030 (4.0); 3.016 (0.9); 3.012 (1.3); 2.877 (1.1); 2.865 (1.1); 2.676 (0.4); 2.671 (0.5); 2.667 (0.4); 2.525 (1.4); 2.520 (2.1); 2.511 (30.1); 2.507 (61.5); 2.502 (81.2); 2.498 (58.8); 2.493 (28.4); 2.333 (0.4); 2.329 (0.5); 2.324 (0.4); 2.183 (0.7); 1.776 (0.4); 1.769 (0.4); 1.760 (1.2); 1.752 (0.4); 1.744 (0.4); 1.355 (5.3); 1.245 (0.8); 1.236 (0.4); 1.226 (1.7); 1.218 (0.5); 1.208 (0.8); 1.193 (4.1); 1.175 (8.7); 1.156 (3.9); 0.146 (0.4); 0.008 (2.9); 0.000 (88.8); −0.009 (3.1); −0.150 (0.4) |
| I-43 | 2.61 | 2.69 | Example I-43: ¹H-NMR (400.0 MHz, d₆-DMSO):<br>δ = 9.259 (3.8); 8.259 (4.0); 8.123 (6.1); 8.118 (3.1); 8.107 (2.5); 8.102 (1.5); 7.945 (2.9); 7.939 (0.8); 7.929 (0.7); 7.923 (2.3); 5.757 (11.4); 3.742 (16.0); 3.600 (0.7); 3.581 (2.2); 3.563 (2.2); 3.545 (0.7); 3.329 (38.9); 2.671 (0.4); 2.525 (1.2); 2.511(23.7); 2.507 (48.0); 2.502 (63.6); 2.498 (47.5); 2.494 (24.1); 2.329 (0.4); 1.146 (3.7); 1.128 (8.2); 1.109 (3.6); 0.008 (0.3); 0.000 (9.3); −0.008 (0.4) |
| I-44 | 2.36 | 2.45 | Example I-44: ¹H-NMR (400.0 MHz, d₆-DMSO):<br>δ = 9.270 (3.8); 8.317 (0.5); 8.273 (4.1); 8.022 (2.9); 8.016 (3.1); 7.986 (2.2); 7.966 (3.6); 7.905 (2.1); 7.899 (1.9); 7.884 (1.3); 7.879 (1.2); 3.969 (16.0); 3.377 (1.0); 3.359 (1.3); 3.344 (1.9); 3.329 (150.3); 3.307 (0.6); 2.945 (1.1); 2.927 (1.2); 2.912 (1.0); 2.893 (0.9); 2.676 (0.9); 2.671 (1.2); 2.667 (0.9); 2.524 (3.1); 2.507 |

| Ex. | LOGP_NEUTRAL | LOGP_HCOOH | |
|---|---|---|---|
| I-45 | | 2.53 | (141.2); 2.502 (185.0); 2.498 (135.5); 2.333 (0.9); 2.329 (1.2); 2.325 (0.9); 1.179 (3.8); 1.160 (8.2); 1.142 (3.7); 0.008 (2.3); 0.000 (70.9); -0.009 (2.6); -0.150 (0.3)<br>Example I-45: $^1$H-NMR (400.0 MHz, d$_6$-DMSO):<br>δ = 9.295 (3.9); 8.364 (3.2); 8.342 (3.4); 8.292 (4.1); 7.347 (3.4); 7.325 (3.3); 4.015 (1.0); 3.987 (16.0); 3.922 (15.6); 3.910 (1.3); 3.733 (1.0); 3.714 (3.4); 3.695 (3.4); 3.677 (1.0); 3.506 (0.3); 3.331 (66.6); 2.672 (0.5); 2.668 (0.4); 2.507 (58.9); 2.503 (75.4); 2.498 (56.9); 2.334 (0.4); 2.329 (0.5); 2.325 (0.4); 2.087 (2.0); 1.234 (0.8); 1.203 (3.6); 1.185 (7.9); 1.166 (3.5); 0.008 (2.1); 0.000 (43.3) |
| I-46 | 2.92 | 2.98 | Example I-46: $^1$H-NMR (400.0 MHz, d$_6$-DMSO):<br>δ = 9.269 (4.1); 8.592 (1.8); 8.590 (1.9); 8.581 (1.9); 8.578 (1.8); 8.306 (4.3); 8.094 (1.7); 8.092 (1.7); 8.074 (1.9); 8.071 (1.8); 7.955 (0.8); 7.642 (1.6); 7.631 (1.6); 7.622 (1.5); 7.610 (1.5); 3.979 (16.0); 3.334 (9.6); 3.046 (1.2); 3.027 (3.8); 3.009 (3.9); 2.991 (1.3); 2.893 (4.9); 2.734 (4.4); 2.509 (22.7); 2.505 (28.6); 2.501 (21.4); 1.220 (4.2); 1.202 (8.6); 1.184 (4.1); 0.000 (4.6) |
| I-47 | 4.02 | 4.10 | Example I-47: $^1$H-NMR (400.0 MHz, d$_6$-DMSO):<br>δ = 9.308 (3.5); 8.964 (2.1); 8.961 (2.1); 8.355 (3.9); 8.353 (3.9); 8.341 (2.2); 8.338 (2.2); 8.317 (0.3); 4.030 (16.0); 3.328 (183.2); 3.184 (1.1); 3.165 (3.5); 3.147 (3.6); 3.129 (1.1); 2.676 (0.8); 2.671 (1.1); 2.667 (0.8); 2.525 (2.5); 2.520 (3.8); 2.511 (53.3); 2.507 (109.8); 2.502 (147.2); 2.498 (110.1); 2.494 (55.4); 2.334 (0.7); 2.329 (1.0); 2.325 (0.7); 1.235 (4.2); 1.217 (8.3); 1.198 (3.8); 0.146 (1.1); 0.008 (8.0); 0.000 (229.8); -0.009 (9.5); -0.150 (1.1) |
| I-48 | 2.64 | 2.70 | Example I-48: $^1$H-NMR (400.0 MHz, d$_6$-DMSO):<br>δ = 9.337 (2.2); 9.324 (2.3); 9.295 (4.0); 8.366 (2.9); 8.353 (2.8); 8.273 (4.3); 5.757 (0.8); 3.919 (16.0); 3.894 (0.7); 3.879 (1.3); 3.862 (1.3); 3.327 (92.4); 2.676 (0.6); 2.671 (0.8); 2.667 (0.6); 2.507 (88.5); 2.502 (113.9); 2.498 (86.6); 2.333 (0.6); 2.329 (0.8); 2.325 (0.6); 1.243 (3.6); 1.224 (7.4); 1.206 (3.4); 0.146 (0.6); 0.008 (6.3); 0.000 (128.4); -0.150 (0.6) |
| I-49 | 1.99 | 2.05 | Example I-49: $^1$H-NMR (400.0 MHz, d$_6$-DMSO):<br>δ = 11.328 (3.1); 9.295 (4.3); 8.532 (1.7); 8.509 (4.8); 8.487 (4.4); 8.465 (1.5); 8.318 (0.6); 8.304 (4.7); 3.876 (16.0); 3.847 (0.7); 3.658 (1.1); 3.639 (3.5); 3.621 (3.5); 3.602 (1.1); 3.331 (78.4); 2.892 (0.3); 2.676 (1.0); 2.672 (1.3); 2.668 (1.0); 2.565 (0.4); 2.507 (157.3); 2.503 (200.0); 2.498 (150.8); 2.344 (0.8); 2.334 (1.0); 2.329 (1.4); 2.169 (15.8); 1.989 (1.1); 1.234 (0.5); 1.184 (3.8); 1.175 (1.3); 1.166 (8.3); 1.148 (3.7); 0.008 (0.9); 0.000 (19.7) |
| I-50 | 2.27 | 2.39 | Example I-50: $^1$H-NMR (400.0 MHz, d$_6$-DMSO):<br>δ = 10.770 (2.6); 9.256 (3.9); 8.290 (3.7); 8.277 (4.3); 8.268 (2.5); 8.242 (0.7); 8.115 (3.0); 8.093 (2.4); 8.063 (0.4); 4.456 (1.9); 4.038 (0.6); 4.020 (0.7); 3.979 (16.0); 3.332 (83.1); 2.966 (1.2); 2.948 (4.0); 2.929 (4.1); 2.911 (1.3); 2.676 (0.4); 2.672 (0.5); 2.668 (0.4); 2.507 (62.3); 2.503 (81.2); 2.498 (61.4); 2.334 (0.4); 2.330 (0.5); 2.325 (0.4); 2.184 (1.9); 2.119 (15.2); 1.989 (2.6); 1.193 (0.7); 1.172 (4.5); 1.154 (9.1); 1.135 (4.2); 0.008 (2.6); 0.000 (55.6); -0.008 (3.1) |
| I-51 | | 2.48 | Example I-51: $^1$H-NMR (400.0 MHz, d$_6$-DMSO):<br>δ = 9.259 (4.5); 9.210 (2.4); 9.198 (2.5); 8.278 (4.7); 8.276 (4.8); 8.226 (3.2); 8.214 (3.1); 5.757 (2.5); 3.965 (0.7); 3.946 (0.8); 3.932 (0.9); 3.914 (0.8); 3.795 (16.0); 3.375 (0.6); 3.356 (0.8); 3.328 (59.8); 3.305 (0.3); 2.676 (0.4); 2.672 (0.5); 2.667 (0.4); 2.525 (1.2); 2.511 (27.2); 2.507 (56.1); 2.502 (75.0); 2.498 (55.5); 2.494 (27.5); 2.334 (0.4); 2.329 (0.5); 2.325 (0.4); 1.264 (3.7); 1.245 (7.9); 1.227 (3.8); 0.008 (1.2); 0.000 (39.0); -0.008 (1.4) |
| I-52 | 2.51 | 2.61 | Example I-52: $^1$H-NMR (601.6 MHz, CD3CN):<br>δ = 9.321 (2.5); 8.780 (3.9); 8.736 (2.6); 7.746 (3.8); 3.824 (1.3); 3.809 (16.0); 3.799 (3.9); 3.787 (1.3); 2.141 (2.3); 1.965 (10.4); 1.957 (0.4); 1.944 (3.9); 1.940 (5.2); 1.937 (3.8); 1.933 (2.0); 1.297 (3.8); 1.285 (7.6); 1.273 (3.7); 0.000 (3.3) |
| I-53 | | 3.12 | Example I-53: $^1$H-NMR (400.0 MHz, d$_6$-DMSO):<br>δ = 9.242 (3.5); 8.270 (3.7); 8.119 (0.4); 8.064 (2.9); 8.042 (3.1); 7.123 (3.3); 7.101 (3.1); 4.012 (16.0); 3.959 (0.4); 3.909 (1.6); 3.899 (3.9); 3.332 (95.1); 2.942 (1.2); 2.923 (3.9); 2.905 (3.9); 2.887 (1.3); 2.677 (0.4); 2.672 (0.6); 2.668 (0.4); 2.525 (1.6); 2.511(32.5); 2.507 (64.4); 2.503 (84.3); 2.499 (63.2); 2.334 (0.4); 2.330 (0.6); 2.325 (0.4); 1.990 (0.8); 1.175 (0.5); 1.144 (4.1); 1.126 (8.6); 1.107 (4.0); 0.008 (2.3); 0.000 (60.3); -0.008 (3.0) |
| I-54 | 3.07 | 3.16 | Example I-54: $^1$H-NMR (400.0 MHz, d$_6$-DMSO):<br>δ = 9.293 (3.9); 8.987 (2.7); 8.490 (2.7); 8.335 (4.1); 5.757 (0.6); 4.713 (1.2); 4.699 (2.4); 4.685 (1.2); 4.595 (1.1); 4.581 (2.3); 4.567 (1.3); 4.041 (16.0); 3.581 (1.1); 3.567 (2.2); 3.553 (1.1); 3.521 (1.2); 3.507 (2.2); 3.493 (1.1); 3.327 (105.4); 2.671 (0.8); 2.506 (88.1); 2.502 (120.1); 2.498 (96.8); 2.333 (0.6); 2.329 (0.8); 1.234 (0.4); 0.146 (0.4); 0.008 (2.7); 0.000 (84.4); -0.150 (0.4) |
| I-55 | 3.01 | 3.12 | Example I-55: $^1$H-NMR (400.0 MHz, d$_6$-DMSO):<br>δ = 8.956 (3.9); 8.953 (4.0); 8.942 (2.0); 8.940 (2.0); 8.317 (2.1); 7.904 (3.7); 7.902 (3.7); 3.950 (16.0); 3.332 (109.0); 3.172 (1.0); 3.154 (3.3); 3.135 (3.4); 3.117 (1.0); 2.676 (0.3); 2.672 (0.5); 2.667 (0.4); 2.525 (1.2); 2.520 (1.8); 2.512 (26.2); 2.507 (53.9); 2.503 (71.3); 2.498 (52.0); 2.494 (25.3); 2.334 (0.3); 2.330 (0.5); 2.325 (0.4); 1.251 (0.5); 1.232 (5.1); 1.214 (7.9); 1.195 (3.5); 1.103 (0.3); 0.000 (6.1) |
| I-56 | 1.56 | 1.61 | Example I-56: $^1$H-NMR (400.0 MHz, d$_6$-DMSO):<br>δ = 9.502 (3.9); 9.497 (3.4); 9.306 (4.1); 8.900 (4.0); 8.895 (3.4); 8.645 (1.9); 8.322 (4.5); 8.057 (1.9); 3.892 (16.0); 3.843 (1.3); 3.825 (3.8); 3.806 (3.7); 3.788 (1.1); 3.332 (180.7); 2.676 (0.9); 2.672 (1.1); 2.667 (0.8); 2.507 (135.9); 2.503 |

-continued

| Ex. | LOGP_NEUTRAL | LOGP_HCOOH | |
|---|---|---|---|
| I-57 | 2.82 | 2.89 | (156.6); 2.498 (111.5); 2.334 (0.9); 2.330 (1.0); 2.325 (0.7); 1.298 (0.5); 1.259 (1.0); 1.235 (5.5); 1.217 (8.5); 1.198 (3.8); 0.000 (14.4); −0.062 (0.6) Example I-57: $^1$H-NMR (400.0 MHz, d$_6$-DMSO): δ = 9.596 (2.3); 9.593 (2.2); 9.330 (3.8); 9.320 (0.5); 8.830 (2.3); 8.826 (2.2); 8.353 (4.1); 4.994 (1.0); 4.982 (1.5); 4.969 (1.1); 4.877 (1.0); 4.865 (1.5); 4.852 (1.2); 4.493 (1.1); 4.480 (1.5); 4.468 (1.0); 4.427 (1.2); 4.414 (1.5); 4.402 (1.0); 3.957 (16.0); 3.947 (1.6); 3.919 (0.4); 3.813 (0.3); 3.328 (182.7); 2.676 (0.7); 2.671 (1.0); 2.667 (0.7); 2.663 (0.4); 2.524 (3.6); 2.511 (61.5); 2.507 (120.1); 2.502 (156.5); 2.498 (114.9); 2.493 (57.0); 2.333 (0.7); 2.329 (1.0); 2.325 (0.7); 2.074 (0.5); 1.235 (0.6); 0.008 (2.3); 0.000 (63.1); −0.008 (2.5) |
| I-58 | 2.19 | | Example I-58: $^1$H-NMR (400.0 MHz, d$_6$-DMSO): δ = 9.553 (2.2); 9.550 (2.2); 9.320 (3.9); 8.786 (2.4); 8.781 (2.4); 8.336 (4.1); 5.755 (1.0); 5.119 (1.2); 5.106 (2.9); 5.093 (1.3); 4.066 (1.6); 4.052 (3.3); 4.038 (2.1); 3.919 (16.0); 3.869 (1.1); 3.855 (2.7); 3.842 (2.5); 3.828 (0.9); 3.400 (0.4); 3.393 (0.4); 3.384 (0.5); 3.345 (268.1); 3.309 (0.6); 2.672 (0.4); 2.526 (1.1); 2.512 (22.7); 2.508 (46.1); 2.503 (61.2); 2.499 (45.2); 2.494 (22.6); 2.330 (0.4); 0.000 (0.6) |
| I-59 | 2.31 | 2.41 | Example I-59: $^1$H-NMR (600.1 MHz, CD3CN): δ = 9.085 (2.6); 8.843 (1.4); 8.842 (1.5); 8.333 (1.7); 8.331 (1.6); 8.165 (2.9); 5.447 (1.4); 3.979 (16.0); 3.725 (0.9); 3.715 (2.8); 3.705 (2.9); 3.695 (1.0); 3.459 (0.9); 3.449 (1.8); 3.439 (0.8); 3.177 (2.4); 3.167 (4.3); 3.157 (2.2); 2.145 (5.7); 1.957 (0.5); 1.953 (0.6); 1.949 (3.0); 1.945 (5.2); 1.941 (7.5); 1.937 (5.0); 1.933 (2.5) |
| I-60 | 1.76 | 1.77 | Example I-60: $^1$H-NMR (400.0 MHz, d$_6$-DMSO): δ = 9.262 (4.0); 8.968 (3.2); 8.963 (3.3); 8.415 (1.6); 8.354 (3.0); 8.350 (3.1); 8.303 (4.3); 7.862 (1.6); 4.008 (16.0); 3.331 (33.2); 3.113 (1.1); 3.095 (3.7); 3.076 (3.8); 3.058 (1.2); 2.508 (35.4); 2.504 (46.2); 2.499 (34.8); 1.246 (4.0); 1.228 (8.5); 1.209 (3.9); 0.008 (1.7); 0.000 (46.1); −0.008 (2.2) |
| I-61 | 2.63 | 2.71 | Example I-61: $^1$H-NMR (400.0 MHz, d$_6$-DMSO): δ = 9.343 (3.7); 8.973 (1.6); 8.969 (1.8); 8.961 (1.8); 8.957 (1.8); 8.559 (1.6); 8.555 (1.7); 8.539 (1.8); 8.535 (1.8); 8.347 (4.0); 8.345 (4.0); 7.941 (1.7); 7.929 (1.6); 7.921 (1.6); 7.909 (1.6); 4.320 (16.0); 3.561 (1.0); 3.542 (1.0); 3.528 (1.1); 3.509 (1.1); 3.490 (0.3); 3.330 (33.2); 3.048 (1.1); 3.030 (1.2); 3.015 (1.0); 2.997 (1.0); 2.677 (0.4); 2.672 (0.5); 2.668 (0.4); 2.525 (1.3); 2.507 (56.6); 2.503 (75.2); 2.499 (56.4); 2.334 (0.4); 2.330 (0.5); 2.325 (0.4); 1.301 (3.8); 1.282 (8.2); 1.264 (3.7); 0.146 (0.5); 0.008 (4.0); 0.000 (110.8); −0.008 (5.6); −0.150 (0.5) |
| I-62 | 2.15 | 2.17 | Example I-62: $^1$H-NMR (400.0 MHz, d$_6$-DMSO): δ = 9.207 (3.4); 8.318 (0.5); 8.194 (3.7); 8.192 (3.6); 8.062 (1.6); 8.059 (1.7); 8.042 (2.2); 8.039 (2.2); 7.947 (1.8); 7.928 (2.7); 7.908 (1.6); 7.735 (2.0); 7.732 (2.1); 7.716 (1.8); 7.713 (1.7); 3.742 (16.0); 3.593 (1.0); 3.574 (3.5); 3.556 (3.6); 3.537 (1.2); 3.329 (74.8); 2.676 (0.7); 2.671 (0.9); 2.667 (0.7); 2.662 (0.4); 2.525 (2.4); 2.520 (3.6); 2.511 (50.5); 2.507 (105.6); 2.502 (140.5); 2.498 (101.4); 2.493 (48.8); 2.334 (0.6); 2.329 (0.9); 2.324 (0.6); 2.086 (0.7); 1.235 (1.3); 1.184 (4.0); 1.166 (9.0); 1.147 (3.9); 1.140 (0.6); 0.146 (0.7); 0.008 (5.0); 0.000 (161.5); −0.009 (5.9); −0.150 (0.7) |
| I-63 | 3.62 | 3.75 | Example I-63: $^1$H-NMR (400.0 MHz, d$_6$-DMSO): δ = 9.396 (5.6); 8.728 (2.2); 8.723 (2.3); 8.416 (4.1); 8.414 (3.9); 8.318 (0.5); 4.362 (16.0); 3.635 (0.9); 3.617 (1.0); 3.602 (1.1); 3.583 (1.0); 3.332 (165.3); 3.134 (1.0); 3.116 (1.2); 3.101 (1.0); 3.083 (1.0); 2.676 (0.8); 2.672 (1.1); 2.667 (0.8); 2.525 (2.6); 2.511 (62.5); 2.507 (126.3); 2.503 (165.5); 2.498 (121.7); 2.494 (60.8); 2.334 (0.8); 2.329 (1.1); 2.325 (0.8); 1.327 (3.7); 1.308 (8.1); 1.290 (3.6); 0.146 (0.4); 0.008 (3.1); 0.000 (96.0); −0.008 (4.1); −0.150 (0.4) |
| I-64 | 3.95 | 3.93 | Example I-64: $^1$H-NMR (400.0 MHz, d$_6$-DMSO): δ = 9.275 (2.6); 9.271 (2.5); 8.943 (4.3); 8.584 (2.6); 8.580 (2.6); 8.318 (0.5); 7.701 (3.0); 7.680 (3.9); 7.548 (3.8); 7.527 (3.0); 7.410 (4.6); 3.890 (16.0); 3.329 (75.4); 3.140 (1.3); 3.122 (4.2); 3.104 (4.3); 3.086 (1.4); 2.676 (0.9); 2.671 (1.2); 2.667 (0.9); 2.507 (140.3); 2.502 (179.9); 2.498 (134.5); 2.334 (0.9); 2.329 (1.2); 2.325 (0.9); 1.281 (4.6); 1.263 (9.7); 1.245 (4.5); 0.146 (0.4); 0.008 (3.6); 0.000 (84.0); −0.150 (0.4) |
| I-65 | 4.31 | 4.37 | Example I-65: $^1$H-NMR (400.0 MHz, d$_6$-DMSO): δ = 9.217 (3.1); 9.076 (4.1); 9.074 (4.1); 8.959 (2.3); 8.956 (2.3); 8.334 (2.3); 8.318 (1.7); 8.288 (3.7); 8.211 (4.1); 8.209 (4.1); 5.758 (1.1); 4.005 (16.0); 3.328 (226.4); 3.189 (1.1); 3.171 (3.5); 3.153 (3.6); 3.134 (1.1); 2.676 (2.7); 2.671 (3.8); 2.667 (2.8); 2.525 (9.3); 2.520 (14.6); 2.511 (211.4); 2.507 (434.4); 2.502 (573.8); 2.498 (421.2); 2.493 (209.9); 2.333 (2.7); 2.329 (3.7); 2.324 (2.8); 1.258 (0.3); 1.243 (4.1); 1.225 (8.8); 1.206 (3.9); 1.148 (0.3); 0.146 (1.3); 0.008 (9.7); 0.000 (308.8); −0.008 (13.1); −0.150 (1.4) |
| I-66 | 3.42 | 3.50 | Example I-66: $^1$H-NMR (400.0 MHz, d$_6$-DMSO): δ = 9.243 (3.5); 8.317 (0.4); 8.274 (3.7); 8.069 (2.9); 8.047 (3.1); 7.116 (3.3); 7.094 (3.2); 4.017 (0.4); 4.000 (16.0); 3.893 (15.8); 3.329 (74.5); 2.884 (2.3); 2.867 (3.7); 2.848 (2.4); 2.676 (0.7); 2.671 (0.9); 2.667 (0.7); 2.525 (2.3); 2.511 (50.8); 2.507 (105.0); 2.502 (139.6); 2.498 (102.9); 2.494 (51.4); 2.334 (0.6); 2.329 (0.9); 2.325 (0.7); 1.496 (1.2); 1.478 (2.4); 1.460 (2.5); 1.442 (1.4); 0.875 (4.2); 0.857 (8.4); 0.838 (3.7); 0.008 (0.8); 0.000 (28.2); −0.008 (1.2) |
| I-67 | 2.70 | 2.75 | Example I-67: $^1$H-NMR (400.0 MHz, d$_6$-DMSO): δ = 10.028 (0.5); 9.850 (0.4); 9.268 (0.7); 9.248 (3.0); 8.317 (1.0); 8.302 (0.7); |

-continued

| Ex. | LOGP_NEUTRAL | LOGP_HCOOH | |
|---|---|---|---|
| | | | 8.262 (3.1); 8.236 (0.6); 8.194 (0.5); 8.119 (1.3); 8.097 (0.7); 8.026 (2.6); 8.004 (2.6); 7.996 (0.5); 7.978 (0.6); 7.181 (0.8); 7.159 (0.6); 7.133 (2.8); 7.111 (2.7); 4.442 (2.5); 4.071 (13.8); 4.017 (3.3); 4.014 (3.6); 3.959 (1.9); 3.910 (16.0); 3.329 (346.6); 2.881 (1.4); 2.869 (1.4); 2.676 (1.7); 2.671 (2.3); 2.667 (1.7); 2.525 (5.8); 2.511(128.4); 2.507 (263.1); 2.502 (348.1); 2.498 (256.2); 2.494 (127.6); 2.422 (14.2); 2.334 (1.7); 2.329 (2.3); 2.325 (1.7); 1.989 (0.9); 1.234 (0.3); 1.175 (0.5); 0.146 (0.4); 0.008 (3.2); 0.000 (99.9); −0.008 (3.8); −0.150 (0.5) |
| I-68 | 2.46 | 2.50 | Example I-68: $^1$H-NMR (400.0 MHz, d$_6$-DMSO): δ = 9.319 (4.1); 9.142 (1.6); 9.139 (1.9); 9.130 (1.8); 9.126 (1.9); 8.582 (1.6); 8.578 (1.8); 8.562 (1.9); 8.558 (1.9); 8.328 (4.3); 8.024 (1.7); 8.012 (1.7); 8.003 (1.6); 7.991 (1.6); 3.870 (16.0); 3.802 (1.0); 3.783 (3.5); 3.765 (3.6); 3.746 (1.1); 3.333 (44,0); 2.676 (0.3); 2.672 (0.5); 2.668 (0.4); 2.507 (56.6); 2.503 (74.8); 2.499 (56.9); 2.330 (0.5); 1.209 (3.7); 1.191 (8.1); 1.172 (3.6); 0.008 (1.1); 0.000 (28.7) |
| I-69 | 4.32 | 4.37 | Example I-69: $^1$H-NMR (400.0 MHz, d$_6$-DMSO): δ = 9.080 (4.3); 9.078 (4.2); 8.959 (2.4); 8.956 (2.4); 8.873 (1.8); 8.871 (2.0); 8.867 (2.1); 8.865 (1.8); 8.337 (2.4); 8.334 (2.4); 8.181 (4.2); 8.180 (4.2); 7.062 (2.5); 7.056 (2.5); 4.007 (16.0); 3.330 (22.5); 3.189 (1.1); 3.170 (3.7); 3.152 (3.7); 3.133 (1.2); 2.677 (0.3); 2.672 (0.5); 2.668 (0.3); 2.526 (1.2); 2.512 (26.3); 2.508 (53.3); 2.503 (70.1); 2.499 (51.8); 2.495 (26.3); 2.330 (0.4); 2.326 (0.3); 2.077 (0.6); 1.244 (4.0); 1.225 (8.7); 1.207 (3.9); 0.008 (1.3); 0.000 (37.3); −0.008 (1.8) |
| I-70 | 3.24 | 3.29 | Example I-70: $^1$H-NMR (400.0 MHz, d$_6$-DMSO): δ = 9.272 (4.0); 9.057 (2.0); 9.044 (2.1); 8.309 (4.2); 8.135 (2.8); 8.122 (2.7); 4.021 (0.4); 3.846 (16.0); 3.328 (22.9); 2.736 (1.1); 2.717 (3.4); 2.699 (3.5); 2.680 (1.3); 2.507 (37.7); 2.503 (49.4); 2.499 (37.9); 1.990 (1.3); 1.397 (1.1); 1.193 (0.3); 1.176 (0.7); 1.158 (0.4); 0.985 (4.0); 0.966 (8.1); 0.948 (3.8); 0.008 (1.7); 0.000 (44.7); −0.008 (2.1) |
| I-71 | | 2.93 | Example I-71: $^1$H-NMR (400.0 MHz, d$_6$-DMSO): δ = 9.293 (4.1); 8.368 (3.1); 8.345 (3.3); 8.299 (4.3); 7.342 (3.4); 7.320 (3.2); 5.758 (0.9); 4.017 (0.4); 3.985 (16.0); 3.918 (15.5); 3.716 (2.2); 3.701 (1.9); 3.696 (2.5); 3.692 (1.8); 3.677 (2.2); 3.330 (25.0); 2.676 (0.4); 2.672 (0.5); 2.668 (0.4); 2.507 (54.4); 2.503 (69.4); 2.499 (51.7); 2.330 (0.5); 2.326 (0.3); 1.668 (1.1); 1.649 (2.0); 1.630 (2.0); 1.611 (1.2); 1.235 (0.7); 0.993 (4.1); 0.974 (8.2); 0.956 (3.7); 0.000 (2.4) |
| I-72 | 2.26 | 2.32 | Example I-72: $^1$H-NMR (400.0 MHz, d$_6$-DMSO): δ = 9.581 (3.0); 9.576 (3.0); 9.312 (4.1); 9.070 (3.3); 9.065 (3.2); 8.716 (1.0); 8.704 (0.9); 8.335 (4.3); 8.091 (0.4); 7.660 (0.6); 7.645 (0.8); 7.641 (0.7); 7.626 (0.6); 3.916 (16.0); 3.872 (1.3); 3.854 (3.8); 3.835 (3.9); 3.817 (1.4); 3.736 (0.6); 3.694 (0.7); 3.626 (0.8); 3.613 (0.8); 2.671 (1.0); 2.506 (105.6); 2.502 (135.4); 2.498 (103.6); 2.333 (0.7); 2.329 (0.9); 1.989 (0.7); 1.298 (0.6); 1.252 (4.0); 1.234 (9.7); 1.215 (3.9); 1.193 (0.3); 1.175 (0.5); 0.000 (3.0) |
| I-73 | 2.20 | 2.25 | Example I-73: $^1$H-NMR (400.0 MHz, d$_6$-DMSO): δ = 9.297 (3.6); 9.268 (0.9); 9.255 (0.6); 9.208 (0.4); 8.404 (3.2); 8.382 (3.4); 8.317 (0.4); 8.298 (3.9); 8.238 (0.6); 8.119 (0.8); 8.106 (0.4); 8.097 (0.9); 8.084 (0.4); 8.024 (0.5); 8.022 (0.5); 7.996 (0.4); 7.975 (0.4); 7.352 (3.6); 7.330 (3.5); 7.181 (0.8); 7.159 (0.8); 7.087 (0.4); 7.069 (0.4); 7.067 (0.4); 5.758 (2.8); 4.564 (1.5); 4.442 (3.0); 4.115 (0.7); 4.015 (4.7); 3.988 (16.0); 3.931 (15.4); 3.909 (3.9); 3.568 (0.8); 3.544 (14.4); 3.331 (131.8); 2.676 (0.7); 2.672 (0.9); 2.667 (0.7); 2.525 (2.7); 2.511 (52.5); 2.507 (106.0); 2.503 (139.4); 2.498 (102.4); 2.494 (51.6); 2.334 (0.6); 2.329 (0.9); 2.325 (0.7); 1.259 (0.5); 1.234 (1.5); 0.000 (5.6) |
| I-74 | 3.36 | 3.49 | Example I-74: $^1$H-NMR (601.6 MHz, CD3CN): δ = 8.905 (3.0); 8.903 (3.0); 8.852 (1.6); 8.850 (1.6); 8.500 (1.9); 8.313 (1.5); 8.311 (2.1); 8.309 (1.4); 8.183 (1.7); 8.181 (1.7); 7.962 (3.4); 7.961 (3.4); 4.001 (16.0); 3.940 (0.4); 3.124 (1.1); 3.111 (3.4); 3.099 (3.5); 3.087 (1.2); 2.639 (0.7); 2.184 (55.7); 2.109 (1.2); 2.005 (2.2); 1.998 (195.7); 1.989 (2.7); 1.985 (1.8); 1.981 (10.0); 1.977 (18.2); 1.973 (26.5); 1.969 (18.0); 1.965 (9.0); 1.882 (1.2); 1.419 (0.4); 1.404 (0.7); 1.373 (0.6); 1.330 (4.1); 1.318 (9.0); 1.309 (1.6); 1.305 (5.2); 1.301 (3.4); 0.914 (0.6) |
| I-75 | 2.84 | 2.94 | Example I-75: $^1$H-NMR (400.0 MHz, d$_6$-DMSO): δ = 9.582 (2.6); 9.107 (4.5); 8.797 (2.6); 8.794 (2.8); 8.761 (3.5); 8.668 (2.9); 8.361 (4.6); 8.314 (0.3); 5.754 (2.9); 3.939 (1.0); 3.920 (3.5); 3.897 (16.0); 3.883 (1.4); 3.316 (65.0); 2.675 (0.8); 2.671 (1.1); 2.666 (0.9); 2.506 (121.1); 2.502 (165.0); 2.497 (131.6); 2.333 (0.7); 2.328 (1.1); 2.324 (0.9); 1.988 (0.8); 1.272 (3.7); 1.253 (8.2); 1.235 (4.5); 1.175 (0.4); 0.146 (0.5); 0.008 (3.6); 0.000 (102.8); −0.150 (0.5) |
| I-76 | 3.73 | 3.84 | Example I-76: $^1$H-NMR (601.6 MHz, CD3CN): δ = 9.334 (1.1); 9.333 (1.2); 9.331 (1.2); 9.329 (1.1); 9.015 (1.4); 9.014 (1.7); 8.867 (2.5); 8.865 (2.3); 8.751 (1.2); 8.750 (1.3); 8.747 (1.3); 8.287 (2.6); 8.286 (2.3); 8.036 (1.9); 5.446 (0.6); 3.879 (0.9); 3.867 (16.0); 3.855 (3.0); 3.842 (0.9); 2.129 (16.5); 1.964 (0.3); 1.955 (0.9); 1.951 (1.2); 1.947 (9.5); 1.943 (17.4); 1.939 (24.5); 1.935 (16.4); 1.931 (8.6); 1.313 (3.1); 1.300 (6.6); 1.288 (3.1); 1.270 (0.6); 0.005 (0.6); 0.000 (19.1); −0.006 (0.7) |
| I-77 | 3.81 | 3.90 | Example I-77: $^1$H-NMR (601.6 MHz, CD3CN): δ = 9.333 (1.3); 9.332 (1.5); 9.330 (1.5); 8.871 (3.2); 8.869 (3.1); 8.750 (1.6); 8.748 (1.6); 8.736 (1.3); 8.734 (1.4); 8.731 (1.4); 8.730 (1.2); 8.250 (3.0); 8.249 (3.0); 6.869 (1.7); 6.865 (1.7); 5.446 (0.7); 3.884 (1.1); 3.871 (4.7); 3.869 (16.0); |

| Ex. | LOGP_NEUTRAL | LOGP_HCOOH |
|---|---|---|

-continued 3.859 (3.6); 3.847 (1.1); 2.133 (5.1); 1.956 (0.3); 1.952 (0.4); 1.948 (3.5); 1.944 (6.3); 1.940 (9.0); 1.936 (6.1); 1.932 (3.2); 1.314 (3.5); 1.302 (7.5); 1.290 (3.6); 1.285 (0.4); 1.267 (0.5); 0.000 (5.6)

Use Examples

*Ctenocephalides felis*—In Vitro Contact Test

For the coating of the test tubes, 9 mg of active ingredient are first dissolved in 1 ml of acetone p.a. and then diluted to the desired concentration with acetone p.a. 250 µl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 $cm^2$, given homogeneous distribution, an area-based dose of 5 µg/$cm^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/$cm^2$. 100% efficacy means that all the fleas were dead or moribund. 0% efficacy means that no fleas were harmed.

In this test, for example, the following compounds from the preparation examples show an efficacy of 100% at an application rate of 5 µg/$cm^2$: I-18, I-21

*Boophilus microplus*—Injection Test (BOOPMI Inj)

Solvent: dimethyl sulphoxide

To produce an appropriate active ingredient formulation, 10 mg of active ingredient are mixed with 0.5 ml of solvent and the concentrate is diluted with solvent to the desired concentration.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 80% at an application rate of 20 µg/animal: I-21

*Ctenocephalides felis*—Oral Test (CTECFE)

Solvent: dimethyl sulphoxide

For the purpose of producing an appropriate active ingredient formulation, 10 mg of active ingredient are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 90% at an application rate of 100 ppm: I-21

*Lucilia cuprina* Test (LUCICU)

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active ingredient preparation of the desired concentration.

After 2 days, the kill in % is determined. 100% means that all the larvae have been killed; 0% means that none of the larvae have been killed.

In this test, for example, the following compounds from the preparation examples show an efficacy of 100% at an application rate of 100 ppm: I-18, I-21

*Musca domestica* Test (MUSCDO)

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 95% at an application rate of 20 ppm: I-21

*Myzus persicae*—Spray Test (MYZUPE)

Solvent: 78 parts by weight of acetone 1.5 parts by weight of dimethylformamide

Emulsifier: alkylaryl poly glycol ether

To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the efficacy in % is determined. 100% means that all the aphids have been killed; 0% means that none of the aphids have been killed.

In this test, for example, the following compounds from the preparation examples show an efficacy of 100% at an application rate of 500 g/ha: I-10, I-13, I-18, I-22, I-23, I-24, I-43, I-44, I-48, I-52

In this test, for example, the following compounds from the preparation examples show an efficacy of 90% at an application rate of 500 g/ha: I-4, I-12, I-14, I-17, I-18, I-19, I-21, I-38, I-42, I-45, I-46, I-49, I-50, I-51, I-56, I-61, I-68

In this test, for example, the following compounds from the preparation examples show an efficacy of 90% at an application rate of 20 g/ha: I-39

*Phaedon cochleariae*—Spray Test (PHAECO)
Solvent: 78.0 parts by weight of acetone
1.5 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: I-2, I-3, I-4, I-5, I-10, I-12, I-13, I-14, I-18, I-19, I-21, I-22, I-24, I-25, I-26, I-28, I-29, I-31, I-36, I-37, I-38, I-39, I-41, I-42, I-43, I-44, I-45, I-46, I-47, I-48, I-49, I-50, I-51, I-52, I-53, I-54, I-55, I-61, I-68, I-73

In this test, for example, the following compounds from the preparation examples show an efficacy of 83% at an application rate of 500 g/ha: I-30, I-63

In this test, for example, the following compounds from the preparation examples show an efficacy of 100% at an application rate of 100 g/ha: I-11

In this test, for example, the following compounds from the preparation examples show an efficacy of 83% at an application rate of 100 g/ha: I-17

*Spodoptera frugiperda*—Spray Test (SPODFR)
Solvent: 78.0 parts by weight of acetone
1.5 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: I-2, I-21, I-26, I-37, I-39, I-42, I-46, I-47, I-54, I-61, I-63, I-68

In this test, for example, the following compounds from the preparation examples show an efficacy of 83% at an application rate of 500 g/ha: I-14, I-19, I-48

*Tetranychus urticae*—Spray Test, OP-Resistant (TETRUR)
Solvent: 78.0 parts by weight of acetone
1.5 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that none of the spider mites have been killed.

In this test, for example, the following compound from the preparation examples shows an efficacy of 100% at an application rate of 500 g/ha: I-68

In this test, for example, the following compounds from the preparation examples show an efficacy of 90% at an application rate of 500 g/ha: I-2, I-13, I-19, I-22, I-28, I-42, I-44, I-53

In this test, for example, the following compound from the preparation examples shows an efficacy of 90% at an application rate of 100 g/ha: I-48

*Myzus persicae*—Spray Test (MYZUPE)
Solvent: 7 parts by weight of dimethylformamide
Emulsifier: alkylaryl poly glycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (*Capsicum annuum*) heavily infested by the green peach aphid (*Myzus persicae*) are treated by spraying with the active ingredient formulation in the desired concentration.

After 6 days, the kill in % is determined. 100% means that all the aphids have been killed; 0% means that no aphids have been killed.

In this test, for example, the following compound from the preparation examples shows an efficacy of 97% at an application rate of 100 ppm: I-11

*Meloidogyne incognita* Test
Solvent: 125.0 parts by weight of acetone

To produce a suitable active ingredient formulation, 1 part by weight of active ingredient is mixed with the stated amount of solvent and the concentrate is diluted with water to the desired concentration.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compound from the preparation examples shows an efficacy of 100% at an application rate of 20 ppm: I-68

Comparative Examples

*Myzus persicae*—Contact Test (MYZUPE c)
Solvent: 7 parts by weight of dimethylformamide
Emulsifier: alkylaryl poly glycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

One-leaved bell pepper plants (*Capsicum annuum*) heavily infested by the green peach aphid (*Myzus persicae*) are treated by spraying the underside of the leaf with the active ingredient formulation in the desired concentration.

After the desired time, the kill in % is determined. 100% means that all the aphids have been killed and 0% means that none of the aphids have been killed.

In this test, for example, the following compound from the preparation examples shows good efficacy compared to the known compound from WO2013018928 (see table):

*Myzus persicae*—Translaminar Test (MYZUPE t)
Solvent: 7 parts by weight of dimethylformamide
Emulsifier: alkylaryl poly glycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

One-leaved bell pepper plants (*Capsicum annuum*) heavily infested by the green peach aphid (*Myzus persicae*) are treated by spraying the top side of the leaf with the active ingredient formulation in the desired concentration.

After the desired time, the kill in % is determined. 100% means that all the aphids have been killed and 0% means that none of the aphids have been killed.

In this test, for example, the following compound from the preparation examples shows good efficacy compared to the known compound from WO2013018928 (see table):

*Aphis gossypii*—Contact Test (APHIGO c)
Solvent: 7 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

One-leaved cotton plants (*Gossypium hirsutum*) heavily infested by the cotton aphid (*Aphis gossypii*) are treated by spraying the underside of the leaf with the active ingredient formulation in the desired concentration.

After the desired time, the kill in % is determined. 100% means that all the aphids have been killed and 0% means that none of the aphids have been killed.

In this test, for example, the following compound from the preparation examples shows good efficacy compared to the known compound from WO2013018928 (see table):

*Aphis gossypii*—Translaminar Test (APHIGO t)
Solvent: 7 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

One-leaved cotton plants (*Gossypium hirsutum*) heavily infested by the cotton aphid (*Aphis gossypii*) are treated by spraying the top side of the leaf with the active ingredient formulation in the desired concentration.

After the desired time, the kill in % is determined. 100% means that all the aphids have been killed and 0% means that none of the aphids have been killed.

In this test, for example, the following compound from the preparation examples shows good efficacy compared to the known compound from WO2013018928 (see table):

*Nephotettix cincticeps* Test (NEPHCI)
Solvent: 7 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

Rice plants (*Oryza sativa*, var. *Balilla*) are treated by spraying with the active ingredient formulation in the desired concentration and then populated with larvae of the green rice leafhopper (*Nephotettix cincticeps*).

After the desired time, the kill in % is determined. 100% means that all leafhoppers have been killed; 0% means that none of the leafhoppers have been killed.

In this test, for example, the following compound from the preparation examples shows good efficacy compared to the known compound from WO2013018928 (see table):

*Nilaparvata lugens* Test (NILALU)
Solvent: 7 parts by weight of dimethylformamide
Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

Rice plants (*Oryza sativa*, var. *Balilla*) are treated by spraying with the active ingredient formulation in the desired concentration and then populated with L3 larvae of the brown planthopper (*Nilaparvata lugens*).

After the desired time, the feeding damage in % is determined. 100% means that no feeding damage is found; 0% means that the feeding damage to the treated plant corresponds to that of the untreated control.

In this test, for example, the following compound from the preparation examples shows good efficacy compared to the known compound from WO2013018928 (see table):

| Substance | Structure | Animal species | Concentration | % efficacy | dat* |
|---|---|---|---|---|---|
| Ex. I-21 | 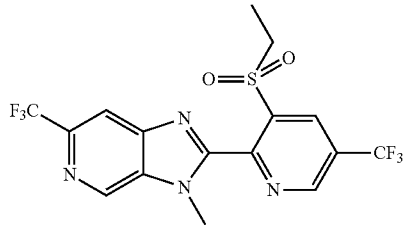 [SMILES: CCS(=O)(=O)c1cc(C(F)(F)F)cnc1-c1nc2cc(C(F)(F)F)ncc2n1C] | MYZUPE c | 2.4 g/ha | 85 | 14 dat |
| | | MYZUPE t | 12 g/ha | 98 | 14 dat |
| | | MYZUPE t | 2.4 g/ha | 90 | 14 dat |
| | | APHIGO c | 2.4 g/ha | 98 | 7 dat |
| | | APHIGO t | 2.4 g/ha | 65 | 7 dat |
| | | NEPHCI | 0.16 ppm | 90 | 14 dat |
| | | NEPHCI | 0.16 ppm | 95 | 21 dat |
| | | NEPHCI | 0.16 ppm | 100 | 34 dat |
| | | NILALU | 4 ppm | 90 | 21 dat |
| | | NILALU | 4 ppm | 100 | 28 dat |
| Ex. 5 known from WO2013018928 | 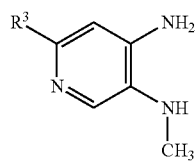 | MYZUPE c | 2.4 g/ha | 50 | 14 dat |
| | | MYZUPE t | 12 g/ha | 0 | 14 dat |
| | | MYZUPE t | 2.4 g/ha | 0 | 14 dat |
| | | APHIGO c | 2.4 g/ha | 15 | 7 dat |
| | | APHIGO t | 2.4 g/ha | 0 | 7 dat |
| | | NEPHCI | 0.16 ppm | 0 | 14 dat |
| | | NEPHCI | 0.16 ppm | 0 | 21 dat |
| | | NEPHCI | 0.16 ppm | 0 | 34 dat |
| | | NILALU | 4 ppm | 35 | 21 dat |
| | | NILALU | 4 ppm | 20 | 28 dat |

*dat = days after treatment (days)

What is claimed:

1. A compound of formula (IIa)

(IIa)

wherein
$R^3$ is $(C_1$-$C_4)$haloalkyl, $(C_1$-$C_4)$haloalkoxy, $(C_1$-$C_4)$haloalkylthio, $(C_1$-$C_4)$haloalkylsulphinyl or $(C_1$-$C_4)$haloalkylsulphonyl, where $R^3$ is not $CF_3$ or $CHF_2$.

2. The compound of the formula (IIa) according to claim 1 wherein
$R^3$ is $CH_2F$, $C_2H_4F$, $C_2H_3F_2$, $C_2H_2F_3$, $C_2HF_4$, $C_2F_5$, n-$C_3F_7$, i-$C_3F_7$, $OCH_2F$, $SCH_2F$, $SOCH_2F$, $SO_2CH_2F$, $OCHF_2$, $SCHF_2$, $SOCHF_2$, $SO_2CHF_2$, $OCF_3$, $OCF_2Cl$, $OCFCl_2$, $SCF_3$, $SOCF_3$, $SO_2CF_3$, $OC_2H_4F$, $SC_2H_4F$, $SOC_2H_4F$, $SO_2C_2H_4F$, $OC_2H_3F_2$, $SC_2H_3F_2$, $SOC_2H_3F_2$, $SO_2C_2H_3F_2$, $OC_2H_2F_3$, $SC_2H_2F_3$, $SOC_2H_2F_3$, $SO_2C_2H_2F_3$, $OC_2HF_4$, $SC_2HF_4$, $SOC_2HF_4$, $SO_2C_2HF_4$, $OC_2F_5$, $SC_2F_5$, $SOC_2F_5$, $SO_2C_2F_5$, n-$OC_3F_7$, n-$SC_3F_7$, n-$SOC_3F_7$, n-$SO_2C_3F_7$, i-$OC_3F_7$, i-$SC_3F_7$, i-$SOC_3F_7$ or i-$SO_2C_3F_7$.

3. The compound of the formula (IIa) according to claim 1 wherein
$R^3$ is $CH_2F$, $OCF_3$, $C_2H_4F$, $C_2H_3F_2$, $C_2H_2F_3$, $C_2HF_4$, $C_2F_5$, $SCF_3$, $SOCF_3$ or $SO_2CF_3$.

4. The compound of the formula (IIa) according to claim 1, wherein $R^3$ is $C_2F_5$.

5. The compound of the formula (IIa) according to claim 1, wherein $R^3$ is $CH_2F$.

6. The compound of the formula (IIa) according to claim 1, wherein $R^3$ is $OCF_3$.

7. The compound of the formula (IIa) according to claim 1, wherein $R^3$ is $C_2H_4F$.

8. The compound of the formula (IIa) according to claim 1, wherein $R^3$ is $C_2H_3F_2$.

9. The compound of the formula (IIa) according to claim 1, wherein $R^3$ is $C_2H_2F_3$.

10. The compound of the formula (IIa) according to claim 1, wherein $R^3$ is $C_2HF_4$.

11. The compound of the formula (IIa) according to claim 1, wherein $R^3$ is $SCF_3$.

12. The compound of the formula (IIa) according to claim 1, wherein $R^3$ is $SOCF_3$.

13. The compound of the formula (IIa) according to claim 1, wherein $R^3$ is $SO_2CF_3$.

* * * * *

UNITED STATES PATENT AND TRADEMARK OFFICE
CERTIFICATE OF CORRECTION

PATENT NO.        : 11,274,097 B2
APPLICATION NO.   : 16/385249
DATED             : March 15, 2022
INVENTOR(S)       : Ruediger Fischer et al.

It is certified that error appears in the above-identified patent and that said Letters Patent is hereby corrected as shown below:

On the Title Page

Please delete:
"(62) Related U.S. Application Data
Division of application No. 15/119,124, filed as application No. PCT/EP2015/052351 on Feb. 5, 2015, now Pat. No. 10,364,243."

And replace with:
--(63) Related U.S. Application Data
Continuation of application No. 15/119,124, filed as application No. PCT/EP2015/052351 on Feb. 5, 2015, now Pat. No. 10,364,243.--

Signed and Sealed this
Twelfth Day of July, 2022

Katherine Kelly Vidal
*Director of the United States Patent and Trademark Office*